US007524849B2

(12) United States Patent
Zhang et al.

(10) Patent No.: US 7,524,849 B2
(45) Date of Patent: Apr. 28, 2009

(54) 5-ARYLPYRIMIDINES AS ANTICANCER AGENTS

(75) Inventors: Nan Zhang, Bayside, NY (US); Semiramis Ayral-Kaloustian, Tarrytown, NY (US); Thai Nguyen, Fair Lawn, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 461 days.

(21) Appl. No.: 10/950,375

(22) Filed: Sep. 24, 2004

(65) Prior Publication Data

US 2005/0075357 A1 Apr. 7, 2005

Related U.S. Application Data

(60) Provisional application No. 60/505,487, filed on Sep. 24, 2003.

(51) Int. Cl.
*C07D 239/42* (2006.01)
*C07D 239/48* (2006.01)
*A61K 31/505* (2006.01)

(52) U.S. Cl. .................. 514/255.05; 514/256; 514/275; 544/295; 544/323; 544/324; 544/328; 544/330; 544/331

(58) Field of Classification Search ................. 544/295, 544/323, 324, 328, 330, 331; 514/255.05, 514/256, 275
See application file for complete search history.

(56) References Cited

U.S. PATENT DOCUMENTS

| 5,986,135 | A | 11/1999 | Pfrengle et al. |
| 6,117,876 | A | 9/2000 | Pees et al. |
| 6,156,925 | A | 12/2000 | Meyer et al. |
| 6,204,269 | B1 | 3/2001 | Pfrengle et al. |
| 6,297,251 | B1 | 10/2001 | Pees et al. |
| 6,509,354 | B1 | 1/2003 | Toriyabe et al. |
| 6,632,821 | B2 | 10/2003 | Pees et al. |
| 6,670,362 | B2 | 12/2003 | Banks et al. |
| 2002/0061889 | A1 | 5/2002 | Banks et al. |
| 2003/0069242 | A1 | 4/2003 | Toriyabe et al. |
| 2003/0088096 | A1 | 5/2003 | Pees et al. |
| 2003/0092718 | A1 | 5/2003 | Haap et al. |
| 2004/0116429 | A1 | 6/2004 | Grote et al. |
| 2004/0147744 | A1 | 7/2004 | Pees et al. |

FOREIGN PATENT DOCUMENTS

| WO | WO 98/30550 | | 8/1998 |
| WO | WO 01/96314 | A1 | 12/2001 |
| WO | WO 02/074753 | A2 | 9/2002 |
| WO | WO 03/043993 | A1 | 5/2003 |
| WO | WO 03/070721 | A1 | 8/2003 |
| WO | WO 03/077656 | A1 | 9/2003 |
| WO | WO 2004/048365 | A1 | 6/2004 |

OTHER PUBLICATIONS

Nogales et al., Structural mechanisms underlying nucleotide-dependent self-assembly of tubulin and its relatives, Current Opinion in Structural Biology, 16:221-229, 2006.*
Simone, Oncology: Introduction, Cecil Textbook of Medicine, 20th Edition, vol. 1, pp. 1004-1010, 1996.*
M.C. Wani, et al.; J. Am. Chem. Soc.; vol. 93; pp. 2325-2327; 1971.
Steven R. Koepke, et al.; J. Org. Chem.; vol. 44; No. 15; 1979.
Peter B. Schiff, et al.; Nature; vol. 277; pp. 665-667; 1979.
Nirbhay Kumar; J. Biol. Chem.; vol. 256; No. 20; pp. 10435-10441; 1981.
Ernest Hamel, et al.; The Journal of Biological Chemistry; vol. 259; No. 4; pp. 2501-2508; 1984.
Ding-Wu Shen, et al.; J. Biol. Chem.; vol. 261; No. 17; pp. 7762-7770; 1986.
Tim McGrath and Melvin S. Center; Biochem. Biophys. Res. Commun.; vol. 145; No. 3; pp. 1171-1176; 1987.
William P. McGuire, et al.; Ann. Int. Med.; vol. III; pp. 273-279; 1989.
Lori J. Goldstein, et al.; J. Natl. Cancer Inst. (Bethesda); vol. 81; pp. 116-124; 1989.
Eric K. Rowinsky, et al.; J. Natl. Cancer Inst.; vol. 82; No. 15; pp. 1247-1259; 1990.
Frankie Ann Holmes, et al.; J. Natl. Cancer Inst.; vol. 83; No. 24; pp. 1797-1805; 1991.
Annette Bicher, et al.; Anti-Cancer Drugs; vol. 4; pp. 141-148; 1993.
Tadahiro Takemoto, et al.; J. Med. Chem.; vol. 37; pp. 18-25; 1994.
Robert A. Holton, et al.; J. Am. Chem. Soc.; vol. 116; No. 4; pp. 1597-1600; 1994.
K.C. Nicolaou, et al.; Nature; vol. 367; pp. 630-634; 1994.
Elise C. Kohn, et al.; Journal of the National Cancer Institute; vol. 86; No. 1; pp. 18-24; 1994.
Ernest Hamel; Med. Res. Rev.; vol. 16; pp. 207-231; 1996.
Sridhar K. Rabindran, et al.; Cancer Res.; vol. 58; pp. 5850-5858; 1998.
Chun Li, et al.; Science & Medicine; Jan./Feb.; pp. 38-47; 1999.
Eric K. Rowinsky and Anthony W. Tolcher; Cancer Principles and Practice; pp. 431-452; 2001.
Michael M. Gottesman; Annu. Rev. Med.; vol. 53; pp. 615-627; 2002.
Michael M. Gottesman, et al.; Nature Rev. Cancer; vol. 2; pp. 48-58; 2002.
Frank Loganzo, et al.; Cancer Res.; vol. 63; pp. 1838-1845; 2003.

* cited by examiner

*Primary Examiner*—Deepak Rao
(74) *Attorney, Agent, or Firm*—Joel Silver; Karen DeBenedictis; Stephen E. Johnson

(57) ABSTRACT

This invention relates to certain 5-arylpyrimidine compounds or a pharmaceutically acceptable salt thereof, and compositions containing said compounds or a pharmaceutically acceptable salt thereof, wherein said compounds are anticancer agents useful for the treatment of cancer in mammals. This invention further relates to a method of treating or inhibiting the growth of cancerous tumor cells and associated diseases in a mammal and further provides a method for the treatment or prevention of cancerous tumors that express multiple drug resistance (MDR) or are resistant because of MDR, in a mammal in need thereof which method comprises administering to said mammal an effective amount of said compounds or a pharmaceutically acceptable salt thereof.

More specifically, the present invention relates to a method of treating or inhibiting the growth of cancerous tumor cells and associated diseases in a mammal in need thereof by promotion of microtubule polymerization which comprises administering to said mammal an effective amount of said compounds and pharmaceutically acceptable salts thereof.

77 Claims, No Drawings

5-ARYLPYRIMIDINES AS ANTICANCER AGENTS

"This application claims priority from Provisional Application No. 60/505,487 filed Sep. 24, 2003 the entire disclosure of which is hereby incorporated by reference".

FIELD OF THE INVENTION

The present invention relates to certain 5-arylpyrimidine compounds or a pharmaceutically acceptable salt thereof, and compositions containing said compounds or a pharmaceutically acceptable salt thereof, wherein said compounds are anti-cancer agents useful for the treatment of cancer in mammals, treatment or prevention of cancerous tumors that express multiple drug resistance (MDR) or are resistant because of MDR, and treating or inhibiting the growth of cancerous tumor cells and associated diseases in a mammal in need thereof by promotion of microtubule polymerization.

BACKGROUND OF THE INVENTION

Most of the cytostatics in use today either inhibit the formation of essential precursors for biosynthesis of DNA or block DNA polymerases or interfere with the template function of DNA because DNA was the primary target for developing therapeutic drugs for chemotherapy. Unfortunately, inhibition of the formation of essential precursors for biosynthesis of DNA or blocking DNA polymerases or interference with the template function of DNA also affects normal tissues.

Antimicrotubule drugs are a major category of anticancer agents (Rowinsky, E. K., and Tolcher, A. W. Antimicrotubule agents. In: V. T. Devita, Jr., S. Hellman, and S. A. Rosenberg (eds.), Cancer Principles and Practice, Ed. 6, pp. 431-452. Philadelphia: Lippincott Williams and Wilkins, 2001). They work by interfering with the function of cellular microtubules, particularly the mitotic spindle. The disruption of normal spindle function leads to apoptotic cell death.

Currently, there are three major classes of known antimicrotubule pharmacological agents. Each has a distinct binding region on β-tubulin and distinct effects on microtubule function. These classes are: 1) taxane-site agents which promote microtubule formation and stabilize microtubules; 2) vinca/peptide-site agents which destabilize microtubules and often induce formation of abnormal polymers or aggregates at high concentrations; and 3) colchicine-site agents which also destabilize microtubules and generally do not induce other polymers (Hamel, E. Antimitotic natural products and their interactions with tubulin. Med. Res. Rev., 16: 207-231, 1996). Most of the ligands for all three classes of sites are natural products or semi-synthetic derivatives of natural products.

Paclitaxel and its semisynthetic derivative docetaxel (Taxotere®) interfere with microtubule formation and stabilize microtubules. Paclitaxel (Taxol®), is a diterpene isolated from the bark of the Western (Pacific) yew, *Taxus brevifolia* and is representative of a new class of therapeutic agent having a taxane ring system. It was additionally found in other members of the Taxacae family including the yew of Canada (*Taxus canadensis*) found in Gaspesia, eastern Canada and *Taxus baccata* found in Europe whose needles contain paclitaxel and analogs and hence provide a renewable source of paclitaxel and derivatives. The crude extract was tested for the first time during the 1960s and its active principle was isolated in 1971 and the chemical structure identified (M. C. Wani et al, J. Am. Chem. Soc., 93, 2325 (1971)). Further, a wide range of activity over melanoma cells, leukemia, various carcinomas, sarcomas and non-Hodgkin lymphomas as well as a number of solid tumors in animals was shown through additional testing. Paclitaxel and its analogs have been produced by partial synthesis from 10-deacetylbaccatin III, a precursor obtained from yew needles and twigs, and by total synthesis (Holton, et al., J. Am. Chem. Soc. 116:1597-1601 (1994) and Nicolaou, et al., Nature 367:630-634 (1994)). Paclitaxel has been demonstrated to possess antineoplastic activity. More recently, it was shown that the antitumor activity of paclitaxel is due to a promotion of microtubule polymerization (Kumar, N., J. Biol. Chem. 256:10435-10441 (1981); Rowinsky, et al., J. Natl. Cancer Inst., 82:1247-1259 (1990); and Schiff, et al., Nature, 277:665-667 (1979)). Paclitaxel has now demonstrated efficacy in several human tumors in clinical trials (McGuire, et al., Ann. Int. Med., 111:273-279 (1989); Holmes, et al., J. Natl. Cancer Inst., 83:1797-1805 (1991); Kohn et al., J. Natl. Cancer Inst., 86:18-24 (1994); and A. Bicker et al., Anti-Cancer Drugs, 4, 141-148 (1993).

Two taxane-site agents (paclitaxel and docetaxel) and three vinca/peptide-site agents (vinblastine, vincristine, and vinorelbine) are used clinically to treat various human cancers. Taxanes have proven to be of greater utility against solid tumors (e.g., lung, breast, ovarian) than the vinca alkaloids, suggesting that agents that promote microtubule formation might be superior clinically to those that destabilize microtubules. Colchicine-site agents are not used therapeutically.

Despite the widespread clinical use of paclitaxel and docetaxel, these drugs have several limitations that create a need for improved agents. First, many tumors are inherently resistant (e.g., colon tumors) or become resistant after multiple cycles of treatment, at least in part due to the expression of drug transporters located in cancer cell membranes that pump the drugs out of cells and thereby decrease their efficacy (Gottesman, M. M. Mechanisms of cancer drug resistance. Annu. Rev. Med., 53: 615-627, 2002). The best known of these transporters is P-glycoprotein. Accordingly, there is a need for new agents with taxane-like effects on microtubule polymerization that are not substrates of P-glycoprotein or other such pumps and that therefore will overcome this cause of taxane resistance in patients.

Second, paclitaxel and docetaxel have poor water solubility and paclitaxel must be formulated in Cremophor EL, a vehicle that induces serious hypersensitivity reactions (Li, C. L., Newman, R. A., and Wallace, S. Reformulating paclitaxel. Science & Medicine, January/February: 38-47, 1999). Patients are typically premedicated with corticosteroids and antihistamines before administration of paclitaxel to minimize these toxicities. Accordingly, there is a need for new agents with taxane-like effects on microtubule polymerization that are highly water soluble and can be administered in physiological saline or other suitable non-toxic vehicle.

Third, paclitaxel is a natural product having a highly complex structure, and docetaxel is a closely related semisynthetic derivative. Therefore there is a need for compounds which are readily available through synthesis, are structurally different from taxanes and which have taxane-like effects on microtubule polymerization.

Accordingly, there is still a need in the art for cytotoxic agents for use in cancer therapy. In particular, there is a need for cytotoxic agents which inhibit or treat the growth of tumors which have an effect similar to paclitaxel and interfere with the process of microtubule formation. Additionally, there is a need in the art for agents which accelerate tubulin polymerization and stabilize the assembled microtubules.

Accordingly, it would be advantageous to provide new compounds which provide a method of treating or inhibiting cell proliferation, neoplastic growth and malignant tumor growth in mammals by administering compounds which have paclitaxel like anticancer activity.

Additionally, it would be advantageous to provide new compounds which provide a method for treating or inhibiting growth of cancerous tumors that express multiple drug resistance (MDR) or are resistant because of MDR.

Further, it would be advantageous to provide new compounds which provide a method of treating or inhibiting the growth of cancerous tumors in a mammal with inherent or acquired resistance to chemotherapeutic agents and in particular antimitotic agents.

The preparation and use of 5-phenyl substituted 2-(cyanoamino)pyrimidines having the following general formula as fungicides are disclosed in WO01/96314 A1.

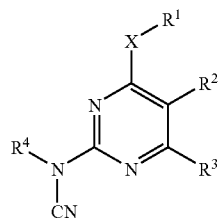

The preparation and use of 5-phenylpyrimidines having the following general formula as fungicides are disclosed in WO02/074753 A2.

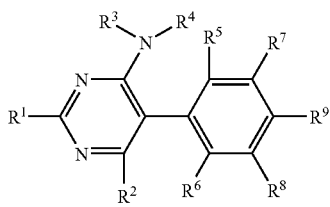

The preparation and use of 4-amino-2-(pyrin-2-yl)pyrimidines having the following general formula as microbicidal active substances are disclosed in WO02/074753 A2.

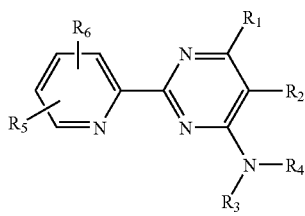

The compounds of this invention are a new class of taxane-like agents that satisfy the hereinbefore described needs, and that differ in significant ways from the previously known classes of antimicrotubule compounds. The compounds of this invention bind at the vinca site of β-tubulin, yet they have many properties that are similar to taxanes and distinct from vinca-site agents. In particular, the compounds of this invention enhance the polymerization of microtubule-associated protein (MAP)-rich tubulin in the presence of GTP at low compound:tubulin molar ratios, in a manner similar to paclitaxel and docetaxel. The compounds of this invention also induce polymerization of highly purified tubulin in the absence of GTP under suitable experimental conditions, an activity that is a hallmark of taxanes. The compounds of this invention are potently cytotoxic for many human cancer cell lines in culture, including lines that overexpress the membrane transporters MDR (P-glycoprotein), MRP, and MXR, thus making them active against cell lines that are resistant to paclitaxel and vincristine. In particular, representative examples of this invention have high water solubility and can be formulated in saline. Representative examples of this invention are active as anti-tumor agents in athymic mice bearing human tumor xenografts of lung and colon carcinoma, melanoma, and glioblastoma, when dosed either intravenously or orally.

SUMMARY OF THE INVENTION

In accordance with the present invention, there are provided compounds represented by Formula (I):

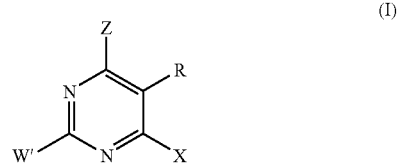

wherein:
Z is selected from:

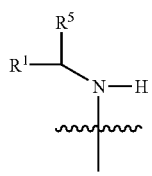

and $C_6$-$C_8$ cycloalkyl;
R is a moiety

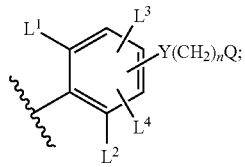

n is an integer of 2, 3, or 4;
$L^1$ and $L^2$, are each independently H, F, Cl or Br;
$L^3$ and $L^4$ are H;
X is Cl or Br;
Y is O, S, or —$NR^2$;
Q is OH or —$NR^3R^4$;
$R^1$ is H or $C_1$-$C_3$ alky;
$R^2$ is H or $C_1$-$C_3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;

W' is —NHR$^6$, —N(CN)R$^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

R$^6$ is $C_1$-$C_3$ alkyl;

R$^7$ is $C_1$-$C_3$ alkyl;

or a pharmaceutically acceptable salt thereof.

DEFINITIONS

As used herein the term alkyl means a straight or branched alkyl moiety of 1 to 3 carbon atoms.

As used herein alkoxy means an alkyl-O— group in which the alkyl group is as previously described. Exemplary alkoxy groups include but are not limited to methoxy, ethoxy, and n-propoxy.

As used herein alkoxycarbonyl means a moiety —C(O)(O)alkyl in which the alkyl group is as previously described.

As used herein carboxyl means a —COOH group.

As used herein alkanoyl means a —C(O)alkyl group where alkyl is previously defined.

As used herein alkylthio means an alkyl-S— group in which the alkyl group is as previously described.

As used herein alkylamido means a —C(O)NHalkyl group where alkyl is previously described.

As used herein a heterocyclic ring is a saturated 4 to 6 membered ring which contains 1-2 nitrogen atoms, 0-1 oxygen atoms and 0-1 sulfur atoms within the ring where said ring is optionally substituted with $C_1$-$C_3$ alkyl. Non-limiting representative examples include: morpholine, piperidine, pyrrolidine, piperazine, and azetidine.

As used herein aryl means a monocyclic or bicyclic aromatic ring having from 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups. A preferred embodiment of aryl is a aromatic ring having 6 carbon atoms. Non-limiting representative aryl examples include: phenyl, 1-naphthyl, and 2-naphthyl.

As used herein heteroaryl is an aromatic heterocyclic ring system (monocyclic or bicyclic) of 5 to 10 ring atoms having from 1 to 4 heteroatoms selected from S, O and N and optionally substituted with 1-3 groups including but not limited to halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups. A preferred embodiment of heteroaryl is a aromatic heterocyclic ring system which has 5 or 6 ring atoms having 1 or 2 nitrogen heteroatoms. Non-limiting representative heteroaryl examples include: 1-pyrazolyl, 2-pyrazinyl, 2-pyridyl, 2-pyrimidinyl, and 3-isoquinolinyl.

Cycloalkyl as used herein means a saturated carbocyclic monocyclic ring having from 6 to 8 carbon atoms optionally substituted with $C_1$-$C_3$ alkyl. Non-limiting representative examples include: cyclohexyl, cycloheptyl and cyclooctyl.

As used herein halogen means F, Cl or Br.

Phenyl as used herein refers to a 6-membered carbon aromatic ring.

As used herein phenoxy means a —O-phenyl group where phenyl is as previously described.

As used herein benzyl means a —CH$_2$-phenyl group where phenyl is as previously described.

As used herein benzyloxy means a —O—CH$_2$-phenyl group where phenyl is as previously described.

As used herein N-methylamine means a moiety of the formula

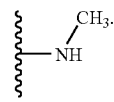

As used herein alkyl amino means a moiety of the formula

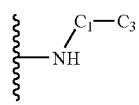

As used herein dialkylamino means a moiety of the formula

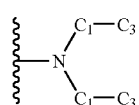

As used herein N-methylcyanamido means a moiety of the formula

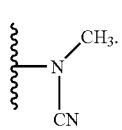

The present invention provides a method of treating or inhibiting the growth of cancerous tumor cells and associated diseases in a mammal in need thereof by administering an effective amount of a compound of Formula (I) and pharmaceutically acceptable salts thereof.

The present invention also provides a method of treating or inhibiting the growth of cancerous tumor cells and associated diseases in mammals in need thereof by interacting with tubulin and microtubules by promotion of microtubule polymerization which comprises administering to said mammal an effective amount of a compound of Formula (I) and pharmaceutically acceptable salts thereof. A method for promoting tubulin polymerization involves contacting a tubulin containing system with an effective amount of a compound of the invention.

Also provided by the present invention is a method for the treatment or prevention of tumors that express multiple drug resistance (MDR) or are resistant because of MDR in a mammal in need thereof which method comprises administering to said mammal an effective amount of a compound of Formula (I) or a pharmaceutically acceptable salt thereof.

This invention further provides a method of promoting tubulin polymerization in a tubulin containing system by contacting said tubulin containing system with an effective amount of a compound of Formula (I) or a pharmaceutically acceptable salt thereof.

Additionally this invention provides a method of stabilizing microtubules in a tubulin containing system which comprises contacting said tubulin containing system with an effective amount of a compound of Formula (I) or a pharmaceutically acceptable salt thereof.

Also provided by this invention is a compound of Formula (I) in combination or association with a pharmaceutically acceptable carrier. In particular, the present invention provides a pharmaceutical composition which comprises an effective amount of a compound of Formula (I) and a pharmaceutically acceptable carrier.

Additionally this invention provides a method of treating, inhibiting the growth of, or eradicating a tumor in a mammal in need thereof wherein said tumor is resistant to at least one chemotherapeutic agent which comprises administering to said mammal an effective amount of the compounds of Formula (I) and pharmaceutically acceptable salts thereof.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. Included in the scope of the present invention are (R) and (S) isomers of compounds of general Formula (I) having a chiral center and the racemates thereof and in particular compounds of formula (Ia) and formula (Ib). A preferred embodiment of this invention are (S) isomers of compounds of general Formula (I) having a chiral center. An additional preferred embodiment of this invention are (R) isomers of compounds of general Formula (I) having a chiral center. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Optical isomers may be obtained in pure form by standard separation techiques or enantiomer specific synthesis.

A preferred embodiment of the invention is a compound of formula (Ia):

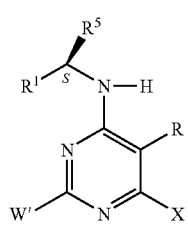

(Ia)

or a pharmaceutically acceptable salt thereof.

A preferred embodiment of the invention is a compound of formula (Ib):

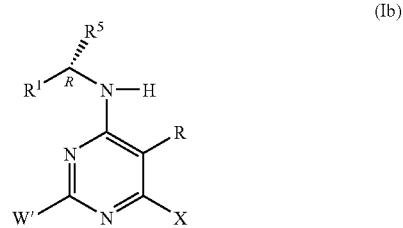

(Ib)

or a pharmaceutically acceptable salt thereof.

A further preferred embodiment are compounds of Formula (I) wherein R is the moiety

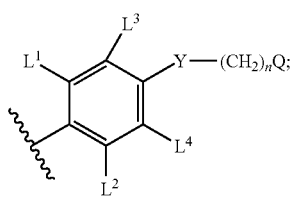

or a pharmaceutically acceptable salt thereof.

Also preferred are compounds of Formula (I) where Z is $C_6$-$C_8$ cycloalkyl or a pharmaceutically acceptable salt thereof.

Among the more preferred group of compounds of this invention according to Formula (Ia) including pharmaceutically acceptable salts thereof are those wherein:

R is the moiety:

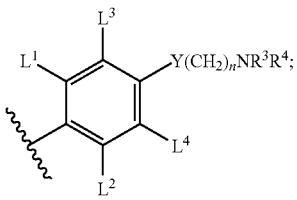

n=3;
$R^1$ is H or methyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$;
$R^7$ is $C_1$-$C_3$ alkyl;
$L^1$ is F;
$L^2$ is F;
$L^3$ is H;
$L^4$ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups.

Among the more preferred group of compounds of this invention according to Formula (Ib) including pharmaceutically acceptable salts thereof are those wherein:
R is the moiety:

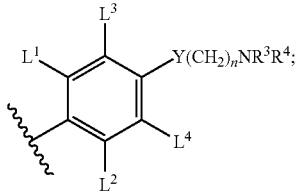

n=3;
R$^1$ is H or methyl;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^5$ is CF$_3$;
R$^7$ is C$_1$-C$_3$ alkyl;
L$^1$ is F;
L$^2$ is F;
L$^3$ is H;
L$^4$ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups.

A further more preferred group of compounds of this invention according to Formula (I) including pharmaceutically acceptable salts thereof are those wherein:
Z is C$_6$-C$_8$ cycloalkyl;
R is the moiety:

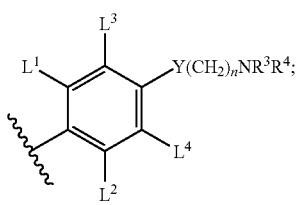

n=3;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^7$ is C$_1$-C$_3$ alkyl;
L$^1$ is F;
L$^2$ is F;
L$^3$ is H;
L$^4$ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups.

Specifically preferred compounds of this invention according to Formula (I) are the following compounds or pharmaceutically acceptable salts thereof:
4-chloro-5-{4-[3-(dimethylamino)propoxy]-2,6-difluorophenyl}-6-[(2,2,2-trifluoroethyl)amino]pyrimidin-2-yl (methyl)cyanamide,
6-chloro-5-{4-[3-(dimethylamino)propoxy]-2,6-difluorophenyl}-N$^2$-methyl-N$^4$-(2,2,2-trifluoroethyl)pyrimidine-2,4-diamine,
(4-chloro-5-{4-[3-(dimethylamino)propoxy]-2,6-difluorophenyl}-6-{[2,2,2-trifluoro-1-methylethyl]amino}pyrimidin-2-yl)methylcyanamide,
4-chloro-5-{4-[2-(dimethylamino)ethoxy]-2,6-difluorophenyl}-6-[(2,2,2-trifluoroethyl)amino]pyrimidin-2-yl(methyl)cyanamide,
{4-chloro-5-{4-[4-(dimethylamino)butoxy]-2,6-difluorophenyl}-6-[(2,2,2-trifluoroethyl)amino]pyrimidin-2-yl}methylcyanamide,
6-chloro-5-{2,6-difluoro-4-[3-(methylamino)propoxy]phenyl}-2-pyrazin-2-yl-N-[2,2,2-trifluoro-1-methylethyl]pyrimidin-4-amine,
6-chloro-5-{4-[3-(dimethylamino)propoxy]-2,6-difluorophenyl}-2-pyrazin-2-yl-N-(2,2,2-trifluoroethyl)pyrimidin-4-amine,
6-chloro-5-{4-[3-(dimethylamino)propoxy]-2,6-difluorophenyl}-N-(2,2,2-trifluoroethyl)-2,2'-bipyrimidin-4-amine,
6-chloro-5-{4-[3-(dimethylamino)propoxy]-2,6-difluorophenyl}-2-(1H-imidazol-1-yl)-N-(2,2,2-trifluoroethyl)pyrimidin-4-amine,
6-chloro-5-{2,6-difluoro-4-[3-(methylamino)propoxy]phenyl}-2-(1H-pyrazol-1-yl)-N-[2,2,2-trifluoro-1-methylethyl)pyrimidin-4-amine,
N-{3-[4-(4-chloro-6-cycloheptyl-2-pyrazin-2-ylpyrimidin-5-yl)-3,5-difluorophenoxy]propyl}-N-methylamine,
6-chloro-5-{4-[2-(dimethylamino)ethoxy]-2,6-difluorophenyl}-2-pyrazin-2-yl-N-(2,2,2-trifluoroethyl)pyrimidin-4-amine,
6-chloro-5-{4-[4-(dimethylamino)butoxy]-2,6-difluorophenyl}-2-pyrazin-2-yl-N-(2,2,2-trifluoroethyl)pyrimidin-4-amine,
6-chloro-5-{2,6-difluoro-4-[3-(methylamino)propoxy]phenyl}-2-pyridin-2-yl-N-[2,2,2-trifluoro-1-methylethyl]pyrimidin-4-amine,
6-chloro-5-{4-[3-(dimethylamino)propoxy]-2,6-difluorophenyl}-2-quinolin-2-yl-N-(2,2,2-trifluoroethyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine.

Specifically preferred compounds of this invention according to formula (Ia) are the following compounds or pharmaceutically acceptable salts thereof:
(4-chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide,
6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine,
6-chloro-5-{2,6-difluoro-4-[3-(dimethylamino)propoxy]phenyl}-2-(1H-pyrazol-1-yl)-N-[(1S)-2,2,2-trifluoro-1-methylethyl)pyrimidin-4-amine and
6-chloro-5-{2,6-difluoro-4-[3-(methylamino)propoxy]phenyl}-2-pyridin-2-yl-N-[(1S)-2,2,2-trifluoro-1-methylethyl]pyrimidin-4-amine.

Specifically preferred compounds of this invention according to formula (Ib) are the following compounds or pharmaceutically acceptable salts thereof:

(4-chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide, 6-chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine, 6-chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine and 6-chloro-5-{2,6-difluoro-4-[3-(methylamino)propoxy]phenyl}-2-pyridin-2-yl-N-[(1R)-2,2,2-trifluoro-1-methylethyl]pyrimidin-4-amine.

The present invention provides:

(i) a method of treating or inhibiting the growth of cancerous tumor cells and associated diseases in a mammal in need thereof by administering an effective amount of a compound of formula (II) and pharmaceutically acceptable salts thereof;

(ii) a method of treating or inhibiting the growth of cancerous tumor cells and associated diseases in mammals in need thereof by interacting with tubulin and microtubules by promotion of microtubule polymerization which comprises administering to said mammal an effective amount of the compounds of formula (II) and pharmaceutically acceptable salts thereof;

(iii) a method for promoting tubulin polymerization which involves contacting a tubulin containing system with an effective amount of a compound of the invention;

(iv) a method for the treatment or prevention of tumors that express multiple drug resistance (MDR) or are resistant because of MDR in a mammal in need thereof which method comprises administering to said mammal an effective amount of compounds of formula (II) or pharmaceutically acceptable salts thereof;

(v) a method of promoting tubulin polymerization in a tubulin containing system which comprises contacting said tubulin containing system with an effective amount of a compound of formula (II) or pharmaceutically acceptable salts thereof;

(vi) a method of stabilizing microtubules in a microtubule containing system which comprises contacting said microtubule containing system with an effective amount of a compound of formula (II) or a pharmaceutically acceptable salt thereof;

(vii) a method of treating, inhibiting the growth of, or eradicating a tumor in a mammal in need thereof wherein said tumor is resistant to at least one chemotherapeutic agent which comprises administering to said mammal an effective amount of the compounds of formula (II) and pharmaceutically acceptable salts thereof;

The present invention further provides a pharmaceutical composition which comprises a compound of formula (II) in combination or association with a pharmaceutically acceptable carrier. In particular, the present invention provides a pharmaceutical composition which comprises an effective amount of a compound of formula (II) and a pharmaceutically acceptable carrier.

The compounds of formula (II) may contain an asymmetric carbon atom and some of the compounds of this invention may contain one or more asymmetric centers and may thus give rise to stereoisomers, such as enantiomers and diastereomers. The stereoisomers of formula (II) are named according to the Cahn-Ingold-Prelog System. While shown without respect to stereochemistry in Formula (II), the present invention includes all the individual possible stereoisomers as well as the racemic mixtures and other mixtures of R and S stereoisomers (scalemic mixtures which are mixtures of unequal amounts of enantiomers) and pharmaceutically acceptable salts thereof. Included in the scope of the present invention are (R) and (S) isomers of compounds of general formula (II) having a chiral center and the racemates thereof and in particular compounds of formula (IIa) and formula (IIb). A preferred embodiment of this invention are (S) isomers of compounds of general formula (II) having a chiral center. An additional preferred embodiment of this invention are (R) isomers of compounds of general formula (II) having a chiral center. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Optical isomers may be obtained in pure form by standard separation techiques or enantiomer specific synthesis.

The present invention also provides a method of treating or inhibiting the growth of cancerous tumor cells and associated diseases in a mammal in need thereof by administering an effective amount of a compound of formula (II):

(II)

wherein:
Z is selected from:

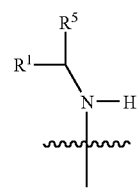

and $C_6$-$C_8$ cycloalkyl;
R is a moiety

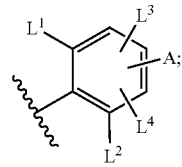

X is Cl or Br;
$L^1$, $L^2$, $L^3$ and $L^4$ are each independently H, F, Cl or Br;
A is H, F, Cl, Br, or $Y(CH_2)_nQ$;
Y is O, S, or $NR^2$;
n is an integer of 2, 3, or 4;
Q is OH or —$NR^3R^4$;
$R^1$ is H or $C_1$-$C_3$ alkyl;
$R^2$ is H or $C_1$-$C_3$ alkyl;

$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;

$R^5$ is $CF_3$ or $C_2F_5$;

W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

$R^6$ is $C_1$-$C_3$ alkyl;

$R^7$ is $C_1$-$C_3$ alkyl;

and pharmaceutically acceptable salts thereof.

A preferred embodiment of the present invention is to provide a method of treating or inhibiting the growth of cancerous tumor cells and associated diseases in a mammal in need thereof which comprises administering an effective amount of a compound according to Formula (IIa):

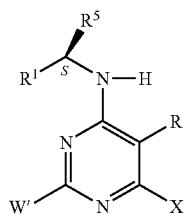

(IIa)

or pharmaceutically acceptable salts thereof.

A preferred embodiment of the present invention is to provide a method of treating or inhibiting the growth of cancerous tumor cells and associated diseases in a mammal in need thereof which comprises administering an effective amount of a compound according to Formula (IIb):

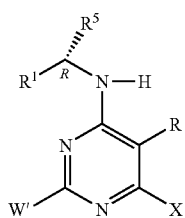

(IIb)

or pharmaceutically acceptable salts thereof.

Further preferred embodiment of the present invention is to provide a method of treating or inhibiting the growth of cancerous tumor cells and associated diseases in a mammal in need thereof which comprises administering an effective amount of a compound according to formula (II) wherein R is a moiety

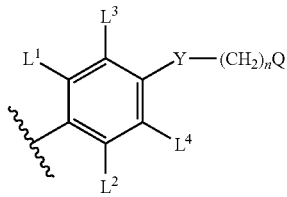

or pharmaceutically acceptable salts thereof.

Among the more preferred embodiments of the present invention is to provide a method of treating or inhibiting the growth of cancerous tumor cells and associated diseases in a mammal in need thereof which comprises administering an effective amount of a compound according to Formula (IIa) including pharmaceutically acceptable salts thereof wherein:

R is a moiety

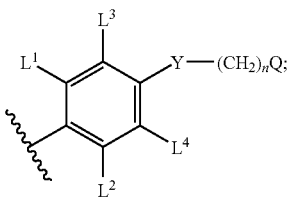

n=3;

Y is O;

Q is —$NR^3R^4$;

$R^1$ is H or methyl;

$R^5$ is $CF_3$;

$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;

$R^6$ is $C_1$-$C_3$ alkyl;

$R^7$ is $C_1$-$C_3$ alkyl;

$L^1$ is F;

$L^2$ is H or F;

$L^3$ is H;

$L^4$ is H;

X is Cl or Br;

or a pharmaceutically acceptable salt thereof.

Among the more preferred embodiments of the present invention is to provide a method of treating or inhibiting the growth of cancerous tumor cells and associated diseases in a mammal in need thereof which comprises administering an effective amount of a compound according to Formula (IIb) including pharmaceutically acceptable salts thereof wherein:

R is a moiety

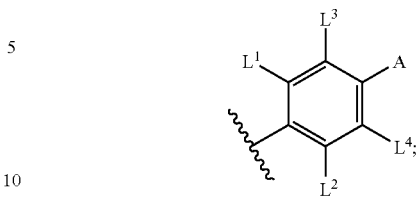

n=3;
Y is O;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;

or a pharmaceutically acceptable salt thereof.

Among the more preferred embodiments of the present invention is to provide a method of treating or inhibiting the growth of cancerous tumor cells and associated diseases in a mammal in need thereof which comprises administering an effective amount of compounds according to Formula (IIa) including pharmaceutically acceptable salts thereof are those wherein:

R is a moiety

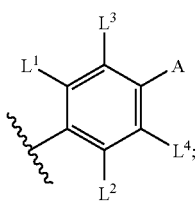

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;

or pharmaceutically acceptable salts thereof.

Among the more preferred embodiments of the present invention is to provide a method of treating or inhibiting the growth of cancerous tumor cells and associated diseases in a mammal in need thereof which comprises administering an effective amount of compounds according to Formula (IIb) including pharmaceutically acceptable salts thereof wherein:

R is a moiety

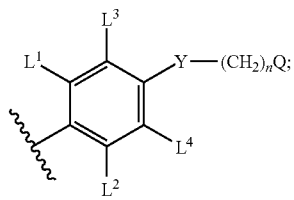

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;

or pharmaceutically acceptable salts thereof.

Specifically preferred compounds of this invention according to formula (II) useful in a method of treating or inhibiting the growth of cancerous tumor cells and associated diseases in a mammal in need thereof which comprises administering an effective amount of a compound or pharmaceutically acceptable salt thereof selected from:

4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine,
6-Chloro-2-pyridin-4-yl-N-(2,2,2-trifluoroethyl)-5-(2,4,6-trifluorophenyl)pyrimidin-4-amine,
6-Chloro-2-pyridin-3-yl-N-(2,2,2-trifluoroethyl)-5-(2,4,6-trifluorophenyl)pyrimidin-4-amine,
6-Chloro-2-pyridin-2-yl-N-(2,2,2-trifluoroethyl)-5-(2,4,6-trifluorophenyl)pyrimidin-4-amine,
6-Chloro-2-pyridin-2-yl-N-[2,2,2-trifluoro-1-methylethyl]-5-(2,4,6-trifluorophenyl)pyrimidin-4-amine,
6-Chloro-2-quinolin-2-yl-N-(2,2,2-trifluoroethyl)-5-(2,4,6-trifluorophenyl)pyrimidin-4-amine,
6-Chloro-2-isoquinolin-1-yl-N-(2,2,2-trifluoroethyl)-5-(2,4,6-trifluorophenyl)pyrimidin-4-amine,
6-Chloro-2-isoquinolin-3-yl-N-(2,2,2-trifluoroethyl)-5-(2,4,6-trifluorophenyl)pyrimidin-4-amine,
6-Chloro-2-thien-2-yl-N-(2,2,2-trifluoroethyl)-5-(2,4,6-trifluorophenyl)pyrimidin-4-amine,
6-Chloro-2-(2-furyl)-N-(2,2,2-trifluoroethyl)-5-(2,4,6-trifluorophenyl)pyrimidin-4-amine,
6-Chloro-2-(1H-imidazol-1-yl)-N-(2,2,2-trifluoroethyl)-5-(2,4,6-trifluorophenyl)pyrimidin-4-amine,
6-Chloro-2-(1H-pyrazol-1-yl)-N-(2,2,2-trifluoroethyl)-5-(2,4,6-trifluorophenyl)pyrimidin-4-amine,
6-Chloro-2-(1H-pyrazol-1-yl)-N-[2,2,2-trifluoro-1-methylethyl]-5-(2,4,6-trifluorophenyl)pyrimidin-4-amine,
6-Chloro-2-(1H-pyrrol-1-yl)-N-(2,2,2-trifluoroethyl)-5-(2,4,6-trifluorophenyl)pyrimidin-4-amine,
4-Chloro-5-{4-[3-(dimethylamino)propoxy]-2,6-difluorophenyl}-6-[(2,2,2-trifluoroethyl)amino]pyrimidin-2-yl(methyl)cyanamide, 6-Chloro-5-{4-[3-(dimethylamino)propoxy]-2,6-difluorophenyl}-$N^2$-methyl-$N^4$-(2,2,2-trifluoroethyl)pyrimidine-2,4-diamine,
(4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
4-Chloro-5-{4-[2-(dimethylamino)ethoxy]-2,6-difluorophenyl}-6-[(2,2,2-trifluoroethyl)amino]pyrimidin-2-yl(methyl)cyanamide,
{4-Chloro-5-{4-[4-(dimethylamino)butoxy]-2,6-difluorophenyl}-6-[(2,2,2-trifluoroethyl)amino]pyrimidin-2-yl}methylcyanamide,
6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
6-Chloro-5-{4-[3-(dimethylamino)propoxy]-2,6-difluorophenyl}-2-pyrazin-2-yl-N-(2,2,2-trifluoroethyl)pyrimidin-4-amine,
6-Chloro-5-{4-[3-(dimethylamino)propoxy]-2,6-difluorophenyl}-N-(2,2,2-trifluoroethyl)-2,2'-bipyrimidin-4-amine,
6-Chloro-5-{4-[2-(dimethylamino)ethoxy]-2,6-difluorophenyl}-2-pyrazin-2-yl-N-(2,2,2-trifluoroethyl)pyrimidin-4-amine,
6-Chloro-5-{4-[4-(dimethylamino)butoxy]-2,6-difluorophenyl}-2-pyrazin-2-yl-N-(2,2,2-trifluoroethyl)pyrimidin-4-amine,
6-Chloro-5-{2,6-difluoro-4-[3-(methylamino)propoxy]phenyl}-2-pyridin-2-yl-N-[2,2,2-trifluoro-1-methylethyl]pyrimidin-4-amine,
6-Chloro-5-{4-[3-(dimethylamino)propoxy]-2,6-difluorophenyl}-2-quinolin-2-yl-N-(2,2,2-trifluoroethyl)pyrimidin-4-amine,
6-Chloro-5-{4-[3-(dimethylamino)propoxy]-2,6-difluorophenyl}-2-(1H-imidazol-1-yl)-N-(2,2,2-trifluoroethyl)pyrimidin-4-amine,
6-Chloro-5-{2,6-difluoro-4-[3-(methylamino)propoxy]phenyl}-2-(1H-pyrazol-1-yl)-N-[2,2,2-trifluoro-1-methylethyl]pyrimidin-4-amine,
N-{3-[4-(4-Chloro-6-cycloheptyl-2-pyrazin-2-ylpyrimidin-5-yl)-3,5-difluorophenoxy]propyl}-N-methylamine,
6-Chloro-2-(1-methyl-1H-imidazol-2-yl)-N-(2,2,2-trifluoroethyl)-5-(2,4,6-trifluorophenyl)pyrimidin-4-amine,
6-Chloro-2-(1H-pyrrol-2-yl)-N-(2,2,2-trifluoroethyl)-5-(2,4,6-trifluorophenyl)pyrimidin-4-amine,
6-Chloro-2-(4-methylpyridin-2-yl)-N-(2,2,2-trifluoroethyl)-5-(2,4,6-trifluorophenyl)pyrimidin-4-amine,
6-Chloro-2-(5-nitropyridin-2-yl)-N-(2,2,2-trifluoroethyl)-5-(2,4,6-trifluorophenyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine.

Specifically preferred compounds of this invention according to formula (IIa) useful in a method of treating or inhibiting the growth of cancerous tumor cells and associated diseases in a mammal in need thereof which comprises administering an effective amount of a compound or pharmaceutically acceptable salt thereof selected from:
6-Chloro-2-pyrazin-2-yl-N-[(1S)-2,2,2-trifluoro-1-methylethyl]-5-(2,4,6-trifluorophenyl)pyrimidin-4-amine,
6-Chloro-2-pyridin-2-yl-N-[(1S)-2,2,2-trifluoro-1-methylethyl]-5-(2,4,6-trifluorophenyl)pyrimidin-4-amine,
6-Chloro-2-(1H-pyrazol-1-yl)-N-[(1S)-2,2,2-trifluoro-1-methylethyl]-5-(2,4,6-trifluorophenyl)pyrimidin-4-amine,
(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and
6-Chloro-5-{2,6-difluoro-4-[3-(methylamino)propoxy]phenyl}-2-(1H-pyrazol-1-yl)-N-[(1S)-2,2,2-trifluoro-1-methylethyl)pyrimidin-4-amine.

Specifically preferred compounds of this invention according to formula (IIb) useful in a method of treating or inhibiting the growth of cancerous tumor cells and associated diseases in a mammal in need thereof which comprises administering an effective amount of a compound or pharmaceutically acceptable salt thereof selected from:
6-Chloro-2-pyrazin-2-yl-N-[(1R)-2,2,2-trifluoro-1-methylethyl]-5-(2,4,6-trifluorophenyl)pyrimidin-4-amine,
6-Chloro-2-pyridin-2-yl-N-[(1R)-2,2,2-trifluoro-1-methylethyl]-5-(2,4,6-trifluorophenyl)pyrimidin-4-amine,
6-Chloro-2-(1H-pyrazol-1-yl)-N-[(1R)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and
6-Chloro-5-{2,6-difluoro-4-[3-(methylamino)propoxy]phenyl}-2-(1H-pyrazol-1-yl)-N-[(1R)-2,2,2-trifluoro-1-methylethyl)pyrimidin-4-amine.

The present invention provides a method of promoting tubulin polymerization in a tubulin containing system which comprises contacting said tubulin containing system with an effective amount of a compound of formula (II):

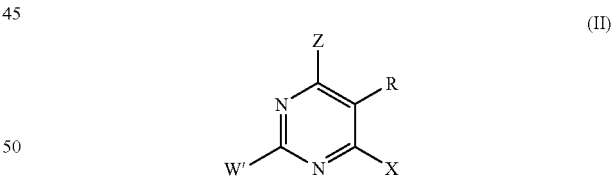

(II)

wherein:
Z is selected from:

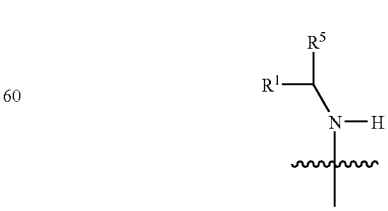

and $C_6$-$C_8$ cycloalkyl;

R is a moiety

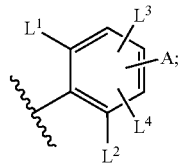

X is Cl or Br;
$L^1$, $L^2$, $L^3$ and $L^4$ are each independently H, F, Cl or Br;
A is H, F, Cl, Br, or $Y(CH_2)_nQ$;
Y is O, S, or —$NR^2$;
n is an integer of 2, 3, or 4;
Q is OH or —$NR^3R^4$;
$R^1$ is H or $C_1$-$C_3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;
W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;
$R^6$ is $C_1$-$C_3$ alkyl;
$R^7$ is $C_1$-$C_3$ alkyl;

and pharmaceutically acceptable salts thereof.

Also provided by this invention is a method of promoting tubulin polymerization in a tubulin containing system which comprises contacting said tubulin containing system with an effective amount of a compound of formula (IIa):

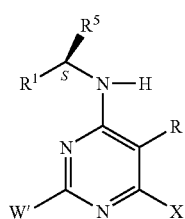

(IIa)

or pharmaceutically acceptable salts thereof.

A preferred embodiment of the present invention is to provide a method of promoting tubulin polymerization in a tubulin containing system which comprises contacting said tubulin containing system with an effective amount of a compound of formula (IIb):

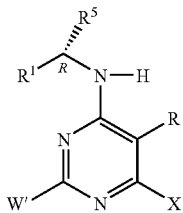

(IIb)

or pharmaceutically acceptable salts thereof.

Further preferred embodiment of the present invention is to provide a method of promoting tubulin polymerization in a tubulin containing system which comprises contacting said tubulin containing system with an effective amount of a compound according to formula (II) wherein R is a moiety

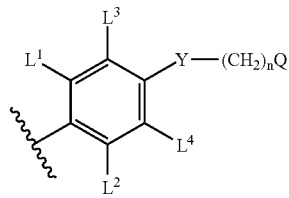

or pharmaceutically acceptable salts thereof.

A more preferred embodiment of the present invention is to provide a method of promoting tubulin polymerization in a tubulin containing system which comprises contacting said tubulin containing system with an effective amount of a compound according to formula (IIa) or pharmaceutically acceptable salts thereof wherein:
R is a moiety

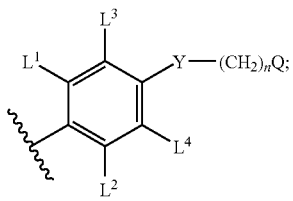

n=3;
Y is O;
Q is —$NR^3R^4$;
$R^1$ is H or methyl;
$R^5$ is $CF_3$;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^6$ is $C_1$-$C_3$ alkyl;
$R^7$ is $C_1$-$C_3$ alkyl;
$L^1$ is F;
$L^2$ is H or F;
$L^3$ is H;
$L^4$ is H;
X is Cl or Br;

or pharmaceutically acceptable salts thereof.

A more preferred embodiment of the present invention is to provide a method of promoting tubulin polymerization in a tubulin containing system which comprises contacting said tubulin containing system with an effective amount of a compound according to formula (IIb) including pharmaceutically acceptable salts thereof wherein:

R is

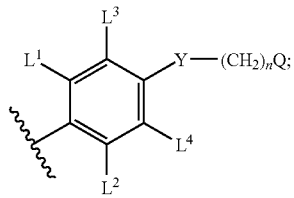

n=3;
Y is O;
Q is —NR³R⁴;
R¹ is H or methyl;
R⁵ is CF₃;
R³ and R⁴ are each independently H or C₁-C₃ alkyl; or R³ and R⁴ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R⁷;
R⁶ is C₁-C₃ alkyl;
R⁷ is C₁-C₃ alkyl;
L¹ is F;
L² is H or F;
L³ is H;
L⁴ is H;
X is Cl or Br;

or pharmaceutically acceptable salts thereof.

A more preferred embodiment of the present invention is to provide a method of promoting tubulin polymerization in a tubulin containing system which comprises contacting said tubulin containing system with an effective amount of a compound according to formula (IIa) or pharmaceutically acceptable salts thereof wherein:

R is a moiety

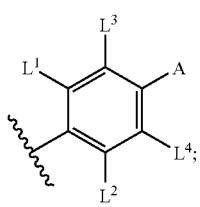

A is F;
R¹ is H or methyl;
R⁵ is CF₃;
R⁶ is C₁-C₃ alkyl;
L¹ is F;
L² is H or F;
L³ is H;
L⁴ is H;
X is Cl or Br;

or pharmaceutically acceptable salts thereof.

A more preferred embodiment of the present invention is to provide a method of promoting tubulin polymerization in a tubulin containing system which comprises contacting said tubulin containing system with an effective amount of a compound according to Formula (IIb) including pharmaceutically acceptable salts wherein:

R is a moiety

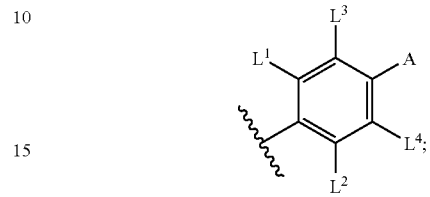

A is F;
R¹ is H or methyl;
R⁵ is CF₃;
R⁶ is C₁-C₃ alkyl;
L¹ is F;
L² is H or F;
L³ is H;
L⁴ is H;
X is Cl or Br;

or a pharmaceutically acceptable salt thereof.

Specifically preferred compounds of this invention useful in a method of promoting tubulin polymerization in a tubulin containing system which comprises contacting said tubulin containing system with an effective amount of a compound according to formula (II) or a pharmaceutically acceptable salt thereof selected from:

4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine,
6-Chloro-2-pyridin-4-yl-N-(2,2,2-trifluoroethyl)-5-(2,4,6-trifluorophenyl)pyrimidin-4-amine,
6-Chloro-2-pyridin-3-yl-N-(2,2,2-trifluoroethyl)-5-(2,4,6-trifluorophenyl)pyrimidin-4-amine,
6-Chloro-2-pyridin-2-yl-N-(2,2,2-trifluoroethyl)-5-(2,4,6-trifluorophenyl)pyrimidin-4-amine,
6-Chloro-2-pyridin-2-yl-N-[2,2,2-trifluoro-1-methylethyl]-5-(2,4,6-trifluorophenyl)pyrimidin-4-amine,
6-Chloro-2-quinolin-2-yl-N-(2,2,2-trifluoroethyl)-5-(2,4,6-trifluorophenyl)pyrimidin-4-amine,
6-Chloro-2-isoquinolin-1-yl-N-(2,2,2-trifluoroethyl)-5-(2,4,6-trifluorophenyl)pyrimidin-4-amine,
6-Chloro-2-isoquinolin-3-yl-N-(2,2,2-trifluoroethyl)-5-(2,4,6-trifluorophenyl)pyrimidin-4-amine,
6-Chloro-2-thien-2-yl-N-(2,2,2-trifluoroethyl)-5-(2,4,6-trifluorophenyl)pyrimidin-4-amine,
6-Chloro-2-(2-furyl)-N-(2,2,2-trifluoroethyl)-5-(2,4,6-trifluorophenyl)pyrimidin-4-amine,
6-Chloro-2-(1H-imidazol-1-yl)-N-(2,2,2-trifluoroethyl)-5-(2,4,6-trifluorophenyl)pyrimidin-4-amine,
6-Chloro-2-(1H-pyrazol-1-yl)-N-(2,2,2-trifluoroethyl)-5-(2,4,6-trifluorophenyl)pyrimidin-4-amine, 6-Chloro-2-(1H-pyrazol-1-yl)-N-[2,2,2-trifluoro-1-methylethyl)-5-(2,4,6-trifluorophenyl)pyrimidin-4-amine,
6-Chloro-2-(1H-pyrrol-1-yl)-N-(2,2,2-trifluoroethyl)-5-(2,4,6-trifluorophenyl)pyrimidin-4-amine,
4-Chloro-5-{4-[3-(dimethylamino)propoxy]-2,6-difluorophenyl}-6-[(2,2,2-trifluoroethyl)amino]pyrimidin-2-yl(methyl)cyanamide,
6-Chloro-5-{4-[3-(dimethylamino)propoxy]-2,6-difluorophenyl}-$N^2$-methyl-$N^4$-(2,2,2-trifluoroethyl)pyrimidine-2,4-diamine,
(4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
4-Chloro-5-{4-[2-(dimethylamino)ethoxy]-2,6-difluorophenyl}-6-[(2,2,2-trifluoroethyl)amino]pyrimidin-2-yl(methyl)cyanamide,
{4-Chloro-5-{4-[4-(dimethylamino)butoxy]-2,6-difluorophenyl}-6-[(2,2,2-trifluoroethyl)amino]pyrimidin-2-yl}methylcyanamide,
6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
6-Chloro-5-{4-[3-(dimethylamino)propoxy]-2,6-difluorophenyl}-2-pyrazin-2-yl-N-(2,2,2-trifluoroethyl)pyrimidin-4-amine,
6-Chloro-5-{4-[3-(dimethylamino)propoxy]-2,6-difluorophenyl}-N-(2,2,2-trifluoroethyl)-2,2'-bipyrimidin-4-amine,
6-Chloro-5-{4-[2-(dimethylamino)ethoxy]-2,6-difluorophenyl}-2-pyrazin-2-yl-N-(2,2,2-trifluoroethyl)pyrimidin-4-amine,
6-Chloro-5-{4-[4-(dimethylamino)butoxy]-2,6-difluorophenyl}-2-pyrazin-2-yl-N-(2,2,2-trifluoroethyl)pyrimidin-4-amine,
6-Chloro-5-{2,6-difluoro-4-[3-(methylamino)propoxy]phenyl}-2-pyridin-2-yl-N-[2,2,2-trifluoro-1-methylethyl]pyrimidin-4-amine,
6-Chloro-5-{4-[3-(dimethylamino)propoxy]-2,6-difluorophenyl}-2-quinolin-2-yl-N-(2,2,2-trifluoroethyl)pyrimidin-4-amine,
6-Chloro-5-{4-[3-(dimethylamino)propoxy]-2,6-difluorophenyl}-2-(1H-imidazol-1-yl)-N-(2,2,2-trifluoroethyl)pyrimidin-4-amine,
6-Chloro-5-{2,6-difluoro-4-[3-(methylamino)propoxy]phenyl}-2-(1H-pyrazol-1-yl)-N-[2,2,2-trifluoro-1-methylethyl)pyrimidin-4-amine,
N-{3-[4-(4-Chloro-6-cycloheptyl-2-pyrazin-2-ylpyrimidin-5-yl)-3,5-difluorophenoxy]propyl}-N-methylamine,
6-Chloro-2-(1-methyl-1H-imidazol-2-yl)-N-(2,2,2-trifluoroethyl)-5-(2,4,6-trifluorophenyl)pyrimidin-4-amine,
6-Chloro-2-(1H-pyrrol-2-yl)-N-(2,2,2-trifluoroethyl)-5-(2,4,6-trifluorophenyl)pyrimidin-4-amine,
6-Chloro-2-(4-methylpyridin-2-yl)-N-(2,2,2-trifluoroethyl)-5-(2,4,6-trifluorophenyl)pyrimidin-4-amine,
6-Chloro-2-(5-nitropyridin-2-yl)-N-(2,2,2-trifluoroethyl)-5-(2,4,6-trifluorophenyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine.

Specifically preferred compounds of this invention useful in a method of promoting tubulin polymerization in a tubulin containing system which comprises contacting said tubulin containing system with an effective amount of a compound according to formula (IIa) or pharmaceutically acceptable salts thereof selected from:

6-Chloro-2-pyrazin-2-yl-N-[(1S)-2,2,2-trifluoro-1-methylethyl]-5-(2,4,6-trifluorophenyl)pyrimidin-4-amine,
6-Chloro-2-pyridin-2-yl-N-[(1S)-2,2,2-trifluoro-1-methylethyl]-5-(2,4,6-trifluorophenyl)pyrimidin-4-amine,
6-Chloro-2-(1H-pyrazol-1-yl)-N-[(1S)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and
6-Chloro-5-{2,6-difluoro-4-[3-(methylamino)propoxy]phenyl}-2-(1H-pyrazol-1-yl)-N-[(1S)-2,2,2-trifluoro-1-methylethyl)pyrimidin-4-amine.

Specifically preferred compounds of this invention useful in a method of promoting tubulin polymerization in a tubulin containing system which comprises contacting said tubulin containing system with an effective amount of a compound according to formula (IIb) or pharmaceutically acceptable salts thereof selected from:

6-Chloro-2-pyrazin-2-yl-N-[(1R)-2,2,2-trifluoro-1-methylethyl]-5-(2,4,6-trifluorophenyl)pyrimidin-4-amine,
6-Chloro-2-pyridin-2-yl-N-[(1R)-2,2,2-trifluoro-1-methylethyl]-5-(2,4,6-trifluorophenyl)pyrimidin-4-amine,
6-Chloro-2-(1H-pyrazol-1-yl)-N-[(1R)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and
6-Chloro-5-{2,6-difluoro-4-[3-(methylamino)propoxy]phenyl}-2-(1H-pyrazol-1-yl)-N-[(1R)-2,2,2-trifluoro-1-methylethyl)pyrimidin-4-amine.

Further provided by the present invention is a method of stabilizing microtubules in a tubulin containing system by contacting said tubulin containing system with an effective amount of a compound of formula (II) or a pharmaceutically acceptable salt thereof

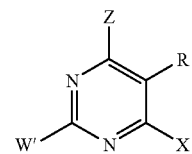

(II)

wherein:
Z is selected from:

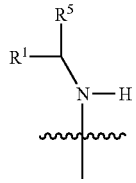

and $C_6$-$C_8$ cycloalkyl;
R is a moiety

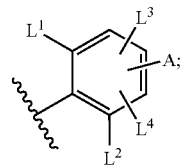

X is Cl or Br;
$L^1$, $L^2$, $L^3$ and $L^4$ are each independently H, F, Cl or Br;
A is H, F, Cl, Br, or $Y(CH_2)_nQ$;
Y is O, S, or —$NR^2$;
n is an integer of 2, 3, or 4;
Q is OH or —$NR^3R^4$;
$R^1$ is H or $C_1$-$C_3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;
W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;
$R^6$ is $C_1$-$C_3$ alkyl;
$R^7$ is $C_1$-$C_3$ alkyl;

and pharmaceutically acceptable salts thereof.

A preferred embodiment of the present invention is to provide a method of stabilizing microtubules in a tubulin containing system by contacting said tubulin containing system with an effective amount of a compound of formula (IIa) or a pharmaceutically acceptable salt thereof

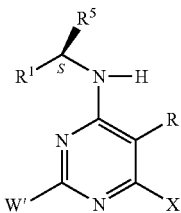

(IIa)

or pharmaceutically acceptable salts thereof.

A preferred embodiment of the present invention is to provide a method of stabilizing microtubules in a tubulin containing system by contacting said tubulin containing system with an effective amount of a compound of formula (IIb)

(IIb)

or pharmaceutically acceptable salts thereof.

Further preferred embodiment of the present invention is to provide a method of stabilizing microtubules in a tubulin containing system by contacting said tubulin containing system with an effective amount of a compound of formula (II) wherein R is a moiety

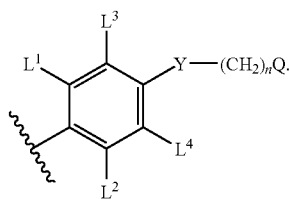

A more preferred embodiment of the present invention is to provide a method of stabilizing microtubules in a tubulin containing system by contacting said tubulin containing system with an effective amount of a compound of formula (IIa) wherein:
R is a moiety

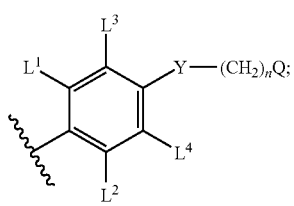

n=3;
Y is O;
Q is —$NR^3R^4$;

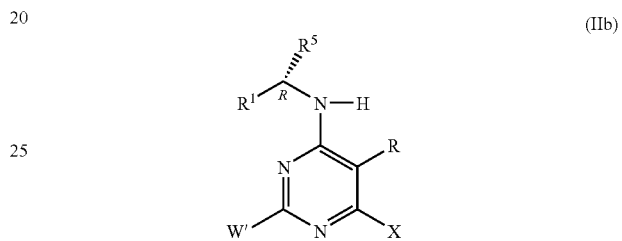

$R^1$ is H or methyl;
$R^5$ is $CF_3$;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^6$ is $C_1$-$C_3$ alkyl;
$R^7$ is $C_1$-$C_3$ alkyl;
$L^1$ is F;
$L^2$ is H or F;
$L^3$ is H;
$L^4$ is H;
X is Cl or Br;

or pharmaceutically acceptable salts thereof.

A more preferred embodiment of the present invention is to provide a method of stabilizing microtubules in a tubulin containing system by contacting said tubulin containing system with an effective amount of a compound of formula (IIb) wherein:

R is a moiety

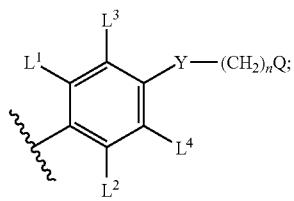

n=3;
Y is O;
Q is $-NR^3R^4$;
$R^1$ is H or methyl;
$R^5$ is $CF_3$;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^6$ is $C_1$-$C_3$ alkyl;
$R^7$ is $C_1$-$C_3$ alkyl;
$L^1$ is F;
$L^2$ is H or F;
$L^3$ is H;
$L^4$ is H;
X is Cl or Br;

or pharmaceutically acceptable salts thereof.

A more preferred embodiment of the present invention is to provide a method of stabilizing microtubules in a tubulin containing system by contacting said tubulin containing system with an effective amount of a compound of formula (IIa) wherein:

R is a moiety

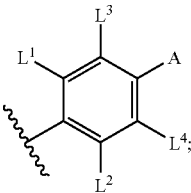

A is F;
$R^1$ is H or methyl;
$R^5$ is $CF_3$;
$R^6$ is $C_1$-$C_3$ alkyl;
$L^1$ is F;
$L^2$ is H or F;
$L^3$ is H;
$L^4$ is H;
X is Cl or Br;

or pharmaceutically acceptable salts thereof.

A more preferred embodiment of the present invention is to provide a method of stabilizing microtubules in a tubulin containing system by contacting said tubulin containing system with an effective amount of a compound of formula (IIb) wherein:

R is a moiety

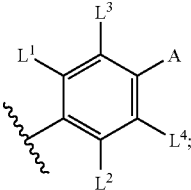

A is F;
$R^1$ is H or methyl;
$R^5$ is $CF_3$;
$R^6$ is $C_1$-$C_3$ alkyl;
$L^1$ is F;
$L^2$ is H or F;
$L^3$ is H;
$L^4$ is H;
X is Cl or Br;

or pharmaceutically acceptable salts thereof.

Specifically preferred compounds of this invention useful in a method of stabilizing microtubules in a tubulin containing system by contacting said tubulin containing system with an effective amount of a compound of formula (II) are the following compounds or a pharmaceutically acceptable salt thereof:
4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine,
6-Chloro-2-pyridin-4-yl-N-(2,2,2-trifluoroethyl)-5-(2,4,6-trifluorophenyl)pyrimidin-4-amine, 6-Chloro-2-pyridin-3-yl-N-(2,2,2-trifluoroethyl)-5-(2,4,6-trifluorophenyl)pyrimidin-4-amine,
6-Chloro-2-pyridin-2-yl-N-(2,2,2-trifluoroethyl)-5-(2,4,6-trifluorophenyl)pyrimidin-4-amine,
6-Chloro-2-pyridin-2-yl-N-[2,2,2-trifluoro-1-methylethyl]-5-(2,4,6-trifluorophenyl)pyrimidin-4-amine,
6-Chloro-2-quinolin-2-yl-N-(2,2,2-trifluoroethyl)-5-(2,4,6-trifluorophenyl)pyrimidin-4-amine,
6-Chloro-2-isoquinolin-1-yl-N-(2,2,2-trifluoroethyl)-5-(2,4,6-trifluorophenyl)pyrimidin-4-amine,
6-Chloro-2-isoquinolin-3-yl-N-(2,2,2-trifluoroethyl)-5-(2,4,6-trifluorophenyl)pyrimidin-4-amine,
6-Chloro-2-thien-2-yl-N-(2,2,2-trifluoroethyl)-5-(2,4,6-trifluorophenyl)pyrimidin-4-amine,
6-Chloro-2-(2-furyl)-N-(2,2,2-trifluoroethyl)-5-(2,4,6-trifluorophenyl)pyrimidin-4-amine,
6-Chloro-2-(1H-imidazol-1-yl)-N-(2,2,2-trifluoroethyl)-5-(2,4,6-trifluorophenyl)pyrimidin-4-amine,
6-Chloro-2-(1H-pyrazol-1-yl)-N-(2,2,2-trifluoroethyl)-5-(2,4,6-trifluorophenyl)pyrimidin-4-amine,
6-Chloro-2-(1H-pyrazol-1-yl)-N-[2,2,2-trifluoro-1-methylethyl]-5-(2,4,6-trifluorophenyl)pyrimidin-4-amine,
6-Chloro-2-(1H-pyrrol-1-yl)-N-(2,2,2-trifluoroethyl)-5-(2,4,6-trifluorophenyl)pyrimidin-4-amine,
4-Chloro-5-{4-[3-(dimethylamino)propoxy]-2,6-difluorophenyl}-6-[(2,2,2-trifluoroethyl)amino]pyrimidin-2-yl(methyl)cyanamide,
6-Chloro-5-{4-[3-(dimethylamino)propoxy]-2,6-difluorophenyl}-$N^2$-methyl-$N^4$-(2,2,2-trifluoroethyl)pyrimidine-2,4-diamine,
(4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
4-Chloro-5-{4-[2-(dimethylamino)ethoxy]-2,6-difluorophenyl}-6-[(2,2,2-trifluoroethyl)amino]pyrimidin-2-yl(methyl)cyanamide,
{4-Chloro-5-{4-[4-(dimethylamino)butoxy]-2,6-difluorophenyl}-6-[(2,2,2-trifluoroethyl)amino]pyrimidin-2-yl}methylcyanamide,
6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
6-Chloro-5-{4-[3-(dimethylamino)propoxy]-2,6-difluorophenyl}-2-pyrazin-2-yl-N-(2,2,2-trifluoroethyl)pyrimidin-4-amine,
6-Chloro-5-{4-[3-(dimethylamino)propoxy]-2,6-difluorophenyl}-N-(2,2,2-trifluoroethyl)-2,2'-bipyrimidin-4-amine,
6-Chloro-5-{4-[2-(dimethylamino)ethoxy]-2,6-difluorophenyl}-2-pyrazin-2-yl-N-(2,2,2-trifluoroethyl)pyrimidin-4-amine,
6-Chloro-5-{4-[4-(dimethylamino)butoxy]-2,6-difluorophenyl}-2-pyrazin-2-yl-N-(2,2,2-trifluoroethyl)pyrimidin-4-amine,
6-Chloro-5-{2,6-difluoro-4-[3-(methylamino)propoxy]phenyl}-2-pyridin-2-yl-N-[2,2,2-trifluoro-1-methylethyl]pyrimidin-4-amine,
6-Chloro-5-{4-[3-(dimethylamino)propoxy]-2,6-difluorophenyl}-2-quinolin-2-yl-N-(2,2,2-trifluoroethyl)pyrimidin-4-amine,
6-Chloro-5-{4-[3-(dimethylamino)propoxy]-2,6-difluorophenyl}-2-(H-imidazol-1-yl)-N-(2,2,2-trifluoroethyl)pyrimidin-4-amine,
6-Chloro-5-{2,6-difluoro-4-[3-(dimethylamino)propoxy]phenyl}-2-(1H-pyrazol-1-yl)-N-[2,2,2-trifluoro-1-methylethyl)pyrimidin-4-amine,
N-{3-[4-(4-Chloro-6-cycloheptyl-2-pyrazin-2-ylpyrimidin-5-yl)-3,5-difluorophenoxy]propyl}-N-methylamine,
6-Chloro-2-(1-methyl-1H-imidazol-2-yl)-N-(2,2,2-trifluoroethyl)-5-(2,4,6-trifluorophenyl)pyrimidin-4-amine,
6-Chloro-2-(1H-pyrrol-2-yl)-N-(2,2,2-trifluoroethyl)-5-(2,4,6-trifluorophenyl)pyrimidin-4-amine,
6-Chloro-2-(4-methylpyridin-2-yl)-N-(2,2,2-trifluoroethyl)-5-(2,4,6-trifluorophenyl)pyrimidin-4-amine,
6-Chloro-2-(5-nitropyridin-2-yl)-N-(2,2,2-trifluoroethyl)-5-(2,4,6-trifluorophenyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine.

A more preferred embodiment of this invention useful in a method of stabilizing microtubules in a tubulin containing system by contacting said tubulin containing system with an effective amount of a compound of formula (IIa) are the following compounds or a pharmaceutically acceptable salt thereof:

6-Chloro-2-pyrazin-2-yl-N-[(1S)-2,2,2-trifluoro-1-methylethyl]-5-(2,4,6-trifluorophenyl)pyrimidin-4-amine,
6-Chloro-2-pyridin-2-yl-N-[(1S)-2,2,2-trifluoro-1-methylethyl]-5-(2,4,6-trifluorophenyl)pyrimidin-4-amine,
6-Chloro-2-(1H-pyrazol-1-yl)-N-[(1S)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and
6-Chloro-5-{2,6-difluoro-4-[3-(dimethylamino)propoxy]phenyl}-2-(1H-pyrazol-1-yl)-N-[(1S)-2,2,2-trifluoro-1-methylethyl)pyrimidin-4-amine.

A more preferred embodiment of this invention useful in a method of stabilizing microtubules in a tubulin containing system by contacting said tubulin containing system with an effective amount of a compound of formula (IIb) are the following compounds or a pharmaceutically acceptable salt thereof:

6-Chloro-2-pyrazin-2-yl-N-[(1R)-2,2,2-trifluoro-1-methylethyl]-5-(2,4,6-trifluorophenyl)pyrimidin-4-amine,
6-Chloro-2-pyridin-2-yl-N-[(1R)-2,2,2-trifluoro-1-methylethyl]-5-(2,4,6-trifluorophenyl)pyrimidin-4-amine,
6-Chloro-2-(1H-pyrazol-1-yl)-N-[(1R)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and
6-Chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine.

The present invention also provides a method for the treatment or prevention of tumors that express multiple drug resistance (MDR) or are resistant because of MDR in a mammal in need thereof which method comprises administering to said mammal an effective amount of a compound of formula (II):

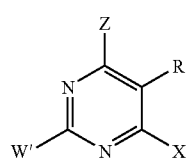
(II)

wherein:
Z is selected from:

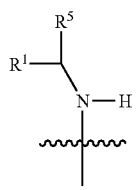

and $C_6$-$C_8$ cycloalkyl;
R is a moiety of the group

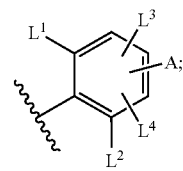

X is Cl or Br;
$L^1$, $L^2$, $L^3$ and $L^4$ are each independently H, F, Cl or Br;
A is H, F, Cl, Br, or $Y(CH_2)_nQ$;
Y is O, S, or —$NR^2$;
n is an integer of 2, 3, or 4;
Q is OH or —$NR^3R^4$;
$R^1$ is H or $C_1$-$C_3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;
W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;
$R^6$ is $C_1$-$C_3$ alkyl;
$R^7$ is $C_1$-$C_3$ alkyl;

and pharmaceutically acceptable salts thereof.
A preferred embodiment of the present invention is to provide a method for the treatment or prevention of tumors that express multiple drug resistance (MDR) or are resistant because of MDR in a mammal in need thereof which method comprises administering to said mammal an effective amount of a compound according to Formula (IIa):

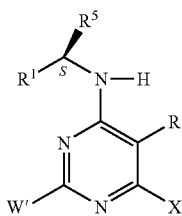
(IIa)

or pharmaceutically acceptable salts thereof.
A preferred embodiment of the present invention is to provide a method for the treatment or prevention of tumors that express multiple drug resistance (MDR) or are resistant because of MDR in a mammal in need thereof which method comprises administering to said mammal an effective amount of a compound according to Formula (IIb):

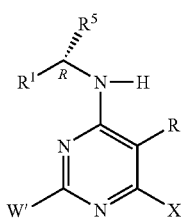
(IIb)

or pharmaceutically acceptable salts thereof.
Further preferred are compounds of formula (II) wherein R is a moiety

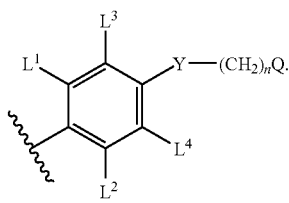

or pharmaceutically acceptable salts thereof.
A more preferred embodiment of the present invention is to provide a method for the treatment or prevention of tumors that express multiple drug resistance (MDR) or are resistant because of MDR in a mammal in need thereof which method comprises administering to said mammal an effective amount of a compound according to formula (IIa) wherein:
R is

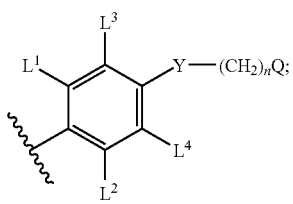

n=3;
Y is O;
Q is —$NR^3R^4$;

$R^1$ is H or methyl;
$R^5$ is $CF_3$;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^6$ is $C_1$-$C_3$ alkyl;
$R^7$ is $C_1$-$C_3$ alkyl;
$L^1$ is F;
$L^2$ is H or F;
$L^3$ is H;
$L^4$ is H;
X is Cl or Br;
or pharmaceutically acceptable salts thereof.

A more preferred embodiment of the present invention is to provide a method for the treatment or prevention of tumors that express multiple drug resistance (MDR) or are resistant because of MDR in a mammal in need thereof which method comprises administering to said mammal an effective amount of a compound according to formula (IIb) wherein:
R is

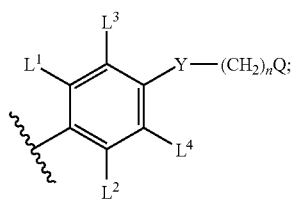

n=3;
Y is O;
Q is —$NR^3R^4$;
$R^1$ is H or methyl;
$R^5$ is $CF_3$;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^6$ is $C_1$-$C_3$ alkyl;
$R^7$ is $C_1$-$C_3$ alkyl;
$L^1$ is F;
$L^2$ is H or F;
$L^3$ is H;
$L^4$ is H;
X is Cl or Br;
or pharmaceutically acceptable salts thereof.

A more preferred embodiment of the present invention is to provide a method for the treatment or prevention of tumors that express multiple drug resistance (MDR) or are resistant because of MDR in a mammal in need thereof which method comprises administering to said mammal an effective amount of a compound according to Formula (IIa) wherein:
R is

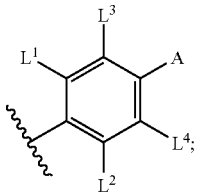

A is F;
$R^1$ is H or methyl;
$R^5$ is $CF_3$;
$R^6$ is $C_1$-$C_3$ alkyl;
$L^1$ is F;
$L^2$ is H or F;
$L^3$ is H;
$L^4$ is H;
X is Cl or Br;
or pharmaceutically acceptable salts thereof.

A more preferred embodiment of the present invention is to provide a method for the treatment or prevention of tumors that express multiple drug resistance (MDR) or are resistant because of MDR in a mammal in need thereof which method comprises administering to said mammal an effective amount of a compound according to Formula (IIb) wherein:
R is

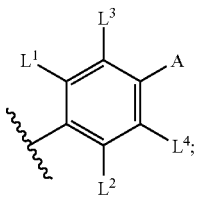

A is F;
$R^1$ is H or methyl;
$R^5$ is $CF_3$;
$R^6$ is $C_1$-$C_3$ alkyl;
$L^1$ is F;
$L^2$ is H or F;
$L^3$ is H;
$L^4$ is H;
X is Cl or Br;
or pharmaceutically acceptable salts thereof.

Specifically preferred compounds of this invention according to Formula (II) are the following compounds or pharmaceutically acceptable salts thereof useful in a method for the treatment or prevention of tumors that express multiple drug resistance (MDR) or are resistant because of MDR in a mammal in need thereof are the following compounds or a pharmaceutically acceptable salt thereof:
4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine, 6-Chloro-2-pyridin-4-yl-N-(2,2,2-trifluoroethyl)-5-(2,4,6-trifluorophenyl)pyrimidin-4-amine, 6-Chloro-2-pyridin-3-yl-N-(2,2,2-trifluoroethyl)-5-(2,4,6-trifluorophenyl)pyrimidin-4-amine, 6-Chloro-2-pyridin-2-yl-N-(2,2,2-trifluoroethyl)-5-(2,4,6-trifluorophenyl)pyrimidin-4-amine, 6-Chloro-2-pyridin-2-yl-N-[2,2,2-trifluoro-1-methylethyl]-5-(2,4,6-trifluorophenyl)pyrimidin-4-amine, 6-Chloro-2-quinolin-2-yl-N-(2,2,2-trifluoroethyl)-5-(2,4,6-trifluorophenyl)pyrimidin-4-amine, 6-Chloro-2-isoquinolin-1-yl-N-(2,2,2-trifluoroethyl)-5-(2,4,6-trifluorophenyl)pyrimidin-4-amine, 6-Chloro-2-isoquinolin-3-yl-N-(2,2,2-trifluoroethyl)-5-(2,4,6-trifluorophenyl)pyrimidin-4-amine, 6-Chloro-2-thien-2-yl-N-(2,2,2-trifluoroethyl)-5-(2,4,6-trifluorophenyl)pyrimidin-4-amine, 6-Chloro-2-(2-furyl)-N-(2,2,2-trifluoroethyl)-5-(2,4,6-trifluorophenyl)pyrimidin-4-amine, 6-Chloro-2-(1H-imidazol-1-yl)-N-(2,2,2-trifluoroethyl)-5-(2,4,6-trifluorophenyl)pyrimidin-4-amine, 6-Chloro-2-(1H-pyrazol-1-yl)-N-(2,2,2-trifluoroethyl)-5-(2,4,6-trifluorophenyl)pyrimidin-4-amine, 6-Chloro-2-(1H-pyrazol-1-yl)-N-[2,2,2-trifluoro-1-methylethyl]-5-(2,4,6-trifluorophenyl)pyrimidin-4-amine, 6-Chloro-2-(1H-pyrrol-1-yl)-N-(2,2,2-trifluoroethyl)-5-(2,4,6-trifluorophenyl)pyrimidin-4-amine, 4-Chloro-5-{4-[3-(dimethylamino)propoxy]-2,6-difluorophenyl}-6-[(2,2,2-trifluoroethyl)amino]pyrimidin-2-yl(methyl)cyanamide, 6-Chloro-5-{4-[3-(dimethylamino)propoxy]-2,6-difluorophenyl}-N²-methyl-N⁴-(2,2,2-trifluoroethyl)pyrimidine-2,4-diamine, (4-Chloro-5-{4-[3-(dimethylamino)propoxy]-2,6-difluorophenyl}-6-{[2,2,2-trifluoro-1-methylethyl]amino}pyrimidin-2-yl)methylcyanamide, 4-Chloro-5-{4-[2-(dimethylamino)ethoxy]-2,6-difluorophenyl}-6-[(2,2,2-trifluoroethyl)amino]pyrimidin-2-yl(methyl)cyanamide, {4-Chloro-5-{4-[4-(dimethylamino)butoxy]-2,6-difluorophenyl}-6-[(2,2,2-trifluoroethyl)amino]pyrimidin-2-yl}methylcyanamide, 6-Chloro-5-{2,6-difluoro-4-[3-(methylamino)propoxy]phenyl}-2-pyrazin-2-yl-N-[2,2,2-trifluoro-1-methylethyl]pyrimidin-4-amine, 6-Chloro-5-{4-[3-(dimethylamino)propoxy]-2,6-difluorophenyl}-2-pyrazin-2-yl-N-(2,2,2-trifluoroethyl)pyrimidin-4-amine, 6-Chloro-5-{4-[3-(dimethylamino)propoxy]-2,6-difluorophenyl}-N-(2,2,2-trifluoroethyl)-2,2'-bipyrimidin-4-amine, 6-Chloro-5-{4-[2-(dimethylamino)ethoxy]-2,6-difluorophenyl}-2-pyrazin-2-yl-N-(2,2,2-trifluoroethyl)pyrimidin-4-amine, 6-Chloro-5-{4-[4-(dimethylamino)butoxy]-2,6-difluorophenyl}-2-pyrazin-2-yl-N-(2,2,2-trifluoroethyl)pyrimidin-4-amine, 6-Chloro-5-{2,6-difluoro-4-[3-(methylamino)propoxy]phenyl}-2-pyridin-2-yl-N-[2,2,2-trifluoro-1-methylethyl]pyrimidin-4-amine, 6-Chloro-5-{4-[3-(dimethylamino)propoxy]-2,6-difluorophenyl}-2-quinolin-2-yl-N-(2,2,2-trifluoroethyl)pyrimidin-4-amine, 6-Chloro-5-{4-[3-(dimethylamino)propoxy]-2,6-difluorophenyl}-2-(1H-imidazol-1-yl)-N-(2,2,2-trifluoroethyl)pyrimidin-4-amine, 6-Chloro-5-{2,6-difluoro-4-[3-(dimethylamino)propoxy]phenyl}-2-(1H-pyrazol-1-yl)-N-[2,2,2-trifluoro-1-methylethyl]pyrimidin-4-amine, N-{3-[4-(4-Chloro-6-cycloheptyl-2-pyrazin-2-ylpyrimidin-5-yl)-3,5-difluorophenoxy]propyl}-N-methylamine, 6-Chloro-2-(1-methyl-1H-imidazol-2-yl)-N-(2,2,2-trifluoroethyl)-5-(2,4,6-trifluorophenyl)pyrimidin-4-amine, 6-Chloro-2-(1H-pyrrol-2-yl)-N-(2,2,2-trifluoroethyl)-5-(2,4,6-trifluorophenyl)pyrimidin-4-amine, 6-Chloro-2-(4-methylpyridin-2-yl)-N-(2,2,2-trifluoroethyl)-5-(2,4,6-trifluorophenyl)pyrimidin-4-amine, 6-Chloro-2-(5-nitropyridin-2-yl)-N-(2,2,2-trifluoroethyl)-5-(2,4,6-trifluorophenyl)pyrimidin-4-amine and 2-(5-Azidopyridin-2-yl)-6-chloro-5-{4-[3-(dimethylamino)propoxy]-2,6-difluorophenyl}-N-(2,2,2-trifluoroethyl)pyrimidin-4-amine.

Specifically preferred compounds of this invention according to Formula (IIa) are the following compounds or pharmaceutically acceptable salts thereof useful in a method for the treatment or prevention of tumors that express multiple drug resistance (MDR) or are resistant because of MDR in a mammal in need thereof are the following compounds or a pharmaceutically acceptable salt thereof:

6-Chloro-2-pyrazin-2-yl-N-[(1S)-2,2,2-trifluoro-1-methylethyl]-5-(2,4,6-trifluorophenyl)pyrimidin-4-amine, 6-Chloro-2-pyridin-2-yl-N-[(1S)-2,2,2-trifluoro-1-methylethyl]-5-(2,4,6-trifluorophenyl)pyrimidin-4-amine, 6-Chloro-2-(1H-pyrazol-1-yl)-N-[(1S)-2,2,2-trifluoro-1-methylethyl)-5-(2,4,6-trifluorophenyl)pyrimidin-4-amine, (4-Chloro-5-{4-[3-(dimethylamino)propoxy]-2,6-difluorophenyl}-6-{[(S)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and 6-Chloro-5-{2,6-difluoro-4-[3-(methylamino)propoxy]phenyl}-2-(1H-pyrazol-1-yl)-N-[(1S)-2,2,2-trifluoro-1-methylethyl)pyrimidin-4-amine.

Specifically preferred compounds of this invention according to Formula (IIb) are the following compounds or pharmaceutically acceptable salts thereof useful in a method for the treatment or prevention of tumors that express multiple drug resistance (MDR) or are resistant because of MDR in a mammal in need thereof are the following compounds or a pharmaceutically acceptable salt thereof:

6-Chloro-2-pyrazin-2-yl-N-[(1R)-2,2,2-trifluoro-1-methylethyl]-5-(2,4,6-trifluorophenyl)pyrimidin-4-amine, 6-Chloro-2-pyridin-2-yl-N-[(1R)-2,2,2-trifluoro-1-methylethyl]-5-(2,4,6-trifluorophenyl)pyrimidin-4-amine, 6-Chloro-2-(1H-pyrazol-1-yl)-N-[(1R)-2,2,2-trifluoro-1-methylethyl)-5-(2,4,6-trifluorophenyl)pyrimidin-4-amine, (4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and 6-Chloro-5-{2,6-difluoro-4-[3-(methylamino)propoxy]phenyl}-2-(1H-pyrazol-1-yl)-N-[(1R)-2,2,2-trifluoro-1-methylethyl)pyrimidin-4-amine.

DETAILED DESCRIPTION OF THE INVENTION

The compounds of this invention may be prepared from: (a) commercially available starting materials (b) known starting materials which may be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps. Appropriate consideration must be made as to the protection of reactive functional groups to prevent undesired side reactions.

Substituents on the starting materials may be incompatible with some of the reaction conditions. Such restrictions to the substituents which are compatible with the reaction conditions will be apparent to one skilled in the art. Reactions were run under inert atmospheres where appropriate.

The preparation of the compounds of this invention encompassed by Formulae (I) and (II) wherein
Z is

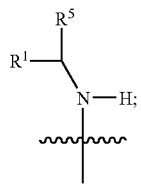

W' is —NHR$^6$ or —N(CN)R$^6$ can be prepared by a process shown in Scheme I, which comprises treating a compound of Formula (III) in which R$^5$, R$^1$, L$^1$, L$^2$, L$^3$, L$^4$, A and X are as hereinbefore defined, with an alkylating agent R$^6$-LG (IV), in which LG is a halo group or a moiety —OSO$_2$R$^5$, and R$^6$ is as hereinbefore defined. Compounds of Formula (V) are treated with a strong base which includes an alkali metal hydroxide, alkali metal carbonate and alkali hydride, e.g., sodium hydride, in the presence of an aprotic solvent which includes dimethylsulfoxide, dimethylformamide and the like to yield cyano compounds of Formula (II). Treatment of a cyano compound of Formula (II) when A is a leaving group, in particular a fluorine atom, with a compound of Formula (VI) in which Y, n and Q are as hereinbefore defined, in the presence of a strong base which includes alkali metal hydroxide, alkali metal carbonate and alkali hydride, e.g., sodium hydride, in the presence of an aprotic solvent which includes dimethylsulfoxide, dimethylformamide and the like gives Formula (I). The reaction is suitably carried out at a temperature in the range from about 0° C. to about 100° C.

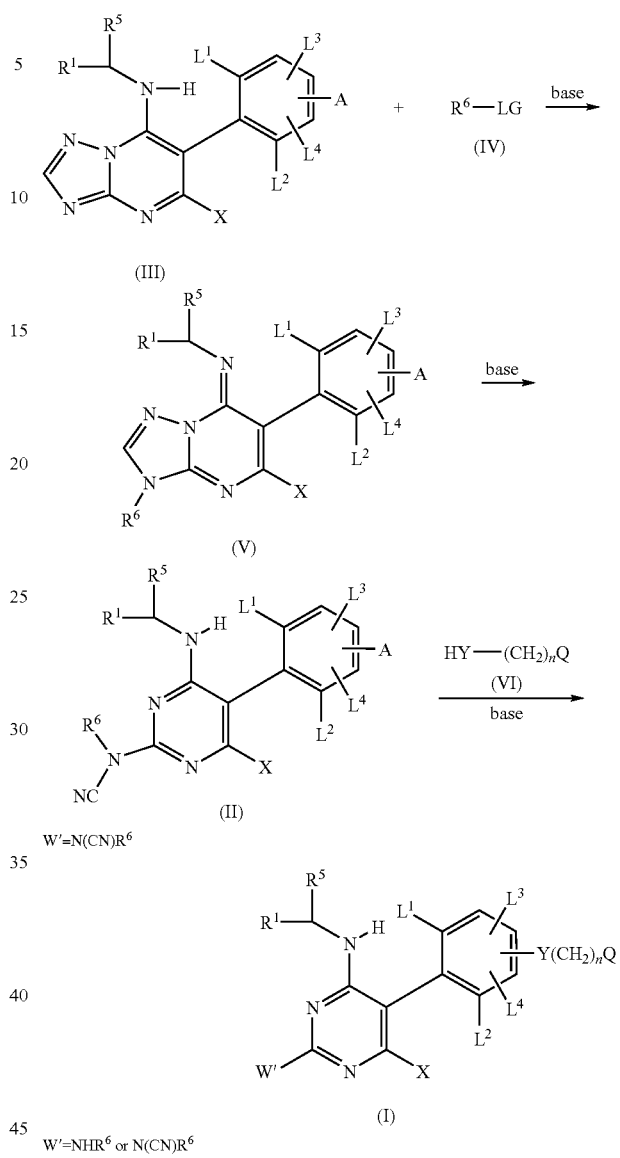

Scheme I

The preparation of the compounds of this invention encompassed by Formula (I) wherein Z is

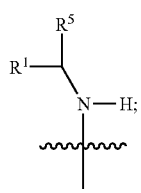

Y is O, S, or —NR$^2$ and
W' is aryl or heteroaryl as hereinbefore defined, can be prepared by a process shown in Scheme II, which comprises treating a compound of the Formula (II) when A is a leaving group, in particular a fluorine atom with a compound of Formula (VI) in which Y, n and Q are as hereinbefore defined, in the presence of a strong base which includes an alkali metal hydroxide, alkali metal carbonate and alkali hydride, e.g., sodium hydride, in the presence of an aprotic solvent, which includes dimethylsulfoxide, dimethylformamide, and the like. The reaction is suitably carried out at a temperature in the range from about 0° C. to about 100° C.

Scheme II

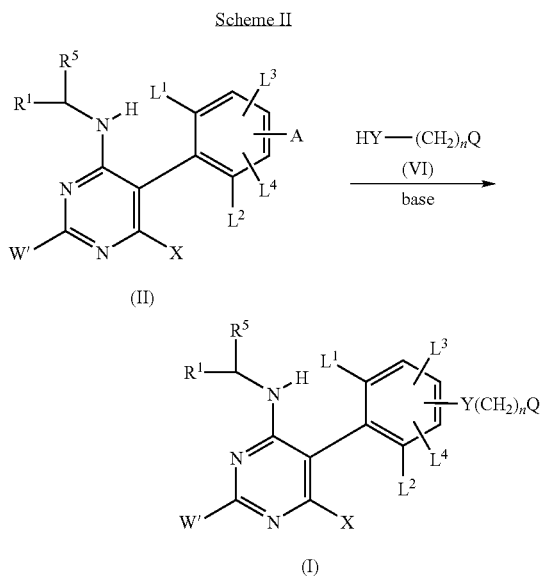

W' = aryl and heteroaryl

A compound of Formula (II) wherein Z is the moiety

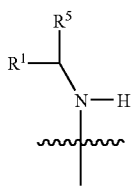

W' is aryl or heteroaryl as hereinbefore defined can be prepared as shown in Scheme III. Treating diester (VIII, U.S. Pat. No. 6,156,925) with carboxamidine (VII) in the presence of a tertiary amine base, such as tributylamine, at a temperature up to 190° C. provides compound (IX). Halogenation with halogenating agents $POX_3$, $PX_3$ or $PX_5$, such as phosphorous oxychloride or phosphorous oxybromide gives compound (X). Replacement of one of the halogens with excess amount of an amine (XI) in a suitable solvent, such as methylene chloride, dimethylsulfoxide or dimethylformamide, provides compound (II).

Scheme III

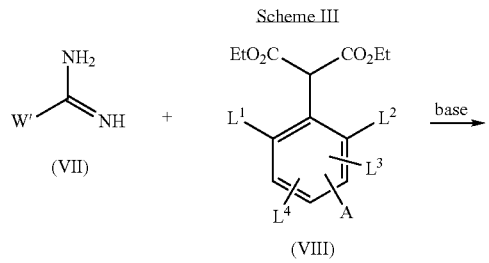

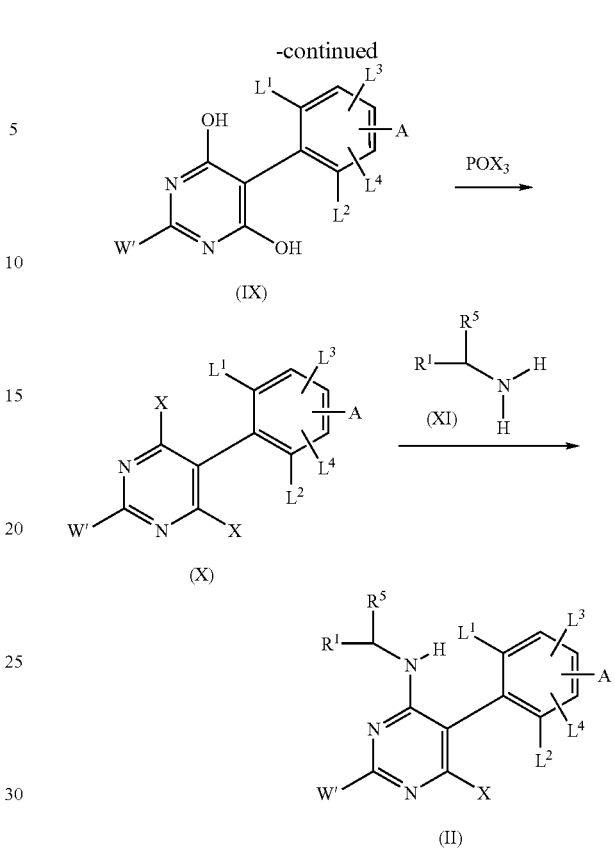

Alternatively, as shown in Scheme IV, compounds of Formula (II) wherein Z is

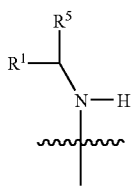

and W' is heteroaryl having 1 to 4 nitrogen heteroatoms may be prepared wherein reaction of heteroaryl reagent W'—H, in which one nitrogen heteroatom is attached to a hydrogen atom in said heteroaryl reagent W'—H, and said nitrogen heteroatom is further connected to the pyrimidine ring of compound (XV) by reaction of heteroaryl reagent W'—H with compound (XIV), which can be further converted to compounds of formula (II). Treating compound (VIII, U.S. Pat. No. 6,156,925) with urea (XII) in the presence of a tertiary amine base, such as tributylamine, at a temperature up to 190° C. provides compound (XIII). Halogenation with halogenating agents $POX_3$, $PX_3$ or $PX_5$, such as phosphorous oxychloride or phosphorous oxybromide gives compound (XIV). Replacement of the 2-halogen of compound (XIV) by reaction with heteroaryl reagent W'—H gives compound (XV). Replacement of an additional halogen of compound (XV) with excess amount of an amine (XI) in a suitable solvent, such as methylene chloride, dimethylsulfoxide or dimethylformamide, provides compounds of formula (II).

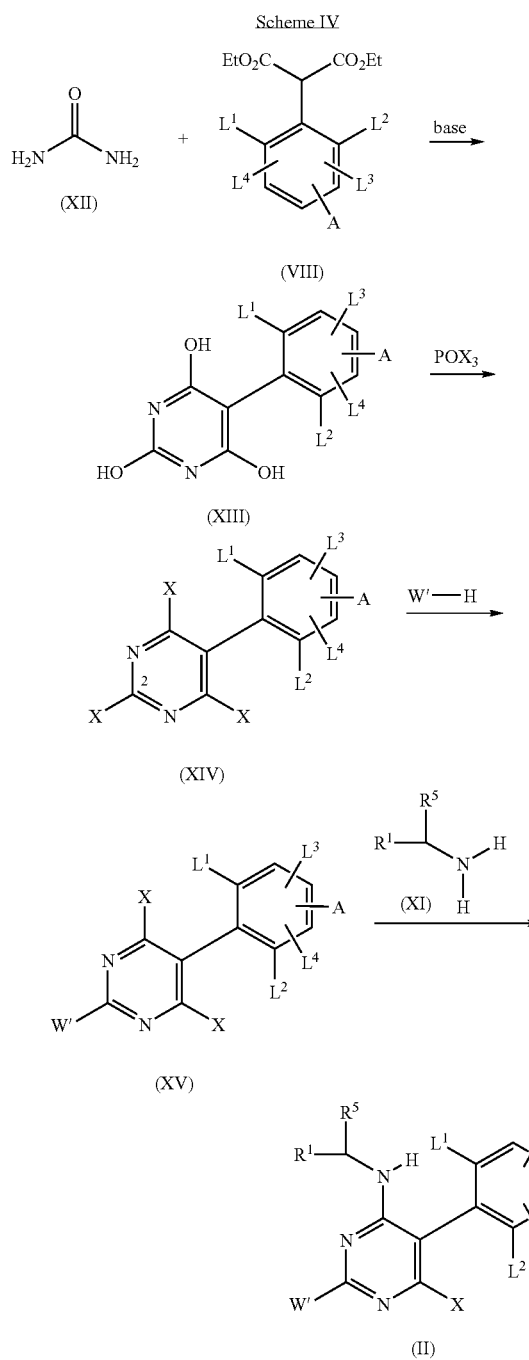

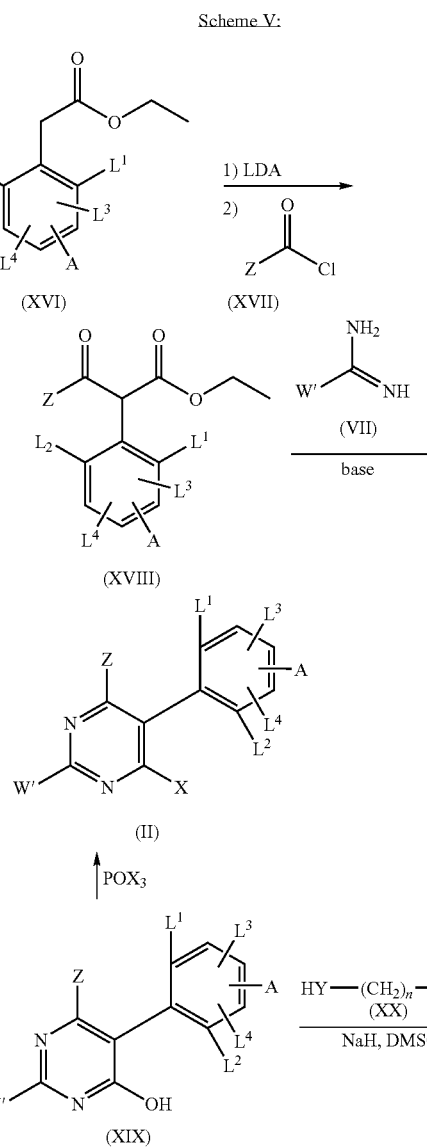

—OH or —NR³R⁴ wherein at least one of R³ or R⁴ is hydrogen, and Q is protected, as the 4-methoxybenzyl group when Q is —OH or as the tert-butoxy carbonyl (t-BOC) group when Q is —NR³R⁴ in the presence of a strong base which includes an alkali metal hydroxide, alkali metal carbonate and alkali hydride, e.g., sodium hydride in an aprotic solvent which includes dimethylsulfoxide, dimethylformamide, and the like to give compound (XXI). Reaction of compound (XXI) with halogenating agents $POX_3$, $PX_3$, or $PX_5$, such as phosphorous oxychloride or phosphorous oxybromide in the presence of a inert base affords compound (XXII) where X is hereinbefore defined. Deprotection of the protecting group on Q with 2,3-dichloro-5,6-dicyano-1,4-benzoquinone (DDQ) in the case of the 4-methoxybenzyl protecting group or trifluoroacetic acid in the case of the tert-butoxy carbonyl (t-BOC) protecting group gives compound (I) where Z is $C_6$-$C_8$ cycloalkyl.

Reaction of compound (XIX) with halogenating agents $POX_3$, $PX_3$, or $PX_5$, such as phosphorous oxychloride or phosphorous oxybromide in the presence of a inert base affords compound (II) where X is hereinbefore defined and A is H, F, Cl, Br or $Y(CH_2)_nQ$ where Q is —NR³R⁴ and R³ and R⁴ are independently alkyl of 1 to 3 carbon atoms.

The preparation of the compounds of this invention encompassed by Formulae (I) and (II) wherein Z is $C_6$-$C_8$ cycloalkyl;

Y is O, S, or —NR² and W' is as hereinbefore defined, can be prepared by a process shown in Scheme V and Scheme VI wherein L¹, L², L³, L⁴, A, X and n are as defined above.

Ester (XVI) is reacted with acid chloride (XVII), prepared from the corresponding carboxylic acid where Z is $C_6$-$C_8$ cycloalkyl, in the presence of lithium diisopropylamide (LDA) to give ketoester (XVIII) which is further reacted with carboxamidine (VII) in the presence of a tertiary amine base, such as tributylamine, at a temperature up to 190° C. provides compound (XIX). When A is a leaving group, in particular a fluorine atom, reaction with compound (XX), in which Q is

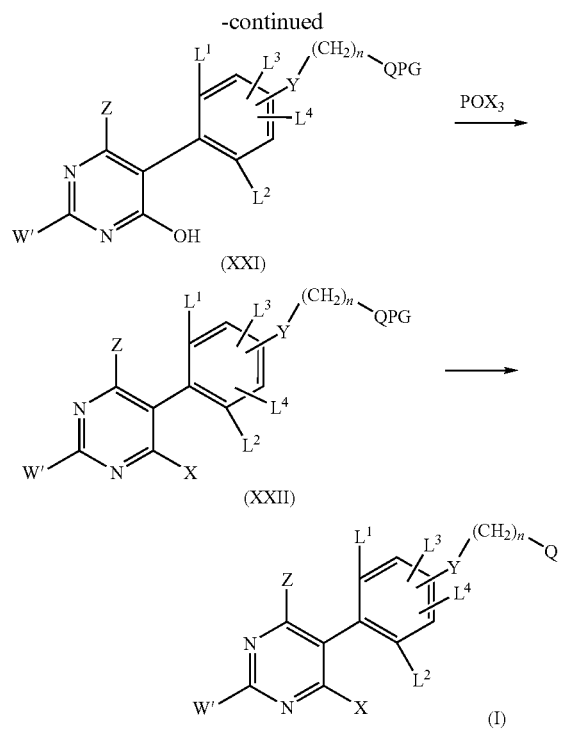
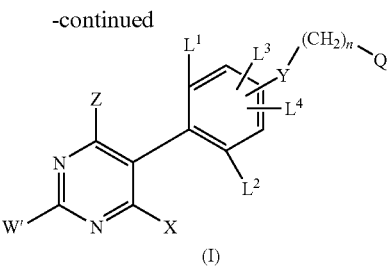

QPG = Q with a protecting group

As shown in Scheme VI, when A is a leaving group, in particular a fluorine atom, reaction with compound (VI), in which Q is —$NR^3R^4$ and $R^3$ and $R^4$ are independently alkyl in the presence of a strong base which includes an alkali metal hydroxide, alkali metal carbonate and alkali hydride, e.g., sodium hydride in an aprotic solvent which includes dimethylsulfoxide, dimethylformamide, and the like to give compound (XXIII). Reaction of compound (XXIII) with halogenating agents $POX_3$, $PX_3$, or $PX_5$, such as phosphorous oxychloride or phosphorous oxybromide in the presence of a inert base affords compound (I) where X is hereinbefore defined.

Scheme VI:

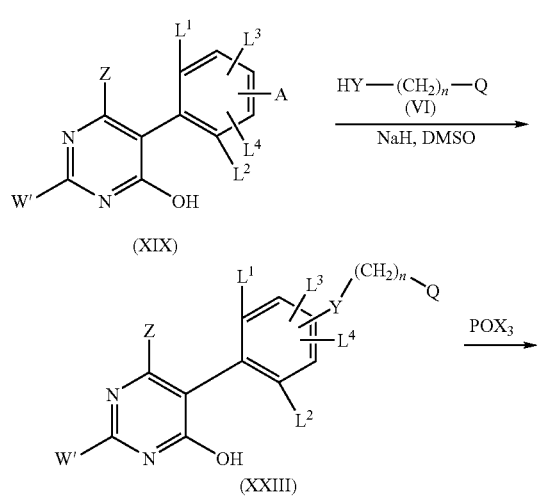

It is understood that this invention encompasses all crystalline and hydrated forms of compounds of Formulae (I) and (II) and their pharmaceutically acceptable salts. The pharmaceutically acceptable salts of the compounds of this invention are those derived from such organic and inorganic pharmaceutically acceptable salt forming acids as: lactic, citric, acetic, tartaric, fumaric, succinic, maleic, malonic, hydrochloric, hydrobromic, phosphoric, nitric, sulfuric, methanesulfonic, benzenesulfonic, L-aspartic, R or S-mandelic, palmitic and similarly known acceptable acids and further including trifluoroacetic acid (TFA). In particular the hydrochloride, fumarate and succinate salts are preferred.

The present invention accordingly provides a pharmaceutical composition which comprises a compound of this invention, (formula I and formula II), in combination or association with a pharmaceutically acceptable carrier. In particular, the present invention provides a pharmaceutical composition which comprises an effective amount of a compound of this invention and a pharmaceutically acceptable carrier.

Based on the results of these standard pharmacological test procedures, the compounds of this invention are useful as agents for treating, inhibiting or controlling the growth of cancerous tumor cells and associated diseases in a mammal in need thereof. The compounds of the invention are useful as agents for treating, inhibiting or controlling the growth of cancerous tumor cells and associated diseases in a mammal in need thereof by interacting with tubulin and microtubules and promoting microtubule polymerization. The compounds of the invention are further useful for the treatment or prevention of cancerous tumors by stabilizing microtubules. The compounds of the invention are also useful for the treatment or prevention of cancerous tumors that express multiple drug resistance (MDR) or are resistant because of MDR.

In particular, when contacting a tubulin containing system with an effective amount of a compound of formulae (I) or (II) results in the promotion of microtubule polymerization and further stabilizes microtubules and by promoting microtubule polymerization and stabilizing microtubules said compounds of formulae (I) and (II) are useful as agents for treating, inhibiting or controlling the growth of cancerous tumor cells and associated diseases. Additionally, compounds of formulae (I) and (II) are useful for the treatment or prevention of cancerous tumors that express multiple drug resistance (MDR) or are resistant because of MDR. The tubulin containing system may be in a tumor cell, thereby inhibiting neoplastic disease by administering an effective amount of a compound described in the present invention. Mammals may be treated and in particular, humans. Further, said tubulin containing system may be in a patient. In the case of cancer treatment, it is believed that many neoplasias such as leukemia, lung cancer, colon cancer, thyroid cancer, ovarian cancer, renal cancer, prostate cancer and breast cancers may be treated by effectively administering effective amounts of the compounds of formulae (I) and (II). As used herein, cancer refers to all types of cancers, or neoplasms or benign or malignant tumors. Preferred cancers for treatment using methods provided herein include carcinoma, sarcoma, lymphoma, or leukemia. By carcinoma is meant a benign or malignant epithelial tumor and includes, but is not limited to, breast carcinoma, prostate carcinoma, non-small lung carcinoma, colon carcinoma, melanoma carcinoma, ovarian carcinoma, or renal carcinoma. A preferred host is a human.

The effective dosage of active ingredient employed may vary depending on the particular compound employed, the mode of administration and severity of the condition being treated. However, in general satisfactory results are obtained when the compounds of the invention are administered in amounts ranging from about 0.10 to about 100 mg/kg of body weight per day. A preferred regimen for optimum results would be from about 1 mg to about 20 mg/kg of body weight per day and such dosage units are employed that a total of from about 70 mg to about 1400 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

Intravenous administration is a preferred manner of administration of compounds of the invention. For intravenous administration examples of non-limiting suitable carriers include physiological saline, bacteriostatic water, Cremophor ELTM (BASF, Parsippany, N.J.) or phosphate buffered saline (PBS). The composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

As used in accordance with this invention, the term providing an effective amount of a compound means either directly administering such compound, or administering a prodrug, derivative, or analog which will form an effective amount of the compound within the body.

In addition to the above utilities some of the compounds of this invention are useful for the preparation of other compounds of this invention.

Examples of this invention are evaluated in several standard pharmacological test procedures that showed that the compounds of this invention possess significant activity as promoters of microtubule polymerization and are antineoplastic agents. Based on the activity shown in the standard pharmacological test procedures, the compounds of this invention are therefore useful as anticancer agents. Associated cancers are selected from the group consisting of breast, colon, lung, prostate, melanoma, epidermal, leukemia, kidney, bladder, mouth, larynx, esophagus, stomach, ovary, pancreas, liver, skin and brain. In particular, the compounds of this invention possess an effect similar to Paclitaxel. The test procedures used and results obtained are shown below.

Materials and Methods

1. Cell Culture Media and Reagents

Medium is RPMI-1640 with L-glutamine, supplemented with 10% heat-inactivated fetal calf serum, 100 units/mL penicillin, and 100 μg/mL streptomycin (Gibco, Grand Island, N.Y.). Microtubule-associated protein (MAP)-rich tubulin, containing about 70% tubulin and 30% MAPs (#ML113), and highly purified tubulin (>99% pure, #TL238), both from bovine brain, are obtained from Cytoskeleton, Inc., Denver, Colo. PEM buffer (80 mM piperazine-N,N'-bis[2-ethanesulfonic acid], pH 6.9, 1 mM ethylene glycol-bis(β-aminoethyl ether)-N,N,N',N'-tetraacetic acid, 1 mM magnesium chloride) and guanosine 5'-triphosphate (GTP) are also obtained from Cytoskeleton. [$^3$H]paclitaxel, specific activity 14.7 Ci/mmol, is purchased from Moravek Biochemicals (Brea, Calif.). [$^3$H]vinblastine, specific activity 9.60 Ci/mmol and MicroSpin G-50 columns are obtained from Amersham Biosciences (Piscataway, N.J.). [$^3$H]colchicine, specific activity 76.5 Ci/mmol, is obtained from New England Nuclear (Boston, Mass.). Other reagents are obtained from Sigma (St. Louis, Mo.).

2. Cell Lines

Human cancer cell lines, unless otherwise noted, are obtained from the American Type Culture Collection (Rockville, Md.). The following drug-sensitive parental cell lines, and their derived drug-resistant counterparts, are obtained from the originators as listed: (a) S1 (parental line from a subclone of human colon carcinoma line LS174T) and derived S1-M1-3.2 (herein called S1-M1) which expresses the MXR drug transporter protein, are provided by Dr. L. Greenberger, Wyeth Research (Rabindran, S. K., He, H., Singh, M., Brown, E., Collins, K. I., Annable, T., and Greenberger, L. M. Reversal of a novel multidrug resistance mechanism in human colon carcinoma cells by fumitremorgin C. Cancer Res., 58: 5850-5858, 1998); (b) parental HL-60 human promyelocytic leukemia line and derived HL-60/ADR, which expresses the MRP1 drug transporter protein, are provided by Dr. M. Center, University of Kansas (McGrath, T., and Center, M. S. Adriamycin resistance in HL60 cells in the absence of detectable P-glycoprotein. Biochem. Biophys. Res. Commun., 145: 1171-1176, 1987), via Dr. L. Greenberger, Wyeth Research; and (c) parental KB-3-1 (herein called KB, cloned from a human epidermoid carcinoma) and the derived lines KB-8-5 and KB-V1, which express moderate and very high levels of the MDR1 (P-glycoprotein) drug transporter protein, respectively, are provided by Dr. M. Gottesman, National Cancer Institute (Shen, D. W., Cardarelli, C., Hwang, J., Cornwell, M., Richert, N., Ishii, S., Pastan, I., and Gottesman, M. M. Multiple drug-resistant human KB carcinoma cells independently selected for high-level resistance to colchicine, adriamycin, or vinblastine show changes in expression of specific proteins. J. Biol. Chem., 261: 7762-7770, 1986) via Dr. L. Greenberger, Wyeth Research.

3. Cytotoxicity Standard Pharmacological Test Procedure

The assay, which is sold in kit form by Promega (Madison, Wis.; CellTiter 96 AQueous Non-Radioactive Cell Proliferation Assay), is based on the conversion by viable cells, but not by dead cells, of the tetrazolium salt, MTS (3-(4,5-dimethylthiazol-2-yl)-5-(3-carboxymethoxyphenyl)-2-(4-sulphophenyl)-2H-tetrazolium, inner salt), into a water-soluble colored formazan which is detected by spectrophotometry. Compounds are tested at nine concentrations, in order to determine $IC_{50}$ values. For the test procedure, cells are harvested by trypsinization, washed, counted and distributed to wells of 96-well flat-bottom microtiter plates at 1000 cells per well in 200 μL of medium. In addition, one row of wells on a separate plate receives cells as above ("time 0" plate). All plates are incubated at 37° in humidified 5% $CO_2$ in air for about 24 hr.

On day 2, compounds for test are diluted and added to wells. Compounds are dissolved in DMSO at 10 mg/mL. For each compound, nine serial 2-fold dilutions are prepared in DMSO. Ten μL of each dilution in DMSO are transferred to 100 μL of medium, mixed well, and then 5 μL of this dilution are transferred in quadruplicate to wells containing cells. The final high concentration of each compound is typically 5 μM. Plates are returned to the incubator for three days. At the time of drug addition to the experimental plates, the MTS assay is run on the "time 0" plate. This produces the "time 0 MTS value" which is related to the number of viable cells per well at the time of drug addition.

After three days of culture with test compounds (day 5 overall), the MTS assay is done on all wells of the experimental plates. The absorbance values of the quadruplicate sample wells are averaged and divided by the average of the "time 0" values. The average of control wells without drug, divided by the average "time 0" value, gives the maximal relative increase in MTS color yield due to cell growth during the final three days of culture. The average of control wells with high drug concentration, divided by the "time 0" value, gives the minimal relative color yield for cells that were completely killed. The nine values for each compound are plotted against concentration, and the concentration that produces a relative color yield half way between the maximum and minimum is taken as the $IC_{50}$ value. The most potent compounds have the lowest $IC_{50}$ values.

4. Tubulin Polymerization Standard Pharmacological Test Procedure

MAP-rich tubulin is dissolved in ice-cold PEM buffer containing 1 mM GTP (GPEM buffer) at a concentration of 1.3 mg/mL. The solution is centrifuged at top speed in an Eppendorf model 5415C microcentrifuge (Brinkmann Instruments, Westbury, N.Y.) for 10 min at 4° immediately before use. The tubulin solution is added to wells of a ½-area 96-well plate (Costar No. 3696, Corning, Inc., Corning, N.Y.) already containing the compounds of interest. Each compound is tested in duplicate at a final concentration of 0.3 μM in a volume of 110 μL per well. The final DMSO concentration in all wells is 0.3%. Control reactions, which receive compound solvent only, are done in quadruplicate. The plate is put in a SpectraMax Plus plate reader (Molecular Devices Corp. Sunnyvale, Calif.) thermostated at 24° and the absorbance of each well at 340 nm, a measure of the appearance of turbidity due to tubulin polymer formation, is determined every minute for 60 minutes. The absorbance at time 0 for each well is subtracted from each of the subsequent absorbance readings for that well, and then the duplicates are averaged.

5. Competitive Binding Standard Pharmacological Test Procedure

The binding of examples of this invention to highly purified tubulin is studied by competitive inhibition methods. The αβ-tubulin heterodimer contains binding sites for the three major classes of microtubule-active pharmacological agents: taxanes, vinca/peptide-site agents, and colchicine-site agents. To study possible competition at the vinca/peptide and colchicine sites, incubations are done under conditions which do not favor polymerization because vinblastine and colchicine bind preferentially to unpolymerized heterodimer. To study possible competition at the taxane site, on the other hand, polymerized tubulin (microtubules) is used because paclitaxel binds preferentially to microtubules.

Highly purified tubulin is dissolved in PEM buffer without GTP and used at a final concentration of 1.0 to 1.3 mg/ml (10 to 13 µM). To aliquots of the tubulin solution are added various competitors (in quadruplicate) at 100 µM final concentrations, and [$^3$H]vinblastine or [$^3$H]colchicine at final concentrations of 100 nM or 50 nM, respectively. These solutions are incubated at 24° for 1 hr and then applied to MicroSpin G-50 columns which are centrifuged for 2 min at 3000 rpm in an Eppendorf 5415C microfuge. An aliquot of each column effluent (containing tubulin and bound radioligand) is mixed with scintillation fluid and counted in a liquid scintillation spectrometer. Controls include samples without competitor, and samples with unlabeled vincristine, colchicine, or paclitaxel. Quadruplicates are averaged, and the ability of the competitor to inhibit the binding of the radioligand is expressed as a percentage of control binding in the absence of any competitor.

For competition with [$^3$H]paclitaxel, highly purified tubulin is dissolved in PEM buffer containing 0.75 M glutamate and 25 µM dideoxy-GTP; final protein concentration is 0.25 to 0.35 mg/mL (2.5 to 3.5 µM). These conditions foster the rapid formation of short, stable microtubule polymers (Hamel, E., del Campo, A. A., and Lin, C. M. Stability of tubulin polymers formed with dideoxyguanosine nucleotides in the presence and absence of microtubule-associated proteins. J. Biol. Chem., 259: 2501-2508,1984). This solution is incubated for 30 min at 370 to allow microtubules to form. Then [$^3$H]paclitaxel (final concentration of 2.1 µM, 1.2 Ci/mmol) and competitor (final concentration of 20 µM, except 5 µM for unlabeled paclitaxel) are added to aliquots of the polymerized tubulin solution and incubation at 37° is continued for another 30 min. Controls include samples without competitor, and samples with unlabeled vincristine, colchicine, or paclitaxel. The reactions are then centrifuged at top speed in an Eppendorf 5415C microfuge for 20 min at room temperature in order to pellet the microtubule protein. Triplicate aliquots of each supernatant are mixed with scintillation fluid and counted in a liquid scintillation spectrometer. From the amount of radioactivity in the supernatants and the measured total starting radioactivity, the amount of [$^3$H] paclitaxel bound to pelleted microtubule protein is calculated. The ability of each competitor to inhibit radioligand binding to pelleted protein is expressed as a percent of controls without any competitor.

6. Antitumor Activity in Athymic Mice Bearing Human Tumor Xenografts Standard Pharmacological Test Procedure The ability of compounds of this invention to inhibit tumor growth in animals is studied in the athymic mouse xenograft standard pharmacological test. Female nu/nu mice in an outbred albino background are obtained from Charles River Laboratories (Wilmington, Mass.). Animals are injected subcutaneously on the flank with the desired tumor cell suspension. Several days later, mice with tumors of approximately 100 mm$^3$ are selected from those injected (staged) and randomly distributed into groups of 5-10. The day of staging is called day 0. Compounds of the invention, formulated in saline, are administered to animals by intravenous injection or oral gavage on various schedules starting on day 0 or 1, as noted in the tables. The control group in each experiment is dosed with vehicle on the same schedule. Tumor size is measured every 3-7 days with calipers in two orthogonal dimensions, and tumor volume is calculated from the formula volume=[(length×width$^2$)/2].

Tumor/Control (T/C) is obtained by dividing the mean tumor volume of the treated group by the mean tumor volume of the control group on each measurement day. A treatment dose is defined as active if it produces a statistically significant T/C of 0.50 or less. A p value≦0.05, determined by one-side Student's t-test, is required for statistical significance. A treatment dose is defined as toxic if more than 30% of the animals die from a compound-related toxicity.

Results

1. Cytotoxicity Standard Pharmacological Test Procedure
   1.1. With COLO 205 Cells COLO 205 is a human colon carcinoma cell line that is used for comparative testing of the examples of this invention and several reference compounds. This line is sensitive to paclitaxel and vincristine. As shown in Table 1, for example, Example 32a has an IC$_{50}$ value of 2.4 nM, comparable to those of paclitaxel and vincristine.

TABLE 1

Activity of Representative Examples of the Invention and Reference Compounds in the MTS Cytotoxicity Standard Pharmacological Test Procedure with COLO 205 Cells[1]

| Example or Reference Compound | Salt | IC$_{50}$ (nM) | SD | n |
|---|---|---|---|---|
| 1 | | 214 | 41 | 9 |
| 2 | | 304 | 153 | 2 |
| 3 | | 51 | 2 | 3 |
| 4 | | 84 | 11 | 5 |
| 5 | | 265 | — | 1 |
| 6 | | 7050 | — | 1 |
| 7 | | 3930 | 373 | 2 |
| 8 | | 39 | 8 | 5 |
| 9 | | 29 | 6 | 4 |
| 10 | | 250 | 23 | 2 |
| 11 | | 4680 | 251 | 2 |
| 12 | | 119 | 4 | 2 |
| 13 | | 3465 | — | 1 |
| 14 | | 232 | — | 1 |
| 15 | | 3030 | 111 | 3 |
| 16 | | 53 | 5 | 5 |
| 17 | | 19 | 6 | 4 |
| 18 | | 7080 | — | 1 |
| 19 | | 52 | 12 | 8 |
| 20a | TFA salt | 56 | 3 | 2 |
| 21 | | 36 | 10 | 4 |
| 22 | | 532 | — | 1 |
| 23 | | 229 | — | 1 |
| 24 | | 6.9 | 2.2 | 5 |
| 24a | HCl salt | 8.9 | 0.7 | 4 |
| 25 | | 22 | 5 | 9 |
| 25a | HCl salt | 18 | 3 | 4 |
| 26 | | 49 | — | 1 |
| 27 | | 128 | 47 | 3 |
| 28 | | 32 | 14 | 3 |
| 29a | HCl salt | 5.2 | 1.3 | 4 |
| 30 | | 7.4 | — | 1 |
| 31 | | 682 | 232 | 2 |
| 32a | HCl salt | 2.4 | 0.3 | 10 |
| 33a | TFA salt | 8.2 | 0.6 | 2 |
| 34 | | 77 | 22 | 2 |
| 35 | | 7027 | | 1 |
| 36 | | 109 | | 1 |
| 37 | | 132 | 24 | 2 |
| 38 | | 23 | | 1 |
| Paclitaxel | | 3.3 | 1.0 | 20 |
| Vincristine | | 2.6 | 0.5 | 7 |

[1]IC$_{50}$ values and standard deviations are from the indicated number of independent experiments

1.2 With KB, KB-8-5, and KB-V1 Cells

The KB lines express different amounts of the P-glycoprotein (MDR1) membrane pump which produces resistance to the action of many cytotoxic compounds, including paclitaxel and vincristine. The parental KB line expresses no P-glycoprotein, kB-8-5 expresses moderate levels of the protein, and KB-V1 expresses very high levels. The ability of P-glycoprotein to recognize and export a potential cytotoxic agent can be inferred from the change in $IC_{50}$ values on these lines (Loganzo, F., Discafani, C. M., Annable, T., Beyer, C., Musto, S., Hari, M., Tan, X., Hardy, C., Hernandez, R., Baxter, M., Singanallore, T., Khafizova, G., Poruchynsky, M. S., Fojo, T., Nieman, J. A., Ayral-Kaloustian, S., Zask, A., Andersen, R. J., and Greenberger, L. M. HTI-286, a synthetic analogue of the tripeptide hemiasterlin, is a potent antimicrotubule agent that circumvents P-glycoprotein-mediated resistance in vitro and in vivo. Cancer Res., 63: 1838-1845, 2003). If a compound is recognized by P-glycoprotein, its $IC_{50}$ value will increase substantially (several hundred-fold) on going from KB to KB-8-5 to KB-V1; if a compound is not recognized, it will have similar $IC_{50}$ values (3-fold or less difference) on all three lines. For example, as shown in Table 2, KB-8-5 cells are moderately resistant to paclitaxel (11-fold), vincristine (26-fold), colchicine (4.7-fold) and doxorubicin (6.8-fold). In contrast, several representative examples of this invention (Nos. 19, 20a, 21, 25a, 30, and 33a) show less than a 3-fold change in $IC_{50}$ values.

Even slight interactions of compounds with P-glycoprotein can be determined with the KB-V1 line, which expresses a level of this protein higher than is typically found in clinical samples from a variety of tumors (Goldstein, L. J., Galski, H., Fojo, T., Willingham, M., Lai, S. L., Gazdar, A., Pirker, R., Green, A., Crist, W., Brodeur, G. M., Lieber, M., Cossman, J., Gottesman, M. M., and Pastan, I. Expression of a multidrug resistance gene in human cells. J. Natl. Cancer Inst. (Bethesda), 81: 116-124,1989). As also shown in Table 2, KB-V1 cells are highly resistant to paclitaxel (822-fold), vincristine (925-fold), colchicine (92-fold), and doxorubicin (>79-fold). Two of the compounds of this invention (Nos. 19 and 30) show less than a 3-fold change in $IC_{50}$ compared to the parental KB line. This indicates that these compounds are not recognized at all by P-glycoprotein and therefore that they completely overcome P-glycoprotein-mediated resistance to cell killing. Other representative examples of the invention (Nos. 20a, 21, 25a, and 33a) show recognition by P-glycoprotein, but much less than that shown by paclitaxel and vincristine.

TABLE 2

Activity of Representative Examples of the Invention and Reference Compounds in the MTS Cytotoxicity Standard Pharmacological Test Procedure with KB, KB-8.5 and KB-VI Cells

| Example or Reference | Salt | $IC_{50}$ (nM)[1] | | | Ratio[2] | |
|---|---|---|---|---|---|---|
| | | KB | KB 8.5 | KB VI | 8.5/KB | VI/KB |
| 19 | | 63 | 69 | 176 | 1.1 | 2.8 |
| 20a | TFA | 26 | 57 | 140 | 2.2 | 5.5 |
| 21 | | 24 | 59 | 82 | 2.5 | 3.5 |
| 24a | HCl | 7.0 | 24 | 405 | 3.5 | 58 |
| 25a | HCl | 20 | 24 | 99 | 1.2 | 4.9 |
| 29a | HCl | 6.2 | 21 | 423 | 3.4 | 69 |
| 30 | | 60 | 68 | 82 | 1.1 | 1.4 |
| 32a | HCl | 2.4 | 32 | 569 | 14 | 242 |
| 33a | TFA | 6.8 | 7.5 | 91 | 1.1 | 13 |
| Paclitaxel | | 2.5 | 26 | 2014 | 11 | 822 |
| Vincristine | | 2.2 | 58 | 2036 | 26 | 925 |
| Colchicine | | 13 | 61 | 1195 | 4.7 | 92 |
| Mitoxantrone | | 132 | 256 | 401 | 1.9 | 3.0 |
| Doxorubicin | | 38 | 255 | >300 | 6.8 | >79 |

[1]$IC_{50}$ values are means of 2 independent experiments.
[2]Ratio = $IC_{50}$ on KB 8.5 or KB VI cells/$IC_{50}$ on KB cells. A ratio of about 1 indicates no resistance.

1.3. With HL-60 and HL-60/ADR Cells

HL-60/ADR cells overexpress the multidrug resistance protein MRP1 which mediates resistance to some chemotherapeutics (Gottesman, M. M., Fojo, T., and Bates, S. E. Multidrug resistance in cancer: role of ATP-dependent transporters. Nature Rev. Cancer, 2: 48-58, 2002). The $IC_{50}$ values of representative examples of this invention, as well as reference compounds, on HL-60/ADR are compared to values on the sensitive parental HL-60 line. The results, shown in Table 3, indicate that whereas HL-60/ADR cells show resistance to vincristine (9.6-fold), colchicine (8.7-fold), mitoxantrone (15-fold), and doxorubicin (>75-fold), these cells show no resistance to any of the representative examples. This indicates that the compounds of this invention are not recognized by MRP1 and therefore overcome cellular resistance mediated by this transporter.

TABLE 3

Activity of Representative Examples of the Invention and Reference Compounds in the MTS Cytotoxicity Standard Pharmacological Test Procedure with HL-60 and HL-60/ADR Cells

| Example or Reference | Salt | $IC_{50}$ (nM)[1] | | Ratio[2] |
|---|---|---|---|---|
| | | HL-60 | HL-60/ADR | |
| 19 | | 66 | 60 | 0.9 |
| 20a | TFA | 72 | 68 | 0.9 |
| 21 | | 58 | 37 | 0.6 |
| 24a | HCl | 6.6 | 6.3 | 1.0 |
| 25a | HCl | 23 | 21 | 0.9 |
| 29a | HCl | 6.9 | 6.8 | 1.0 |
| 30 | | 88 | 71 | 0.8 |
| 32a | HCl | 2.6 | 2.2 | 0.8 |
| 33a | TFA | 6.9 | 6.1 | 0.9 |
| Paclitaxel | | 3.0 | 3.5 | 1.2 |
| Vincristine | | 2.5 | 24 | 9.6 |
| Colchicine | | 21 | 182 | 8.7 |
| Mitoxantrone | | 17 | 259 | 15 |
| Doxorubicin | | 40 | >3000 | >75 |

[1]$IC_{50}$ values are means of 2 independent experiments.
[2]Ratio = $IC_{50}$ on HL-60/ADR cells/$IC_{50}$ on HL-60 cells. A ratio of about 1 indicates no resistance.

1.4. With S1 and S1-M1 Cells

S1-M1 cells overexpress the MXR transporter which mediates resistance to some chemotherapeutics (Gottesman, M. M., Fojo, T., and Bates, S. E. Miltidrug resistance in cancer: role of ATP-dependent transporters. Nature Rev. Cancer, 2: 48-58, 2002). The $IC_{50}$ values of representative examples of this invention, as well as reference compounds, on S1-M1 are compared to values on the sensitive parental S1 line. The results, shown in Table 4, indicate that whereas S1-M1 cells show resistance to mitoxantrone (>120-fold) and doxorubicin (47-fold), they show no resistance to any of the examples. This indicates that the compounds of this invention are not recognized by MXR and therefore overcome cellular resistance mediated by this transporter.

TABLE 4

Activity of Representative Examples of the Invention and Reference Compounds in the MTS Cytotoxicity Standard Pharmacological Test Procedure with S1 and S1-M1 Cells

| Example or Reference | Salt | $IC_{50}$ (nM)[1] S1 | S1-M1 | Ratio[2] |
|---|---|---|---|---|
| 19 | | 88 | 88 | 1.0 |
| 20a | TFA | 95 | 82 | 0.9 |
| 21 | | 66 | 76 | 1.2 |
| 24a | HCl | 20 | 53 | 2.7 |
| 25a | HCl | 27 | 36 | 1.3 |
| 29a | HCl | 7.9 | 21 | 2.7 |
| 30 | | 138 | 201 | 1.5 |
| 32a | HCl | 9.9 | 8.7 | 0.9 |
| 33a | TFA | 8.5 | 12 | 1.4 |
| Paclitaxel | | 4.2 | 2.7 | 0.6 |
| Vincristine | | 14 | 7.9 | 0.6 |
| Colchicine | | 37 | 109 | 2.9 |
| Mitoxantrone | | 25 | >3000 | >120 |
| Doxorubicin | | 61 | 2875 | 47 |

[1]$IC_{50}$ values are means of 2 independent experiments.
[2]Ratio = $IC_{50}$ on S1-M1 cells/$IC_{50}$ on S1 cells. A ratio of about 1 indicates no resistance.

2. Effects of Compounds on Polymerization of MAP-Rich Tubulin In Vitro

In this assay, control reactions with MAP-rich tubulin show an S-shaped absorbance profile characterized by three phases: first, a lag phase during which no change in absorbance occurs; second, a polymerization phase in which absorbance increases; and third, a plateau phase in which absorbance reaches a maximum and little or no further change occurs. Polymerization enhancers such as paclitaxel and docetaxel shorten or eliminate the lag phase, increase the rate of the polymerization phase, and often increase the height of the plateau. Polymerization inhibitors such as vincristine and colchicine reduce or prevent the absorbance increase. Representative compounds of this invention have a taxane-like effect on the polymerization reaction. This is expressed quantitatively in Table 5 by dividing the mean $A_{340}$ of each sample at 20 min by the mean $A_{340}$ of the control at 20 min to give a fold enhancement over control. Paclitaxel shows an enhancement factor of 2.4, and docetaxel shows a factor of 8.6. Most examples of this invention have factors ranging from 2.3 to 6.1 while Example 33a, has a value of 0.5. In contrast, vincristine and colchicine give enhancement factors of 0.2 and 0.5, respectively, because they inhibit polymerization of MAP-rich tubulin.

TABLE 5

Activity of Representative Examples of the Invention and Reference Compounds in the Tubulin Polymerization Standard Pharmacological Test Procedure with MAP-rich Tubulin

| Example or Reference Compound | Salt | $A_{340}$ Compound / $A_{340}$ Control |
|---|---|---|
| 21 | | 6.1 |
| 24a | HCl | 2.3 |
| 29a | HCl | 2.4 |
| 32a | HCl | 2.3 |
| 33a | TFA | 0.5 |
| Paclitaxel | | 2.4 |
| Docetaxel | | 8.6 |
| Vincristine | | 0.2 |
| Colchicine | | 0.5 |
| Control | | 1.0 |

3. Binding of Compounds to Tubulin

The site on highly purified bovine brain tubulin to which compounds of this invention bind is determined by competitive inhibition studies with the radioactive ligands [$^3$H]vinblastine, [$^3$H]colchicine, and [$^3$H]paclitaxel. The results, shown in Table 6, indicate that all of the tested compounds inhibit the binding of [$^3$H]vinblastine to tubulin heterodimer (12-30% of control), but do not inhibit binding of [$^3$H]colchicine to tubulin heterodimer or of [$^3$H]paclitaxel to microtubules. This is strong evidence that these compounds bind at the vinca/peptide site of tubulin and not at the colchicine or taxane sites. Among the control compounds tested, vincristine inhibits [$^3$H]vinblastine binding but not [$^3$H]colchicine, and colchicine inhibits [$^3$H]colchicine binding but not [$^3$H]vinblastine. Vincristine and colchicine also appear to inhibit the binding of [$^3$H]paclitaxel to microtubules; however, this is not due to binding competition but rather to depolymerization of the microtubules to which [$^3$H]paclitaxel binds. Example 19 of this invention does not reduce [$^3$H]paclitaxel binding to microtubules, which indicates that it neither competes with [$^3$H]paclitaxel for binding nor depolymerizes the microtubules to which [$^3$H]paclitaxel binds.

TABLE 6

Activity of Representative Examples of the Invention and Reference Compounds in the Competitive Binding Standard Pharmacological Test Procedure[1]

| | Radioactive Ligand | | | | | |
|---|---|---|---|---|---|---|
| | [$^3$H]Vinblastine | | [$^3$H]Colchicine | | [$^3$H]Paclitaxel | |
| Competitor | Mean[2] | SD[2] | Mean[2] | SD[2] | Mean[3] | SD[3] |
| Control | 100 | | 100 | | 100 | |
| Example 1 | 30 | 1.8 | 47 | 3.1 | — | — |
| Example 19 | 22 | 4.7 | 116 | 4.6 | 103 | 3.1 |
| Example 21 | 12 | 1.8 | 105 | 6.3 | — | — |
| Vincristine | 5 | 1.0 | 99 | 7.9 | 22 | 0.9 |

TABLE 6-continued

Activity of Representative Examples of the
Invention and Reference Compounds in
the Competitive Binding Standard
Pharmacological Test Procedure[1]

| | Radioactive Ligand | | | | | |
|---|---|---|---|---|---|---|
| | [$^3$H]Vinblastine | | [$^3$H]Colchicine | | [$^3$H]Paclitaxel | |
| Competitor | Mean[2] | SD[2] | Mean[2] | SD[2] | Mean[3] | SD[3] |
| Colchicine | 125 | 12.6 | 6 | 1.9 | 19 | 0.2 |
| Paclitaxel | 92 | 7.8 | 93 | 12.3 | 35 | 1.6 |

[1]Results are expressed as percent of binding to control without competitor.
[2]Data are from 1 (4 replicates) or 2 (8 replicates) independent experiments.
[3]Data are from 1 to 4 independent experiments (3 to 12 replicates).

4. In Vivo Anti-Tumor Activity of Compounds

Several experiments with human tumor xenografts in athymic mice are done to evaluate the ability of compounds of this invention to inhibit tumor growth in vivo. Table 7 shows results for example 21a with mice bearing H157 non-small cell lung carcinoma (NSCLC). The compound inhibits tumor growth when dosed intravenously at 5 mg/kg/dose on days 1 and 8.

Example 24a inhibits the growth of U87-MG glioblastoma xenografts when dosed intravenously on day 1 with 5 mg/kg, although some compound toxicity is also observed (Table 8). This example also inhibits the growth of H157 NSCLC xenografts when dosed orally on days 1 and 7 with 5 or 1 mg/kg/dose (Table 9).

Example 25a inhibits the growth of H157 NSCLC xenografts when dosed intravenously on day 0 with 10, 5, or 2.5 mg/kg (Table 10) although some compound toxicity is observed at the highest dose.

Example 29a inhibits the growth of H157 NSCLC xenografts when dosed intravenously on day 0 with 2.5 mg/kg, and when dosed orally on day 0 with 5 mg/kg (Table 11).

Example 32a inhibits the growth of H157 NSCLC xenografts as shown in Table 12 when given intravenously on days 0 and 7 at 3 or 1.5 mg/kg/dose. Examples 24a and 29a are also tested against the highly resistant DLD1 colon carcinoma xenograft, which is resistant to paclitaxel and vinblastine because of high expression of the drug transporter P-glycoprotein. Example 24a inhibits the growth of this tumor when given orally on days 1 and 7 at 10 mg/kg/dose, (Table 13).

TABLE 7

In Vivo Activity of Example 21a in the
Human Tumor Xenograft Standard
Pharmacological Test Procedure with
Mice Bearing H157 Human Non-Small Cell
Lung Carcinoma

| Compound | Schedule (days) | Route | Dose (mg/kg) | T/C on day 0 | 4 | 7 | 11 |
|---|---|---|---|---|---|---|---|
| Example 21a, HCl salt | 1, 8 | IV | 10 | 1.01 | 0.87 | 0.73 | 0.73 |
| | | | 5 | 0.99 | 0.49* | 0.44** | 0.38** |
| | | | 1 | 0.97 | 0.76 | 0.70 | 0.67 |

\* = p < 0.05
\*\* = p < 0.01
Vehicle was normal saline

TABLE 8

In Vivo Activity of Example 24a in the
Human Tumor Xenograft Standard
Pharmacological Test Procedure with
Mice Bearing U87-MG Human Glioblastoma

| Compound | Schedule (days) | Route | Dose (mg/kg) | T/C on day 0 | 3 | 7 | 10 |
|---|---|---|---|---|---|---|---|
| Example 24a, HCl salt | 1 | IV | 10 | 1.04 | 0.31** | Toxic | — |
| | | | 5 | 1.04 | 0.41** | 0.21** | 0.17** |
| | | | 1 | 1.03 | 0.71* | 0.75 | 0.86 |

\* = p < 0.05
\*\* = p < 0.01
Vehicle was normal saline
Note:
3 out of 10 animals in the group dosed at 5 mg/kg died from compound toxicity

TABLE 9

In Vivo Activity of Example 24a in the
Human Tumor Xenograft Standard
Pharmacological Test Procedure with
Mice Bearing H157 Human Non-Small Cell
Lung Carcinoma

| Compound | Schedule (days) | Route | Dose (mg/kg) | T/C on day 0 | 4 | 7 | 10 | 13 |
|---|---|---|---|---|---|---|---|---|
| Example 24a, HCl salt | 1, 7 | PO | 5 | 0.98 | 0.64** | 0.51** | 0.16** | 0.12** |
| | | | 1 | 0.96 | 0.73* | 0.70 | 0.58 | 0.50* |

\* = p < 0.05
\*\* = p < 0.01
Vehicle was normal saline

TABLE 10

In Vivo Activity of Example 25a in the Human Tumor Xenograft Standard Pharmacological Test Procedure with Mice Bearing H157 Human Non-Small Cell Lung Carcinoma

| Compound | Schedule (days) | Route | Dose (mg/kg) | T/C on day 0 | 3 | 7 | 10 | 13 |
|---|---|---|---|---|---|---|---|---|
| Example 25a, HCl salt | 0 | IV | 10 | 1.01 | 0.49** | 0.36** | 0.22** | 0.12** |
|  |  |  | 5 | 1.02 | 0.69* | 0.44** | 0.29** | 0.23** |
|  |  |  | 2.5 | 1.05 | 0.84 | 0.51* | 0.48* | 0.43* |

\* = p < 0.05
\*\* = p < 0.01
Vehicle was normal saline
Note:
1 out of 10 animals in the group dosed at 10 mg/kg died from compound toxicity

TABLE 11

In Vivo Activity of Example 29a in the Human Tumor Xenograft Standard Pharmacological Test Procedure with Mice Bearing H157 Human Non-Small Cell Lung Carcinoma

| Compound | Schedule (days) | Route | Dose (mg/kg) | T/C on day 0 | 2 | 7 | 9 | 14 |
|---|---|---|---|---|---|---|---|---|
| Example 29a, HCl salt | 0 | IV | 5 | 1.03 | 0.34** | Toxic | — | — |
|  |  |  | 2.5 | 0.99 | 0.51** | 0.55** | 0.32** | 0.27** |
|  |  |  | 1.25 | 1.01 | 0.59** | 0.72 | 0.67 | 0.68 |
|  | 0 | PO | 5 | 1.02 | 0.43** | 0.37** | 0.33** | 0.25** |

\* = p < 0.05
\*\* = p < 0.01
Vehicle was normal saline

TABLE 12

In Vivo Activity of Example 32a in the Human Tumor Xenograft Standard Pharmacological Test Procedure with Mice Bearing H157 Human Non-Small Cell Lung Carcinoma

| Compound | Schedule (days) | Route | Dose (mg/kg) | T/C on day 0 | 4 | 7 | 13 |
|---|---|---|---|---|---|---|---|
| Example 32a, HCl salt | 0, 7 | IV | 3 | 0.95 | 0.72 | 0.46** | 0.10** |
|  |  |  | 1.5 | 0.95 | 0.89 | 0.63* | 0.48* |

\* = p < 0.05
\*\* = p < 0.01
Vehicle was normal saline

TABLE 13

In Vivo Activity of Examples 24a and 29a in the Human Tumor Xenograft Standard Pharmacological Test Procedure with Mice Bearing DLD1 Human Colon Carcinoma

| Compound | Schedule (days) | Route | Dose (mg/kg) | T/C on day 0 | 7 | 14 |
|---|---|---|---|---|---|---|
| Example 24a, HCl salt | 1, 7 | PO | 10 | 1.0 | 0.82 | 0.28** |
|  |  |  | 5 | 1.0 | 1.07 | 0.85 |
|  |  |  | 2.5 | 1.0 | 0.87 | 0.80 |
| Example 24a, HCl salt | 1, 7 | IV | 10 | 1.0 | Toxic | — |
|  |  |  | 5 | 1.0 | 0.24** | Toxic |
|  |  |  | 2.5 | 1.0 | 1.14 | 0.91 |
| Example 29a, HCl salt | 1, 7 | PO | 5 | 1.0 | 0.79 | 0.59* |
|  |  |  | 2.5 | 1.0 | 1.33 | 1.10 |
|  |  |  | 1 | 1.0 | 1.40 | 1.02 |
| Example 29a, HCl salt | 1, 7 | IV | 5 | 1.0 | 0.22** | Toxic |
|  |  |  | 2.5 | 1.0 | 0.66* | 0.62* |
|  |  |  | 1 | 1.0 | 0.63* | 0.71* |

\* = p < 0.05
\*\* = p < 0.01
Vehicle was normal saline
Note:
1 out of 5 animals in the group dosed orally with Example 24a at 10 mg/kg died from compound toxicity Compounds of this invention show potent cytotoxic activity against multiple human cancer cell lines in culture, including lines that are resistant to paclitaxel and vincristine because of drug transporter overexpression. The compounds enhance the initial rate of MAP-rich tubulin polymerization, in a manner reminiscent of taxanes and distinct from the inhibitory effects of depolymerizers such as vinca alkaloids and colchicine, despite the fact that they bind to the vinca/peptide site of tubulin. Representative compounds inhibit the growth of human tumor xenografts in athymic mice by both intravenous and oral dosing, including a tumor resistant to paclitaxel and vinblastine because of P-glycoprotein overexpression.

The following reference examples are useful for the preparation of the representative non-limiting examples of compounds of this invention which are useful as promoters of microtubule polymerization and as anticancer agents.

REFERENCE EXAMPLE 1

(1S)-2,2,2-Trifluoro-1-methylethylamine hydrogen chloride

The product (1S)-2,2,2-trifluoro-1-methylethylamine hydrogen chloride is prepared according to the conditions disclosed in U.S. Pat. No. 5,986,135 and U.S. Pat. No. 6,204,269.

REFERENCE EXAMPLE 2

5,7-Dichloro-6-(2,4,6-trifluorophenyl)[1,2,4]triazolo[1,5-a]pyrimidine

The product, 5,7-dichloro-6-(2,4,6-trifluorophenyl)[1,2,4]triazolo[1,5-a]pyrimidine is prepared according to the conditions disclosed in U.S. Pat. No. 6,117,876 and U.S. Pat. No. 6,297,251.

REFERENCE EXAMPLE 3

Diethyl 2-(2,4,6-trifluorophenyl)malonate

The product diethyl 2-(2,4,6-trifluorophenyl)malonate is prepared according to the conditions disclosed in U.S. Pat. No. 6,156,925.

REFERENCE EXAMPLE 4

3-(Methylamino)propan-1-ol

The product 3-(methylamino)propan-1-ol is prepared according to the conditions disclosed in *J. Org. Chem.* 44, 2718 (1979).

REFERENCE EXAMPLE 5

5-Nitropyridine-2-carbonitrile

The product, 5-nitropyridine-2-carbonitrile is prepared according to the conditions described in *J. Med. Chem.* 37, 18 (1994).

EXAMPLE 1

4-Chloro-6-[(2,2,2-trifluoroethyl)amino]-5-(2,4,6-trifluorophenyl)pyrimidin-2-yl(methyl)cyanamide

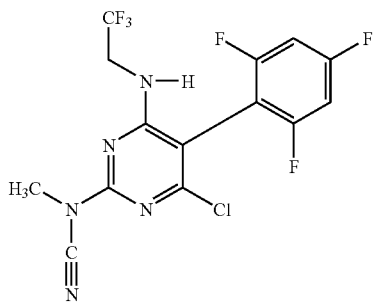

Step A: 5-Chloro-6-(2,4,6-trifluorophenyl)-N-(2,2,2-trifluoroethyl)[1,2,4]triazolo[1,5-a]pyrimidin-7-amine A mixture of 5,7-dichloro-6-(2,4,6-trifluorophenyl)[1,2,4]triazolo[1,5-a]pyrimidine (3.19 g, 10 mmol), 2,2,2-trifluoroethylamine (3.0 g, 30 mmol), and triethylamine (3.0 g, 30 mmol) in 30 mL of N,N-dimethylformamide is stirred at room temperature under nitrogen atmosphere for 1 h. The reaction mixture is diluted with ethyl acetate. The organic layer is washed with saturated sodium chloride (×3), dried over magnesium sulfate, and concentrated. The residue is filtered through hydrous magnesium silicate. Concentration provides 5-chloro-6-(2,4,6-trifluorophenyl)-N-(2,2,2-trifluoroethyl)[1,2,4]triazolo[1,5-a]pyrimidin-7-amine as a light yellow solid (3.70 g). MS: m/z 381.9 (M+H).

Step B: N-[5-Chloro-3-methyl-6-(2,4,6-trifluorophenyl)[1,2,4]triazolo[1,5-a]pyrimidin-7(3H)-ylidene]-2,2,2-trifluoroethanamine To a solution of 5-chloro-6-(2,4,6-trifluorophenyl)-N-(2,2,2-trifluoroethyl)[1,2,4]triazolo[1,5-a]pyrimidin-7-amine (300 mg, 0.78 mmol) in 4 mL of dimethylsulfoxide at room temperature is added iodomethane (146 μL, 2.34 mmol) followed by sodium hydride (60% in mineral oil, 31 mg, 0.78 mmol). The mixture is then stirred at room temperature for 18 h, and diluted with ethyl acetate. The organic layer is washed with water and saturated sodium chloride, dried over magnesium sulfate, and concentrated. The residue is chromatographed over silica gel, eluting with 20% ethyl acetate in hexanes. Concentration provides N-[5-chloro-3-methyl-6-(2,4,6-trifluorophenyl)[1,2,4]triazolo[1,5-a]pyrimidin-7(3H)-ylidene]-2,2,2-trifluoroethanamine as a white solid (76 mg). MS: m/z 396.0 (M+H).

Step C: 4-Chloro-6-[(2,2,2-trifluoroethyl)amino]-5-(2,4,6-trifluorophenyl)pyrimidin-2-yl(methyl)cyanamide To a solution of N-[5-chloro-3-methyl-6-(2,4,6-trifluorophenyl)[1,2,4]triazolo[1,5-a]pyrimidin-7(3H)-ylidene]-2,2,2-trifluoroethanamine (345 mg, 0.87 mmol) in 1 mL of dimethylsulfoxide at room temperature is added sodium hydride (60% in mineral oil, 35 mg, 0.87 mmol). The mixture is then stirred at room temperature for 2 h, and diluted with ethyl acetate. The organic layer is washed with water and saturated sodium chloride, dried over magnesium sulfate, and concentrated. The residue is chromatographed over silica gel, eluting with 10% ethyl acetate in hexanes. Concentration provides 4-chloro-6-[(2,2,2-trifluoroethyl)amino]-5-(2,4,6-trifluorophenyl)pyrimidin-2-yl(methyl)cyanamide as a white solid (157 mg). MS: m/z 396.1 (M+H).

Example 2 is synthesized analogously to Example 1.

EXAMPLE 2

4-Chloro-6-[(2,2,2-trifluoroethyl)amino]-5-(2,4,6-trifluorophenyl)pyrimidin-2-yl]ethylcyanamide; 410.0 (M+H)

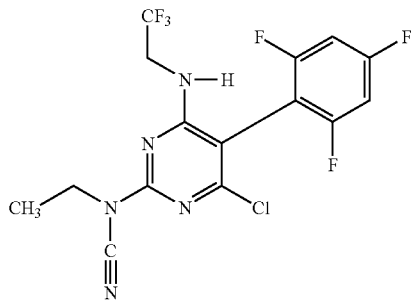

EXAMPLE 3

6-Chloro-2-pyrazin-2-yl-N-[(1S)-2,2,2-trifluoro-1-methylethyl]-5-(2,4,6-trifluorophenyl)pyrimidin-4-amine;

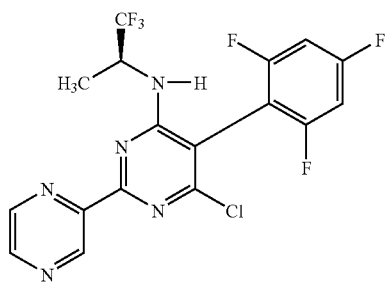

Step A: 2-Pyrazinecarboxamidine Hydrochloride

To 20 mL of methyl alcohol is added sodium (109 mg, 4.74 mmol) with stirring. After disappearance of the solid, 2-pyrazinecarbonitrile (5.0 g, 47.6 mmol) is added. The mixture is stirred at room temperature for 6 h, and ammonium chloride (2.8 g, 52.3 mmol) is added. The mixture is then stirred at room temperature for 18 h. Diethyl ether (50 mL) is added to the reaction mixture, and the precipitates are collected by filtration. The solid was washed with diethyl ether (×2) and dried in vacuum oven to give 2-pyrazinecarboxamidine hydrochloride as a white solid (6.5 g). MS: m/z 123.1 (M+H).

Alternatively, 2-pyrazinecarboxamidine hydrochloride can be prepared as follows: A solution of 2-pyrazinecarbonitrile (21 g, 200 mmol) in a mixture of 10 mL of methyl alcohol and 120 mL of diethyl ether is treated with hydrogen chloride gas at 0° C. The mixture is then stored at 5° C. for 3 days. The precipitates are collected by filtration and dried. This solid is then suspended in 100 mL of ethyl alcohol and the mixture is treated with ammonium gas at 0° C. The mixture is then stored at 5° C. for 4 days, and filtered. Concentration of the filtrate gives 2-pyrazinecarboxamidine hydrochloride as a tan solid (2.8 g).

Step B: 4,6-Dichloro-2-pyrazin-2-yl-5-(2,4,6-trifluorophenyl)pyrimidine

A mixture of diethyl 2-(2,4,6-trifluorophenyl)malonate (U.S. Pat. No. 6,156,925)(870 mg, 3.0 mmol), 2-pyrazinecarboxamidine hydrochloride (500 mg, 3.15 mmol), and 600 mg of tributylamine is stirred under nitrogen atmosphere at 180° C. for 1 h and cooled to room temperature. The mixture is cooled to room temperature and treated with 1.0 N hydrochloric acid. The precipitates are collected by filtration, washed with water and dried to give 2-pyrazin-2-yl-5-(2,4,6-trifluorophenyl)pyrimidine-4,6-diol as a tan solid (401 mg), which is used directly in the next step.

A mixture of 2-pyrazin-2-yl-5-(2,4,6-trifluorophenyl)pyrimidine-4,6-diol (401 mg) in 5 mL of phosphorous oxychloride and 1 mL of 2,6-lutidine is heated at 110° C. for 16 h. The excess phosphorous oxychloride is removed in vaccuo, and the resulting residue is dissolved in ethyl acetate. The organic layer is washed with water and saturated sodium chloride, dried over magnesium sulfate, and concentrated. The residue is chromatographed over silica gel, eluting with a gradient of 20% ethyl acetate in hexanes to 33% ethyl acetate in hexanes. Concentration provides 4,6-dichloro-2-pyrazin-2-yl-5-(2,4,6-trifluorophenyl)pyrimidine as a red solid (201 mg). MS: m/z 356.9 (M+H).

Step C: 6-Chloro-2-pyrazin-2-yl-N-[(1S)-2,2,2-trifluoro-1-methylethyl]-5-(2,4,6-trifluorophenyl)pyrimidin-4-amine A mixture of 4,6-dichloro-2-pyrazin-2-yl-5-(2,4,6-trifluorophenyl)pyrimidine (205 mg, 0.57 mmol), (1S)-2,2,2-trifluoro-1-methylethylamine hydrogen chloride (298 mg, 2 mmol), and N,N-diisopropylethylamine (258 mg, 2 mmol) in 5 mL of N,N-dimethylformamide is stirred at 90° C. in a sealed tube for 18 h. The reaction mixture is partitioned between ethyl acetate and saturated sodium chloride. The organic layer is washed with saturated sodium chloride (×3), dried over magnesium sulfate, and concentrated. The residue is chromatographed over silica gel, eluting with a gradient of 20% ethyl acetate in hexanes to 50% ethyl acetate in hexanes. Concentration provides 6-chloro-2-pyrazin-2-yl-N-[(1S)-2,2,2-trifluoro-1-methylethyl]-5-(2,4,6-trifluorophenyl)pyrimidin-4-amine as a light yellow solid (111 mg). MS: m/z 434.1 (M+H).

Examples 4-14 are synthesized analogously to Example 3.

EXAMPLE 4

6-Chloro-2-pyrazin-2-yl-N-(2,2,2-trifluoroethyl)-5-(2,4,6-trifluorophenyl)pyrimidin-4-amine; 419.9 (M+H)

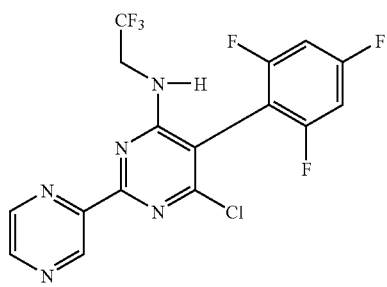

EXAMPLE 5

6-Chloro-N-(2,2,2-trifluoroethyl)-5-(2,4,6-trifluorophenyl)-2,2'-bipyrimidin-4-amine; 420.0 (M+H)

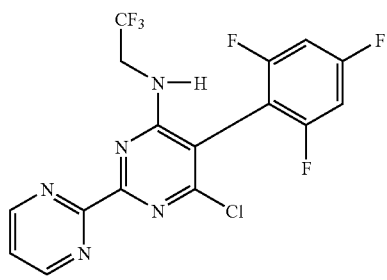

EXAMPLE 6

6-Chloro-2-pyridin-4-yl-N-(2,2,2-trifluoroethyl)-5-(2,4,6-trifluorophenyl)pyrimidin-4-amine; (419.0)

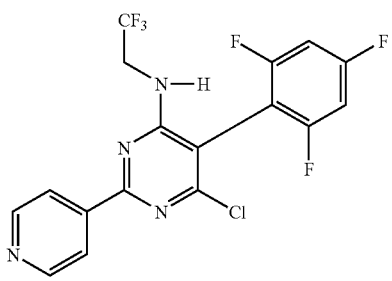

EXAMPLE 7

6-Chloro-2-pyridin-3-yl-N-(2,2,2-trifluoroethyl)-5-(2,4,6-trifluorophenyl)pyrimidin-4-amine; 419.1 (M+H)

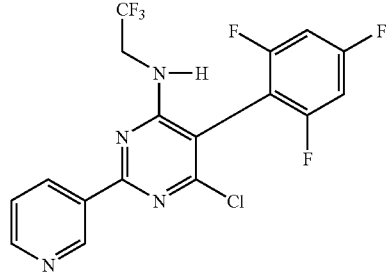

EXAMPLE 8

6-Chloro-2-pyridin-2-yl-N-(2,2,2-trifluoroethyl)-5-(2,4,6-trifluorophenyl)pyrimidin-4-amine; 419.0 (M+H)

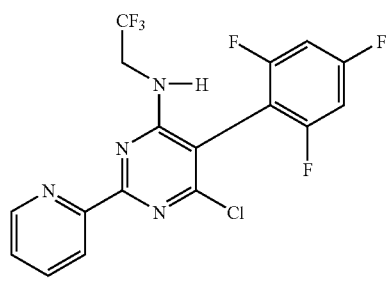

EXAMPLE 9

6-Chloro-2-pyridin-2-yl-N-[(1S)-2,2,2-trifluoro-1-methylethyl]-5-(2,4,6-trifluorophenyl)pyrimidin-4-amine; 433.0 (M+H)

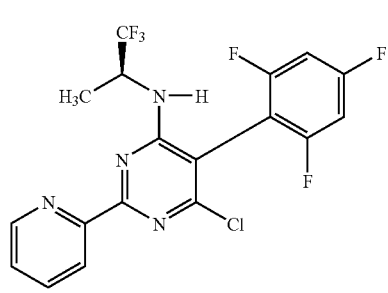

EXAMPLE 10

6-Chloro-2-quinolin-2-yl-N-(2,2,2-trifluoroethyl)-5-(2,4,6-trifluorophenyl)pyrimidin-4-amine; 469.0 (M+H)

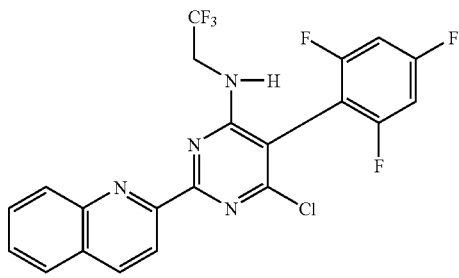

EXAMPLE 11

6-Chloro-2-isoquinolin-1-yl-N-(2,2,2-trifluoroethyl)-5-(2,4,6-trifluorophenyl)pyrimidin-4-amine; 469.0 (M+H)

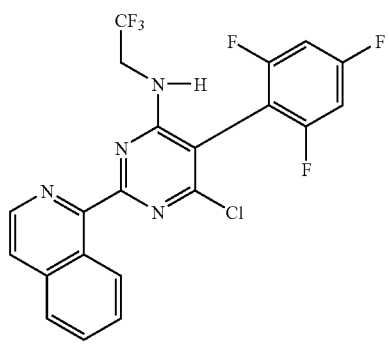

EXAMPLE 12

6-Chloro-2-isoquinolin-3-yl-N-(2,2,2-trifluoroethyl)-5-(2,4,6-trifluorophenyl)pyrimidin-4-amine; 469.0 (M+H)

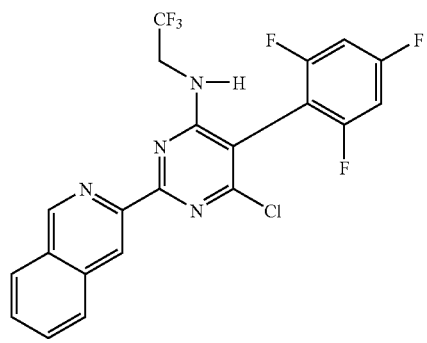

EXAMPLE 13

6-Chloro-2-thien-2-yl-N-(2,2,2-trifluoroethyl)-5-(2,4,6-trifluorophenyl)pyrimidin-4-amine; 424.0 (M+H)

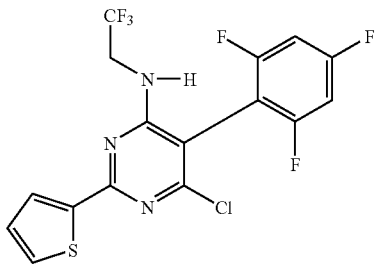

EXAMPLE 14

6-Chloro-2-(2-furyl)-N-(2,2,2-trifluoroethyl)-5-(2,4,6-trifluorophenyl)pyrimidin-4-amine; 408.0 (M+H)

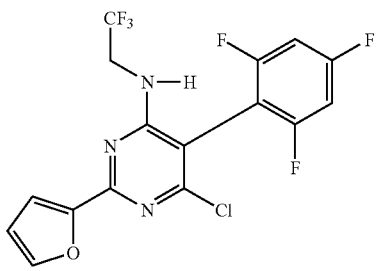

EXAMPLE 15

6-Chloro-2-(1H-imidazol-1-yl)-N-(2,2,2-trifluoroethyl)-5-(2,4,6-trifluorophenyl)pyrimidin-4-amine;

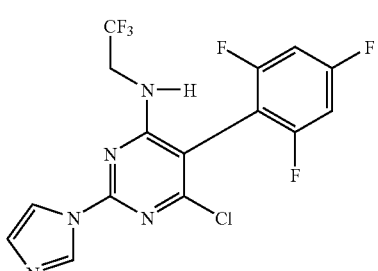

Step A:
5-(2,4,6-Trifluorophenyl)pyrimidine-2,4,6-triol

To a mixture of diethyl 2-(2,4,6-trifluorophenyl)malonate (580 mg, 2.0 mmol, U.S. Pat. No. 6,156,925) and urea (360 mg, 6.0 mmol) in 10 mL of ethyl alcohol at room temperature is added sodium hydride (60% in mineral oil, 160 mg, 4.0 mmol). The mixture is then heated at 80° C. for 3 days, cooled to room temperature, and partitioned between ethyl acetate and 1N hydrochloric acid. The aqueous layer is extracted with ethyl acetate, and the combined organic extracts are dried over magnesium sulfate, and concentrated. The residue is chromatographed over silica gel, eluting with a gradient of ethyl acetate to 10% methyl alcohol in ethyl acetate. Concentration provides 5-(2,4,6-trifluorophenyl)pyrimidine-2,4,6-triol as a light tan solid (148 mg). MS: m/z 257.0 (M–H).

Step B: 4,6-Dichloro-2-(1H-imidazol-1-yl)-5-(2,4,6-trifluorophenyl)pyrimidine

A mixture of 5-(2,4,6-trifluorophenyl)pyrimidine-2,4,6-triol (258 mg, 1.0 mmol) in 2.5 mL of phosphorous oxychloride and 0.5 mL of 2,6-lutidine is heated at 110° C. for 16 h. The excess phosphorous oxychloride is removed in vaccuo, and the resulting residue is dissolved in a 1:1 mixture of methylene chloride and hexanes. The organic layer is filtered through hydrous magnesium silicate, and the filtrate is concentrated to provide crude 2,4,6-trichloro-5-(2,4,6-trifluorophenyl)pyrimidine as a dark solid (104 mg).

A mixture of the above 2,4,6-trichloro-5-(2,4,6-trifluorophenyl)pyrimidine (104 mg), imidazole (23 mg, 0.33 mmol), and potassium carbonate (92 mg, 0.66 mmol) in 2 mL of N,N-dimethylformamide is stirred at room temperature for 3 h. The mixture is partitioned between ethyl acetate and saturated sodium chloride. The organic layer is washed with saturated sodium chloride (×4), dried over magnesium sulfate, and concentrated. The residue is chromatographed over silica gel, eluting with a gradient of hexanes to 50% ethyl acetate in hexanes. Concentration provides 4,6-dichloro-2-(1H-imidazol-1-yl)-5-(2,4,6-trifluorophenyl)pyrimidine as a tan solid (71 mg, mp 72-74° C.). MS: m/z 345.2 (M+H).

Step C: 6-Chloro-2-(1H-imidazol-1-yl)-N-(2,2,2-trifluoroethyl)-5-(2,4,6-trifluorophenyl)pyrimidin-4-amine A solution of 4,6-dichloro-2-(1H-imidazol-1-yl)-5-(2,4,6-trifluorophenyl)pyrimidine (35 mg, 0.10 mmol) and 2,2,2-trifluoroethylamine (50 mg, 0.5 mmol) in 2 mL of N,N-dimethylformamide is stirred at room temperature for 1 h. A saturated sodium chloride solution is added, and the product is extracted with ehtyl acetate. The organic solution is washed with saturated sodium chloride (×4), dried over magnesium sulfate, and concentrated. The residue is chromatographed over silica gel, eluting with a gradient of 20% ethyl acetate in hexanes to 50% ethyl acetate in hexanes. Concentration provides 6-chloro-2-(1H-imidazol-1-yl)-N-(2,2,2-trifluoroethyl)-5-(2,4,6-trifluorophenyl)pyrimidin-4-amine as a light tan solid (36 mg, mp 168-170° C.). MS: m/z 408.2 (M+H).

Examples 16-18 are synthesized analogously to Example 15.

EXAMPLE 16

6-Chloro-2-(1H-pyrazol-1-yl)-N-(2,2,2-trifluoroethyl)-5-(2,4,6-trifluorophenyl)pyrimidin-4-amine; 407.9 (M+H)

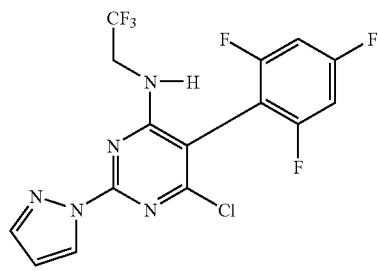

EXAMPLE 17

6-Chloro-2-(1H-pyrazol-1-yl)-N-[(1S)-2,2,2-trifluoro-1-methylethyl]-5-(2,4,6-trifluorophenyl)pyrimidin-4-amine; 422.0 (M+H)

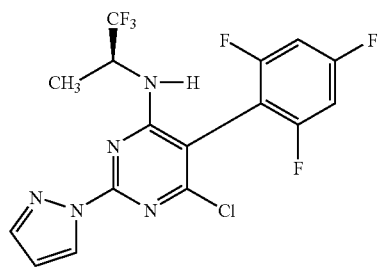

EXAMPLE 18

6-Chloro-2-(1H-pyrrol-1-yl)-N-(2,2,2-trifluoroethyl)-5-(2,4,6-trifluorophenyl)pyrimidin-4-amine; 407.1 (M+H)

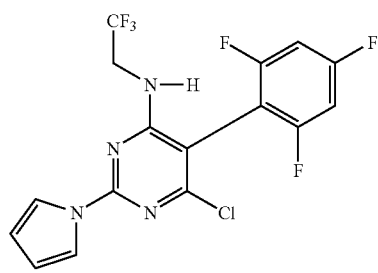

EXAMPLE 19

4-Chloro-5-{4-[3-(dimethylamino)propoxy]-2,6-difluorophenyl}-6-[(2,2,2-trifluoroethyl)amino]pyrimidin-2-yl(methyl)cyanamide;

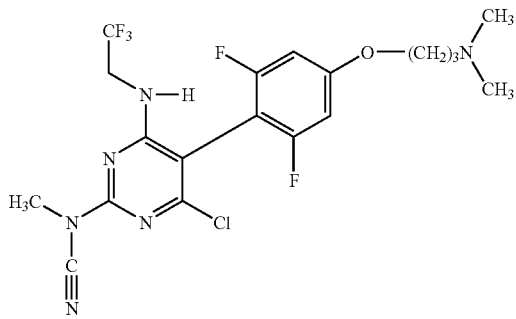

To a stirred mixture of sodium hydride (60% in mineral oil, 12 mg, 0.30 mmol) in 2 mL of dimethylsulfoxide is added 3-dimethylamino-1-propanol (27 μL, 0.23 mmol). The mixture is then stirred at room temperature for 1 h. 4-Chloro-6-[(2,2,2-trifluoroethyl)amino]-5-(2,4,6-trifluorophenyl)pyrimidin-2-yl(methyl)cyanamide (60 mg, 0.152 mmol) is then added, and the reaction mixture is heated at 60° C. for 4 h, and diluted with ethyl acetate. The organic layer is washed with water and saturated sodium chloride, dried over magnesium sulfate, and concentrated. The residue is chromatographed over silica gel, eluting with a gradient of ethyl acetate to 50% methyl alcohol in ethyl acetate to methyl alcohol. Concentration provides 4-chloro-5-{4-[3-(dimethylamino)propoxy]-2,6-difluorophenyl}-6-[(2,2,2-trifluoroethyl)amino]pyrimidin-2-yl(methyl)cyanamide as a light yellow semisolid solid (20 mg). MS: m/z 479.3(M+H).

EXAMPLE 19a

4-Chloro-5-{4-[3-(dimethylamino)propoxy]-2,6-difluorophenyl}-6-[(2,2,2-trifluoroethyl)amino]pyrimidin-2-yl(methyl)cyanamide hydrogen chloride 4-Chloro-5-{4-[3-(dimethylamino)propoxy]-2,6-difluorophenyl}-6-[(2,2,2-trifluoroethyl)amino]pyrimidin-2-yl(methyl)cyanamide (165 mg) is dissolved in methylene chloride and filtered. To the filtrate is bubbled hydrogen chloride gas. Concentration provides hydrogen chloride salt as a red solid (170 mg).

EXAMPLE 20

6-Chloro-5-{4-[3-(dimethylamino)propoxy]-2,6-difluorophenyl}-N²-methyl-N⁴-(2,2,2-trifluoroethyl)pyrimidine-2,4-diamine;

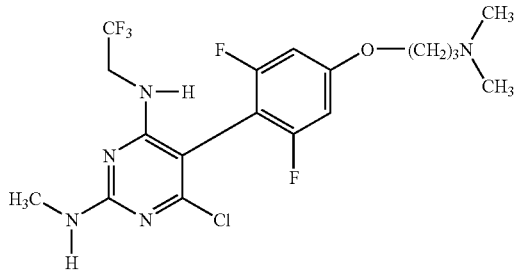

EXAMPLE 20a

6-Chloro-5-{4-[3-(dimethylamino)propoxy]-2,6-difluorophenyl}-N²-methyl-N⁴-(2,2,2-trifluoroethyl)pyrimidine-2,4-diamine trifluoroacetic acid salt

EXAMPLE 19b

4-Chloro-5-{4-[3-(dimethylamino)propoxy]-2,6-difluorophenyl}-6-[(2,2,2-trifluoroethyl)amino]pyrimidin-2-yl(methyl)cyanamide trifluoroacetic acid salt To a stirred mixture of sodium hydride (60% in mineral oil, 308 mg, 7.7 mmol) in 10 mL of dimethylsulfoxide is added 3-dimethylamino-1-propanol (0.91 mL, 7.7 mmol). The mixture is then stirred at room temperature for 1 h. 4-Chloro-6-[(2,2,2-trifluoroethyl)amino]-5-(2,4,6-trifluorophenyl)pyrimidin-2-yl(methyl)cyanamide (762 mg, 1.93 mmol) is then added, and the reaction mixture is heated at 90° C. for 1 h, and diluted with ethyl acetate. The organic layer is washed with water and saturated sodium chloride, dried over magnesium sulfate, and concentrated. The residue is chromatographed over silica gel, eluting with a gradient of ethyl acetate to 50% methyl alcohol in ethyl acetate to methyl alcohol. Concentration provides a light yellow solid, which is further purified by HPLC to yield 6-chloro-5-{4-[3-(dimethylamino)propoxy]-2,6-difluorophenyl}-N²-methyl-N⁴-(2,2,2-trifluoroethyl)pyrimidine-2,4-diamine trifluoroacetic acid salt as a white solid (8 mg), MS: m/z 454.3(M+H) and 4-chloro-5-{4-[3-(dimethylamino)propoxy]-2,6-difluorophenyl}-6-[(2,2,2-trifluoroethyl)amino]pyrimidin-2-yl(methyl)cyanamide trifluoroacetic acid salt as a white solid (50 mg), MS: m/z 479.3(M+H).

Examples 21-23 are synthesized analogously to Example 19.

EXAMPLE 21

(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide; 493.2 (M+H)

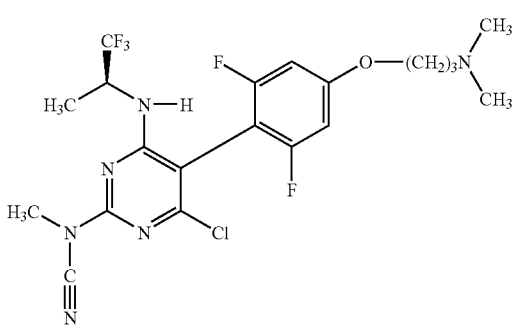

EXAMPLE 21a (4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide hydrochloride; 493.2 (M+H)

EXAMPLE 22

4-Chloro-5-{4-[2-(dimethylamino)ethoxy]-2,6-difluorophenyl}-6-[(2,2,2-trifluoroethyl)amino]pyrimidin-2-yl(methyl)cyanamide; 465.2 (M+H)

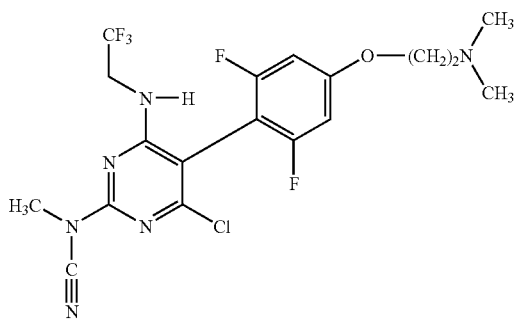

EXAMPLE 23

{4-Chloro-5-{4-[4-(dimethylamino)butoxy]-2,6-difluorophenyl}-6-[(2,2,2-trifluoroethyl)amino]pyrimidin-2-yl}methylcyanamide; 493.2 (M+H)

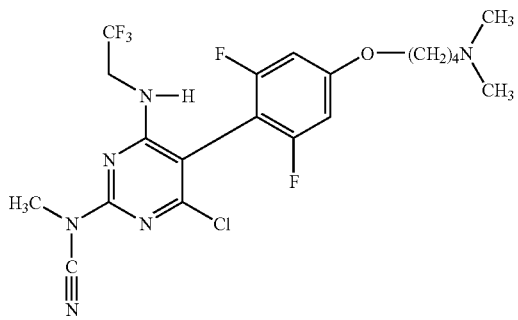

EXAMPLE 24

6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine

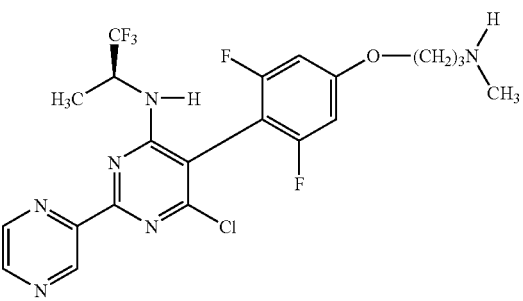

To a solution of 6-chloro-2-pyrazin-2-yl-N-[(1S)-2,2,2-trifluoro-1-methylethyl]-5-(2,4,6-trifluorophenyl)pyrimidin-4-amine (251 mg, 0.58 mmol) and 3-(methylamino)propan-1-ol (267 mg, 3.0 mmol) in 3 mL of dimethylsulfoxide at room temperature is added sodium hydride (60% in mineral oil, 120 mg, 3.0 mmol). The mixture is stirred at 60° C. for 2 h, cooled to room temperature, and partitioned between ethyl acetate and saturated sodium chloride. The organic layer is washed with saturated sodium chloride (×3), dried over magnesium sulfate, and concentrated. The residue is chromatographed over silica gel, eluting with a gradient of ethyl acetate to 50% methyl alcohol in ethyl acetate. Concentration provides 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine as a light tan solid (181 mg, mp 48-50° C.). MS: m/z 503.1 (M+H).

EXAMPLE 24a

6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine hygrogen chloride The product thus obtained is dissolved in methylene chloride and filtered. To the filtrate is bubbled hydrogen chloride gas. Concentration provides hydrogen chloride salt as a red solid (210 mg).

Examples 25-30 are synthesized analogously to Example 24.

EXAMPLE 25

6-Chloro-5-{4-[3-(dimethylamino)propoxy]-2,6-difluorophenyl}-2-pyrazin-2-yl-N-(2,2,2-trifluoroethyl)pyrimidin-4-amine; 503.0 (M+H)

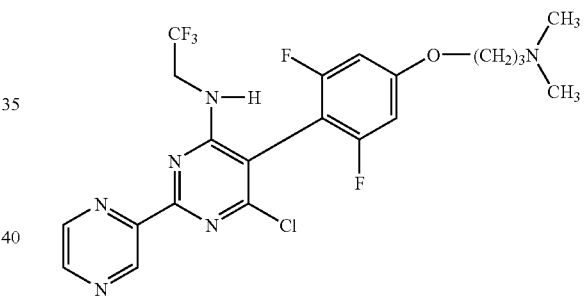

EXAMPLE 25a

6-Chloro-5-{4-[3-(dimethylamino)propoxy]-2,6-difluorophenyl}-2-pyrazin-2-yl-N-(2,2,2-trifluoroethyl)pyrimidin-4-amine hygrogen chloride; 503.0 (M+H)

EXAMPLE 26

6-Chloro-5-{4-[3-(dimethylamino)propoxy]-2,6-difluorophenyl}-N-(2,2,2-trifluoroethyl)-2,2'-bipyrimidin-4-amine; 503.1 (M+H)

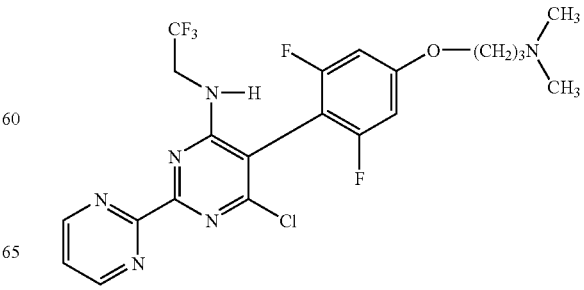

EXAMPLE 27

6-Chloro-5-{4-[2-(dimethylamino)ethoxy]-2,6-difluorophenyl}-2-pyrazin-2-yl-N-(2,2,2-trifluoroethyl)pyrimidin-4-amine; 489.2 (M+H)

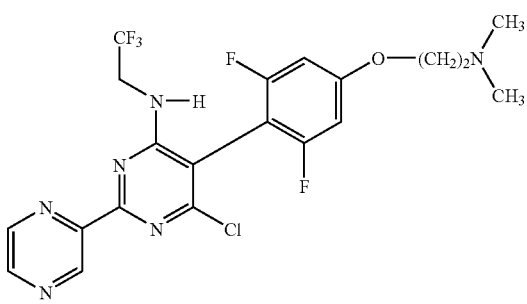

EXAMPLE 28

6-Chloro-5-{4-[4-(dimethylamino)butoxy]-2,6-difluorophenyl}-2-pyrazin-2-yl-N-(2,2,2-trifluoroethyl)pyrimidin-4-amine; 517.2 (M+H)

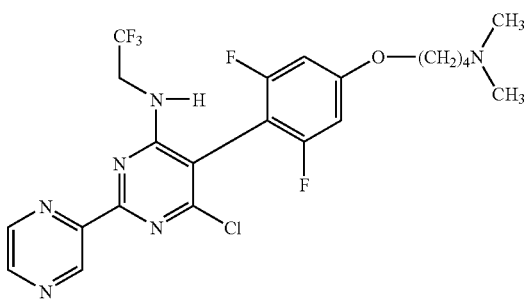

EXAMPLE 29

6-Chloro-5-{2,6-difluoro-4-[3-(methylamino)propoxy]phenyl}-2-pyridin-2-yl-N-[(S)-2,2,2-trifluoro-1-methylethyl]pyrimidin-4-amine; 502.1 (M+H)

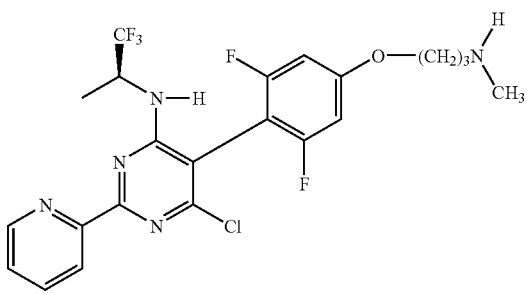

EXAMPLE 29a

6-Chloro-5-{2,6-difluoro-4-[3-(methylamino)propoxy]phenyl}-2-pyridin-2-yl-N-[(S)-2,2,2-trifluoro-1-methylethyl]pyrimidin-4-amine hydrogen chloride

EXAMPLE 30

6-Chloro-5-{4-[3-(dimethylamino)propoxy]-2,6-difluorophenyl}-2-quinolin-2-yl-N-(2,2,2-trifluoroethyl)pyrimidin-4-amine; 552.1 (M+H)

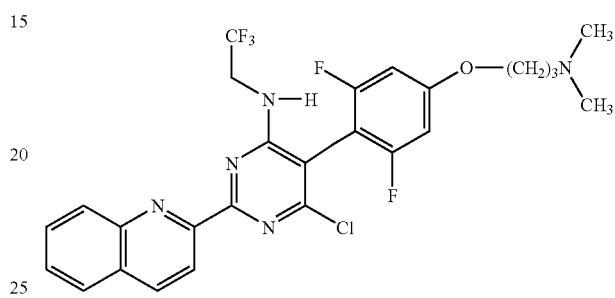

EXAMPLE 31

6-Chloro-5-{4-[3-(dimethylamino)propoxy]-2,6-difluorophenyl}-2-(1H-imidazol-1-yl)-N-(2,2,2-trifluoroethyl)pyrimidin-4-amine

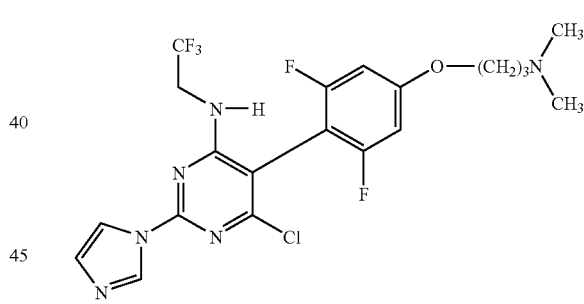

To a solution of 6-chloro-2-(1H-imidazol-1-yl)-N-(2,2,2-trifluoroethyl)-5-(2,4,6-trifluorophenyl)pyrimidin-4-amine (20 mg, 0.05 mmol) and 3-dimethylamino-1-propanol (103 mg, 1.0 mmol) in 3 mL of dimethylsulfoxide at room temperature is added sodium hydride (60% in mineral oil, 40 mg, 1.0 mmol). The mixture is stirred at 60° C. for 2 h, cooled to room temperature, and partitioned between ethyl acetate and saturated sodium chloride. The organic layer is washed with saturated sodium chloride (×3), dried over magnesium sulfate, and concentrated. The residue is chromatographed over silica gel, eluting with a gradient of ethyl acetate to 50% methyl alcohol in ethyl acetate. Concentration provides 6-chloro-5-{4-[3-(dimethylamino)propoxy]-2,6-difluorophenyl}-2-(1H-imidazol-1-yl)-N-(2,2,2-trifluoroethyl)pyrimidin-4-amine as a light tan solid (16 mg, mp 47-49° C.). MS: m/z 491.1 (M+H).

Example 32 is synthesized analogously to Example 24 and 31.

EXAMPLE 32

6-Chloro-5-{2,6-difluoro-4-[3-(methylamino)propoxy]phenyl}-2-(1H-pyrazol-1-yl)-N-[(1S)-2,2,2-trifluoro-1-methylethyl)pyrimidin-4-amine; 491.0 (M+H)

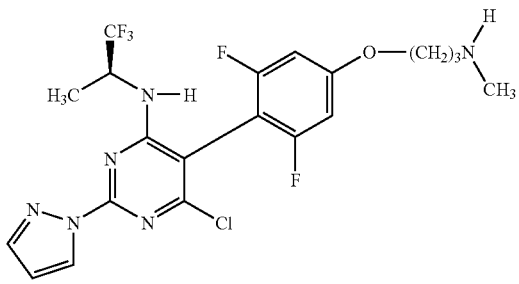

EXAMPLE 32a

6-Chloro-5-{2,6-difluoro-4-[3-(methylamino)propoxy]phenyl}-2-(1H-pyrazol-1-yl)-N-[(1S)-2,2,2-trifluoro-1-methylethyl)pyrimidin-4-amine Hydrogen Chloride; 491.0 (M+H)

EXAMPLE 33

N-{3-[4-(4-Chloro-6-cycloheptyl-2-pyrazin-2-ylpyrimidin-5-yl)-3,5-difluorophenoxy]propyl}-N-methylamine

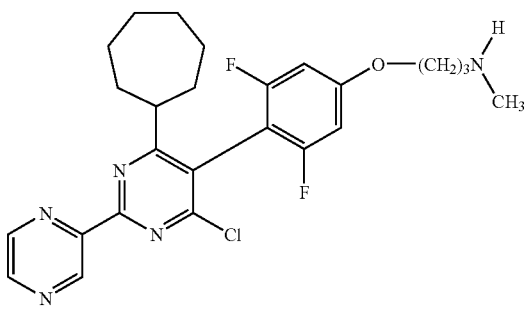

EXAMPLE 33a

N-{3-[4-(4-Chloro-6-cycloheptyl-2-pyrazin-2-ylpyrimidin-5-yl)-3,5-difluorophenoxy]propyl}-N-methylamine trifluoroacetic acide salt

Step A: Ethyl 3-cycloheptyl-3-oxo-2-(2,4,6-trifluorophenyl)propanoate

A mixture of 2,4,6-trifluorophenylacetic acid (570 mg, 3.0 mmol), iodoethane (1.56 g, 10 mmol), and potassium carbonate (1.38 g, 10 mmol) in 5 mL of dimethylsulfoxide is stirred at 50° C. for 3 h, and cooled to room temperature. The mixture is partitioned between diethyl ether and water. The organic layer is washed with water, and saturated sodium chloride, dried over magnesium sulfate, and filtered through hydrous magnesium silicate. The filtrate is concentrated to give ethyl 2,4,6-trifluorophenylacetate as a light yellow oil (581 mg, 2.66 mmol).

A mixture of cycloheptanecarboxylic acid (5.0 g, 35.2 mmol) in 25 mL of thionyl chloride is refluxed for 1 h, and concentrated. The crude cycloheptanecarboxylic acid chloride thus obtained is used directly in the next step.

A solution of ethyl 2,4,6-trifluorophenylacetate (436 mg, 2.0 mmol) in 3 mL of tetrahydrofuran is cooled to −78° C., and lithium diisopropylamide (2.0 M in heptane/tetrahydrofuran/ethylbenzene, 1.0 mL, 2.0 mmol) is added dropwise with stirring. The mixture is stirred at −78° C. for 1 h, and cycloheptanecarboxylic acid chloride (321 mg, 2.0 mmol) is added dropwise. The mixture is warmed to room temperature and acidified with 2 mL of 1.0 N hydrochloric acid. The product is extracted with ethyl acetate. The organic layer is washed with saturated sodium chloride, dried over magnesium sulfate, and concentrated. The residue is chromatographed over silica gel, eluting with a gradient of hexanes to 10% ethyl acetate in hexanes. Concentration provides ethyl 3-cycloheptyl-3-oxo-2-(2,4,6-trifluorophenyl)propanoate as a colorless oil (410 mg). MS: m/z 341.2 (M−H).

Step B: 6-Cycloheptyl-2-pyrazin-2-yl-5-(2,4,6-trifluorophenyl)pyrimidin-4-ol A mixture of ethyl 3-cycloheptyl-3-oxo-2-(2,4,6-trifluorophenyl)propanoate (649 mg, 1.9 mmol) and 2-pyrazinecarboxamidine hydrochloride (452 mg, 2.85 mmol) in 1.5 mL of tributylamine is stirred under nitrogen atmosphere at 160° C. for 4 h. The mixture is cooled to room temperature and the excess of tributylamine is decanted off. The residue is washed with hexanes and chromatographed over silica gel, eluting with 10% methanol in ethyl acetate. Concentration provides 6-cycloheptyl-2-pyrazin-2-yl-5-(2,4,6-trifluorophenyl)pyrimidin-4-ol as a light yellow solid. MS: m/z 401.2 (M+H).

Step C: Tert-Butyl {3-[4-(4-cycloheptyl-6-hydroxy-2-pyrazin-2-ylpyrimidin-5-yl)-3,5-difluorophenoxy]propyl}methylcarbamate To a mixture of sodium hydride (60% in mineral oil, 102 mg, 2.55 mmol) in 4 mL of dimethylsulfoxide at room temperature is added 3-(methylamino)propan-1-ol (224 mg, 2.51 mmol). The mixture is stirred at room temperature for 1 h, and 6-cycloheptyl-2-pyrazin-2-yl-5-(2,4,6-trifluorophenyl)pyrimidin-4-ol (336 mg, 0.84 mmol) is added. The mixture is stirred at 60° C. for 14 h, and cooled to room temperature. Di-tert-butyl dicarbonate (550 mg, 2.5 mmol) is added, and the mixture is stirred at room temperature for 16 h. The mixture is diluted with ethyl acetate. The organic layer is washed with water and saturated sodium chloride, dried over magnesium sulfate, and concentrated. The residue is chromatographed over silica gel, eluting with 10% methanol in ethyl acetate. Concentration provides tert-butyl {3-[4-(4-cycloheptyl-6-hydroxy-2-pyrazin-2-ylpyrimidin-5-yl)-3,5-difluorophenoxy]propyl}methylcarbamate as a light yellow solid (320 mg). MS: m/z 570.3 (M+H).

Step D: N-{3-[4-(4-Chloro-6-cycloheptyl-2-pyrazin-2-ylpyrimidin-5-yl)-3,5-difluorophenoxy]propyl}-N-methylamine To tert-butyl {3-[4-(4-cycloheptyl-6-hydroxy-2-pyrazin-2-ylpyrimidin-5-yl)-3,5-difluorophenoxy]propyl}methylcarbamate (130 mg, 0.23 mmol) is added 2.0 mL of phosphorous oxychloride and 1.0 mL of 2,6-lutidine, and the mixture is heated at 110° C. for 12 h. The excess phosphorous oxychloride is removed in vaccuo, and the resulting residue is chromatographed over silica gel, eluting with 30% ethyl acetate in hexanes. Concentration provides tert-butyl {3-[4-(6-chloro-4-cycloheptyl-2-pyrazin-2-ylpyrimidin-5-yl)-3,5-difluorophenoxy]propyl}methylcarbamate as a light yellow semi-solid (23 mg). MS: m/z 588.0 (M+H). This product is dissolved in 2 mL of methylene chloride, and 2.3 mL of trifluoroacetic acid is added. The mixture is stirred at 40° C. for 20 h, and concentrated in vaccuo, yielding N-{3-[4-(4-chloro-6-cycloheptyl-2-pyrazin-2-ylpyrimidin-5-yl)-3,5-difluorophenoxy]propyl}-N-methylamine as a trifluoroacetic acid salt as a light yellow semi-solid (24 mg). MS: m/z 488.2 (M+H).

Examples 34-37 are synthesized analogously to Example 3.

EXAMPLE 34

6-Chloro-2-(1-methyl-1H-imidazol-2-yl)-N-(2,2,2-trifluoroethyl)-5-(2,4,6-trifluorophenyl)pyrimidin-4-amine; 422.0 (M+H)

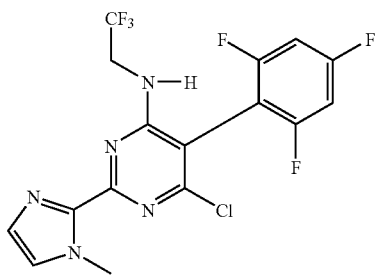

Step A: 1-Methyl-2-imidazole Carbonitrile

1-Methyl-2-imidazole carboxaldehyde (1.7 g, 15.4 mmol) is stirred in 10 mL of methyl alcohol. N,N-Dimethylhydrazine (1.4 g, 23.3 mmol) is then added. The mixture is stirred for 5 h, and the resulting hydrazone solution is added dropwise into a solution of magnesium monoperoxyphtalate hexahydrate (23.9 g, 80%, 38.6 mmol) in 20 mL of methyl alcohol at 0° C. The resulting reaction mixture is allowed to warm to room temperature overnight and concentrated. The residue is diluted with water, then extracted with methylene chloride (×3). The combined organic is washed with saturated sodium chloride, dried over magnesium sulfate and concentrated. The residue is chromatographed, eluting with 40% ethyl acetate in hexanes to give 1-methyl-2-imidazole carbonitrile as a yellow oil.

Step B: 1-Methyl-2-imidazole carboxamidine hydrochloride

To 10 mL of methyl alcohol in a sealed tube is added sodium hydride (440 mg, 11 mmol) with stirring. 1-Methyl-2-imidazole carbonitrile (1.18 g, 11 mmol) is added. The mixture is stirred at room temperature for 20 h, and ammonium chloride (588 mg, 11 mmol) is added. The bottle is then sealed and stirred at 80° C. for 8 h, and cooled to room temperature. The mixture is filtered, and the filtrate is concentrated. The residue is treated with 1% methyl alcohol in diethyl ether, and the precipitates are collected by filtration and dried to give 1-methyl-2-imidazole carboxamidine hydrochloride as a gray solid (1.6 g). MS: m/z 125.2 (M+H).

EXAMPLE 35

6-Chloro-2-(1H-pyrrol-2-yl)-N-(2,2,2-trifluoroethyl)-5-(2,4,6-trifluorophenyl)pyrimidin-4-amine; 407.0 (M+H)

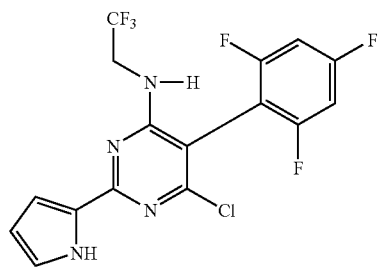

EXAMPLE 36

6-Chloro-2-(4-methylpyridin-2-yl)-N-(2,2,2-trifluoroethyl)-5-(2,4,6-trifluorophenyl)pyrimidin-4-amine; 433.0 (M+H)

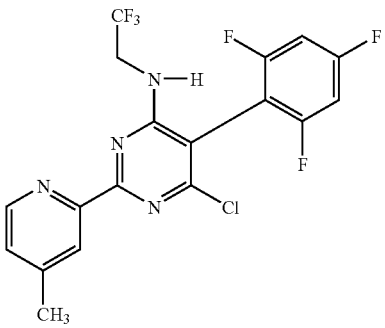

EXAMPLE 37

6-Chloro-2-(5-nitropyridin-2-yl)-N-(2,2,2-trifluoroethyl)-5-(2,4,6-trifluorophenyl)pyrimidin-4-amine; 464.0 (M+H)

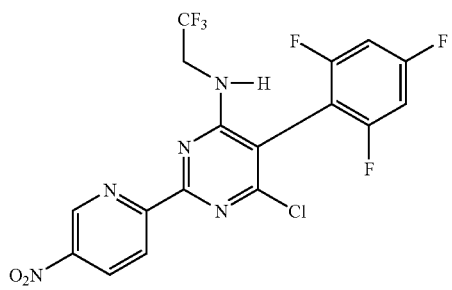

EXAMPLE 38

2-(5-Azidopyridin-2-yl)-6-chloro-5-{4-[3-(dimethylamino)propoxy]-2,6-difluorophenyl}-N-(2,2,2-trifluoroethyl)pyrimidin-4-amine

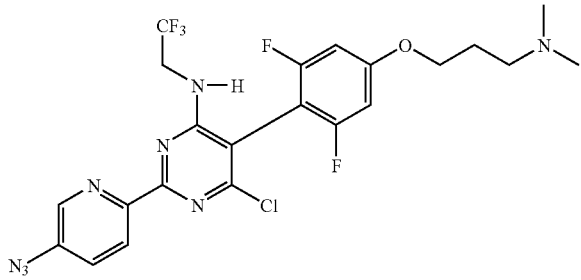

Step A: 2-(5-Aminopyridin-2-yl)-6-chloro-N-(2,2,2-trifluoroethyl)-5-(2,4,6-trifluorophenyl)pyrimidin-4-amine A mixture of 6-chloro-2-(5-nitropyridin-2-yl)-N-(2,2,2-trifluoroethyl)-5-(2,4,6-trifluorophenyl)pyrimidin-4-amine (101 mg, 0.22 mmol) and Iron powder (256 mg, 4.58 mmol) in 2 mL of methyl alcohol and 1 mL of acetic acid is heated at 100° C. for 1 h. The reaction mixture is cooled to room temperature and diluted with ethyl acetate. The organic layer is washed with saturated sodium bicarbonate and then with saturated sodium chloride, dried over magnesium sulfate, filtered, concentrated and dried under reduced pressure to yield 2-(5-aminopyridin-2-yl)-6-chloro-N-(2,2,2-trifluoroethyl)-5-(2,4,6-trifluorophenyl)pyrimidin-4-amine as a light yellow oil (100 mg). MS: m/z 434.2 (M+H). This product is used in the next step with out further purification.

Sep B: 2-(5-Aminopyridin-2-yl)-6-chloro-5-{4-[3-(dimethylamino)propoxy]-2,6-difluorophenyl}-N-(2,2,2-trifluoroethyl)pyrimidin-4-amine To a mixture of sodium hydride (33.6 mg, 0.84 mmol) in 2 mL of dimethylsulfide is added N,N-Dimethylaminopropan-1-ol (99 µL, 0.84 mmol) slowly. After 30 minutes, 2-(5-aminopyridin-2-yl)-6-chloro-N-(2,2,2-trifluoroethyl)-5-(2,4,6-trifluorophenyl)pyrimidin-4-amine (100 mg, from Step A) is added and the resulting reaction mixture is heated at 60° C. for 4 h. The reaction mixture is cooled to room temperature, and diluted with ethyl acetate. The organic layer is washed with water and then with saturated sodium chloride solution, dried over magnesium sulfate, filtered, concentrated and dried under reduced pressure to yield 2-(5-aminopyridin-2-yl)-6-chloro-5-{4-[3-(dimethylamino)propoxy]-2,6-difluorophenyl}-N-(2,2,2-trifluoroethyl)pyrimidin-4-amine as a yellow semi-solid (60 mg). MS: m/z 517.3 (M+H). This product was used in the next step without further purification.

What is claimed is:

1. A compound of Formula (I)

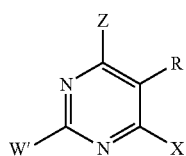

(I)

wherein:

Z is selected from:

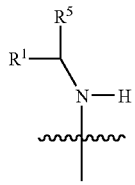

and $C_6$-$C_8$ cycloalkyl;

R is a moiety

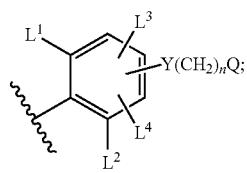

n is an integer of 2, 3, or 4;

$L^1$ and $L^2$, are each independently H, F, Cl or Br;

$L^3$ and $L^4$ are H;

X is Cl or Br;

Y is O, S, or —$NR^2$;

Q is OH or —$NR^3R^4$;

$R^1$ is H or $C_1$-$C_3$ alkyl;

$R^2$ is H or $C_1$-$C_3$ alkyl;

$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;

$R^5$ is $CF_3$ or $C_2F_5$;

W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

$R^6$ is $C_1$-$C_3$ alkyl;

$R^7$ is $C_1$-$C_3$ alkyl;

or a pharmaceutically acceptable salt thereof.

2. A compound according to claim 1, wherein Formula (I) is represented by formula (Ia)

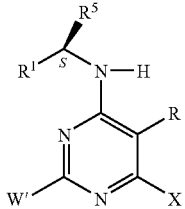

(Ia)

or pharmaceutically acceptable salts thereof.

3. A compound according to claim 1, wherein Formula (I) is represented by formula (Ib)

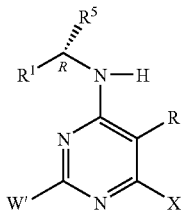

(Ib)

or pharmaceutically acceptable salts thereof.

4. A compound according to claim 1 wherein R is

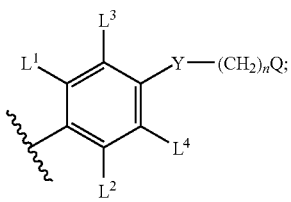

or pharmaceutically acceptable salts thereof.

5. A compound according to claim 1 wherein Z is $C_6$-$C_8$ cycloalkyl or pharmaceutically acceptable salts thereof.

6. A compound according to claim 2 wherein
R is the moiety:

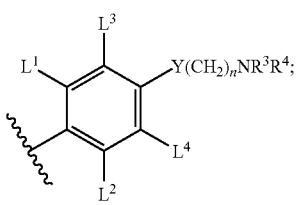

n=3;
$R^1$ is H or methyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$;
$R^7$ is $C_1$-$C_3$ alkyl;
$L^1$ is F;
$L^2$ is F;
$L^3$ is H;
$L^4$ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups
or pharmaceutically acceptable salts thereof.

7. A compound according to claim 3 wherein:
R is the moiety:

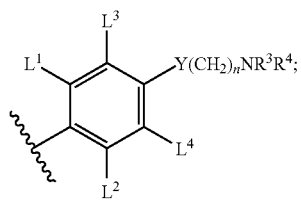

n=3;
$R^1$ is H or methyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$;
$R^7$ is $C_1$-$C_3$ alkyl;
$L^1$ is F;
$L^2$ is F;
$L^3$ is H;
$L^4$ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups
or pharmaceutically acceptable salts thereof.

8. A compound according to claim 5 wherein
R is the moiety:

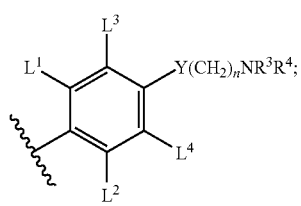

n=3;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^7$ is $C_1$-$C_3$ alkyl;
$L^1$ is F;
$L^2$ is F;

L³ is H;
L⁴ is H;
X is Cl;
Y is O;
W' is N-methylamino, N-methylcyanamido, 1-pyrazolyl, 2-pyrazinyl, 2-pyridyl, 2-pyrimidinyl, or 3-isoquinolinyl groups
or pharmaceutically acceptable salts thereof.

9. The compound according to claim 1, 4-chloro-5-{4-[3-(dimethylamino)propoxy]-2,6-difluorophenyl}-6-[(2,2,2-trifluoroethyl)amino]pyrimidin-2-yl(methyl)cyanamide or pharmaceutically acceptable salts thereof.

10. The compound according to claim 1, 6-chloro-5-{4-[3-(dimethylamino)propoxy]-2,6-difluorophenyl}-N²-methyl-N⁴-(2,2,2-trifluoroethyl)pyrimidine-2,4-diamine or pharmaceutically acceptable salt thereof.

11. The compound according to claim 1, (4-chloro-5-{4-[3-(dimethylamino)propoxy]-2,6-difluorophenyl}-6-{[2,2,2-trifluoro-1-methylethyl]amino}pyrimidin-2-yl)methylcyanamide or pharmaceutically acceptable salts thereof.

12. The compound according to claim 1, 4-chloro-5-{4-[2-(dimethylamino)ethoxy]-2,6-difluorophenyl}-6-[(2,2,2-trifluoroethyl)amino]pyrimidin-2-yl(methyl)cyanamide or pharmaceutically acceptable salts thereof.

13. The compound according to claim 1, {4-chloro-5-{4-[4-(dimethylamino)butoxy]-2,6-difluorophenyl}-6-[(2,2,2-trifluoroethyl)amino]pyrimidin-2-yl}methylcyanamide or pharmaceutically acceptable salts thereof.

14. The compound according to claim 1, 6-chloro-5-{2,6-difluoro-4-[3-(methylamino)propoxy]phenyl}-2-pyrazin-2-yl-N-[2,2,2-trifluoro-1-methylethyl]pyrimidin-4-amine or pharmaceutically acceptable salts thereof.

15. The compound according to claim 1, 6-chloro-5-{4-[3-(dimethylamino)propoxy]-2,6-difluorophenyl}-2-pyrazin-2-yl-N-(2,2,2-trifluoroethyl)pyrimidin-4-amine or pharmaceutically acceptable salts thereof.

16. The compound according to claim 1, 6-chloro-5-{4-[3-(dimethylamino)propoxy]-2,6-difluorophenyl}-N-(2,2,2-trifluoroethyl)-2,2'-bipyrimidin-4-amine or pharmaceutically acceptable salts thereof.

17. The compound according to claim 1, 6-chloro-5-{4-[3-(dimethylamino)propoxy]-2,6-difluorophenyl}-2-(1H-imidazol-1-yl)-N-(2,2,2-trifluoroethyl)pyrimidin-4-amine or pharmaceutically acceptable salts thereof.

18. The compound according to claim 1, 6-chloro-5-{2,6-difluoro-4-[3-(dimethylamino)propoxy]phenyl}-2-(1H-pyrazol-1-yl)-N-[2,2,2-trifluoro-1-methylethyl)pyrimidin-4-amine or pharmaceutically acceptable salts thereof.

19. The compound according to claim 1, N-{3-[4-(4-chloro-6-cycloheptyl-2-pyrazin-2-ylpyrimidin-5-yl)-3,5-difluorophenoxy]propyl}-N-methylamine or pharmaceutically acceptable salts thereof.

20. The compound according to claim 1, 6-chloro-5-{4-[2-(dimethylamino)ethoxy]-2,6-difluorophenyl}-2-pyrazin-2-yl-N-(2,2,2-trifluoroethyl)pyrimidin-4-amine or pharmaceutically acceptable salts thereof.

21. The compound according to claim 1, 6-chloro-5-{4-[4-(dimethylamino)butoxy]-2,6-difluorophenyl}-2-pyrazin-2-yl-N-(2,2,2-trifluoroethyl)pyrimidin-4-amine or pharmaceutically acceptable salts thereof.

22. The compound according to claim 1, 6-chloro-5-{2,6-difluoro-4-[3-(methylamino)propoxy]phenyl}-2-pyridin-2-yl-N-[2,2,2-trifluoro-1-methylethyl]pyrimidin-4-amine or pharmaceutically acceptable salts thereof.

23. The compound according to claim 1, 6-chloro-5-{4-[3-(dimethylamino)propoxy]-2,6-difluorophenyl}-2-quinolin-2-yl-N-(2,2,2-trifluoroethyl)pyrimidin-4-amine or pharmaceutically acceptable salts thereof.

24. The compound according to claim 1, 2-(5-Azidopyridin-2-yl)-6-chloro-5-{4-[3-(dimethylamino)propoxy]-2,6-difluorophenyl}-N-(2,2,2-trifluoroethyl)pyrimidin-4-amine; or pharmaceutically acceptable salts thereof.

25. The compound according to claim 2, (4-chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide.

26. The compound according to claim 2, 6-chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine or pharmaceutically acceptable salts thereof.

27. The compound according to claim 2, 6-chloro-5-{2,6-difluoro-4-[3-(dimethylamino)propoxy]phenyl}-2-(1H-pyrazol-1-yl)-N-[(1S)-2,2,2-trifluoro-1-methylethyl)pyrimidin-4-amine or pharmaceutically acceptable salts thereof.

28. The compound according to claim 2, 6-chloro-5-{2,6-difluoro-4-[3-(methylamino)propoxy]phenyl}-2-pyridin-2-yl-N-[(1S)-2,2,2-trifluoro-1-methylethyl]pyrimidin-4-amine or pharmaceutically acceptable salts thereof.

29. The compound according to claim 3, (4-chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide or pharmaceutically acceptable salts thereof.

30. The compound according to claim 3, 6-chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine or pharmaceutically acceptable salts thereof.

31. The compound according to claim 3, 6-chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine or pharmaceutically acceptable salts thereof.

32. The compound according to claim 3, 6-chloro-5-{2,6-difluoro-4-[3-(methylamino)propoxy]phenyl}-2-pyridin-2-yl-N-[(1R)-2,2,2-trifluoro-1-methylethyl]pyrimidin-4-amine or pharmaceutically acceptable salts thereof.

33. A compound of Formula (I)

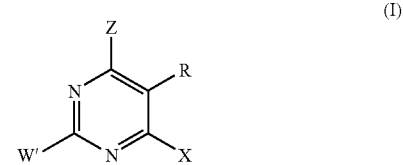

(I)

wherein:
Z is:

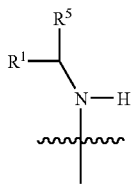

R is a moiety

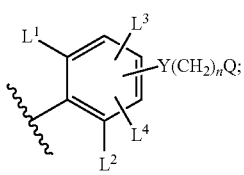

n is an integer of 2, 3, or 4;
$L^1$ and $L^2$, are each independently H, F, Cl or Br;
$L^3$ and $L^4$ are H;
X is Cl or Br;
Y is O, S, or —$NR^2$;
Q is OH or —$NR^3R^4$;
$R^1$ is H or $C_1$-$C_3$ alkyl;
$R^2$ is H or $C^1$-$C^3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;
W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;
$R^6$ is $C_1$-$C_3$ alkyl;
$R^7$ is $C_1$-$C_3$ alkyl;
or a pharmaceutically acceptable salt thereof
produced by the process which comprises the step of reacting a compound of the formula

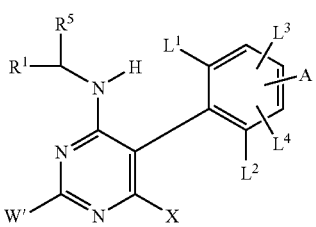

where A is a leaving group with a compound of the formula HY—$(CH_2)_nQ$ in the presence of a strong base optionally in the presence of an aprotic solvent to give a compound of Formula (I).

34. A compound produced by the process according to claim 33 wherein the leaving group A is F and Y is O.

35. A compound produced by the process according to claim 33 wherein the strong base is selected from an alkali metal hydroxide, alkali metal carbonate and alkali hydride.

36. A process for the preparation of a compound of Formula (I)

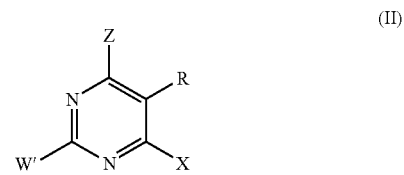

wherein:
Z is:

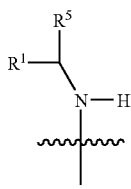

R is a moiety

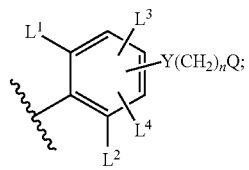

n is an integer of 2, 3, or 4;
$L^1$ and $L^2$, are each independently H, F, Cl or Br;
$L^3$ and $L^4$ are H;
X is Cl or Br;
Y is O, S, or —$NR^2$;
Q is OH or —$NR^3R^4$;
$R^1$ is H or $C_1$-$C_3$ alkyl;
$R^2$ is H or $C^1$—$C^3$ alkyl;
$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;
$R^5$ is $CF_3$ or $C_2F_5$;
W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

$R^6$ is $C_1$-$C_3$ alkyl;

$R^7$ is $C_1$-$C_3$ alkyl;

or a pharmaceutically acceptable salt thereof;

comprising the step of reacting a compound of the formula

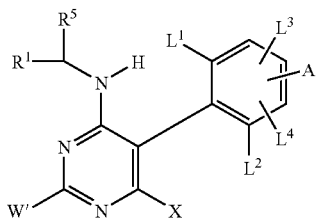

where A is a leaving with a compound of the formula HY—$(CH_2)_nQ$ in the presence of a strong base optionally in the presence of an aprotic solvent to give a compound of Formula (I).

37. A process according to claim 36 wherein the leaving group A is F and Y is O.

38. A process according to claim 36 wherein the strong base is selected from an alkali metal hydroxide, alkali metal carbonate and alkali hydride.

39. A process according to claim 36 wherein the aprotic solvent is selected from dimethylsulfoxide and dimethylformamide.

40. A process according to claim 36 wherein the aprotic solvent is selected from dimethylsulfoxide and dimethylformamide.

41. A pharmaceutical composition which comprises an effective amount of a compound of claim 1 or a pharmaceutically acceptable salt thereof together with a pharmaceutically acceptable carrier.

42. A method of treating non-small cell lung carcinoma in a mammal by administering an effective amount of a compound of Formula (I) as defined in claim 1 and pharmaceutically acceptable salts thereof.

43. A method of treating colon carcinoma in a mammal by administering an effective amount of a compound of Formula (I) as defined in claim 1 and pharmaceutically acceptable salts thereof.

44. A method of treating glioblastoma in a mammal by administering an effective amount of a compound of Formula (I) as defined in claim 1 and pharmaceutically acceptable salts thereof.

45. A method of treating non-small cell lung carcinoma in a mammal in need thereof by administering an effective amount of a compound of formula (II):

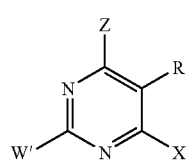

(II)

wherein:

Z is selected from:

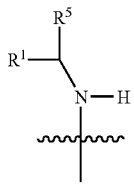

and $C_6$-$C_8$ cycloalkyl;

R is a moiety

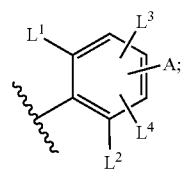

X is Cl or Br;

$L^1$, $L^2$, $L^3$ and $L^4$ are each independently H, F, Cl or Br;

A is H, F, Cl, Br, or $Y(CH_2)_nQ$;

Y is O, S, or —$NR^2$;

n is an integer of 2, 3, or 4;

Q is OH or —$NR^3R^4$;

$R^1$ is H or $C_1$-$C_3$ alkyl;

$R^2$ is H or $C_1$-$C_3$ alkyl;

$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;

$R^5$ is $CF_3$ or $C_2F_5$;

W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

$R^6$ is $C_1$-$C_3$ alkyl;

$R^7$ is $C_1$-$C_3$ alkyl;

or a pharmaceutically acceptable salt thereof.

46. A method according to claim 45 wherein formula II is represented by formula IIa

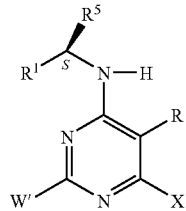
(IIa)

or pharmaceutically acceptable salts thereof.

47. A method according to claim 45 wherein formula II is represented by formula IIb

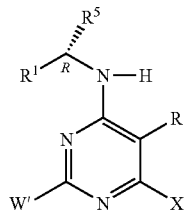
(IIb)

or pharmaceutically acceptable salts thereof.

48. A method according to claim 45 wherein R is

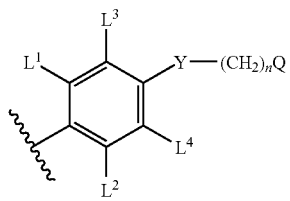

or pharmaceutically acceptable salts thereof.

49. A method according to claim 46 wherein:
R is a moiety

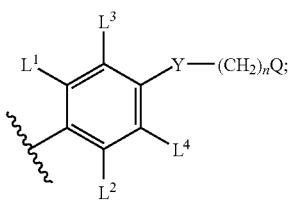

n=3;
Y is O;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;

R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

50. A method according to claim 47
R is a moiety

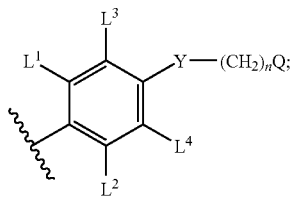

n=3;
Y is O;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

51. A method according to claim 46
wherein:
R is a moiety

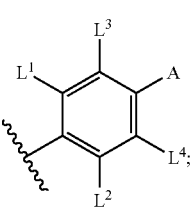

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

52. A method according to claim 47 wherein:

R is a moiety

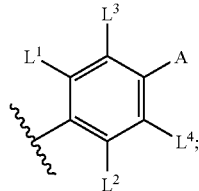

A is F;
R¹ is H or methyl;
R⁵ is CF₃;
R⁶ is C₁-C₃ alkyl;
L¹ is F;
L² is H or F;
L³ is H;
L⁴ is H;
X is Cl or Br;
or pharmaceutically acceptable salts thereof.

53. A method according to claim 46 wherein compounds are selected from
4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine,
6-Chloro-2-pyridin-4-yl-N-(2,2,2-trifluoroethyl)-5-(2,4,6-trifluorophenyl)pyrimidin-4-amine,
6-Chloro-2-pyridin-3-yl-N-(2,2,2-trifluoroethyl)-5-(2,4,6-trifluorophenyl)pyrimidin-4-amine,
6-Chloro-2-pyridin-2-yl-N-(2,2,2-trifluoroethyl)-5-(2,4,6-trifluorophenyl)pyrimidin-4-amine,
6-Chloro-2-pyridin-2-yl-N-[2,2,2-trifluoro-1-methylethyl]-5-(2,4,6-trifluorophenyl)pyrimidin-4-amine,
6-Chloro-2-quinolin-2-yl-N-(2,2,2-trifluoroethyl)-5-(2,4,6-trifluorophenyl)pyrimidin-4-amine,
6-Chloro-2-isoquinolin-1-yl-N-(2,2,2-trifluoroethyl)-5-(2,4,6-trifluorophenyl)pyrimidin-4-amine,
6-Chloro-2-isoquinolin-3-yl-N-(2,2,2-trifluoroethyl)-5-(2,4,6-trifluorophenyl)pyrimidin-4-amine,
6-Chloro-2-thien-2-yl-N-(2,2,2-trifluoroethyl)-5-(2,4,6-trifluorophenyl)pyrimidin-4-amine,
6-Chloro-2-(2-furyl)-N-(2,2,2-trifluoroethyl)-5-(2,4,6-trifluorophenyl)pyrimidin-4-amine,
6-Chloro-2-(1H-imidazol-1-yl)-N-(2,2,2-trifluoroethyl)-5-(2,4,6-trifluorophenyl)pyrimidin-4-amine,
6-Chloro-2-(1H-pyrazol-1-yl)-N-(2,2,2-trifluoroethyl)-5-(2,4,6-trifluorophenyl)pyrimidin-4-amine,
6-Chloro-2-(1H-pyrazol-1-yl)-N-[2,2,2-trifluoro-1-methylethyl)-5-(2,4,6-trifluorophenyl)pyrimidin-4-amine,
6-Chloro-2-(1H-pyrrol-1-yl)-N-(2,2,2-trifluoroethyl)-5-(2,4,6-trifluorophenyl)pyrimidin-4-amine,
4-Chloro-5-{4-[3-(dimethylamino)propoxy]-2,6-difluorophenyl}-6-[(2,2,2-trifluoroethyl)amino]pyrimidin-2-yl(methyl)cyanamide,
6-Chloro-5-{4-[3-(dimethylamino)propoxy]-2,6-difluorophenyl}-N²-methyl-N⁴-(2,2,2-trifluoroethyl)pyrimidine-2,4-diamine,
(4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
4-Chloro-5-{4-[2-(dimethylamino)ethoxy]-2,6-difluorophenyl}-6-[(2,2,2-trifluoroethyl)amino]pyrimidin-2-yl(methyl)cyanamide, {4-Chloro-5-{4-[4-(dimethylamino)butoxy]-2,6-difluorophenyl}-6-[(2,2,2-trifluoroethyl)amino]pyrimidin-2-yl}methylcyanamide,
6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
6-Chloro-5-{4-[3-(dimethylamino)propoxy]-2,6-difluorophenyl}-2-pyrazin-2-yl-N-(2,2,2-trifluoroethyl)pyrimidin-4-amine,
6-Chloro-5-{4-[3-(dimethylamino)propoxy]-2,6-difluorophenyl}-N-(2,2,2-trifluoroethyl)-2,2'-bipyrimidin-4-amine,
6-Chloro-5-{4-[2-(dimethylamino)ethoxy]-2,6-difluorophenyl}-2-pyrazin-2-yl-N-(2,2,2-trifluoroethyl)pyrimidin-4-amine,
6-Chloro-5-{4-[4-(dimethylamino)butoxy]-2,6-difluorophenyl}-2-pyrazin-2-yl-N-(2,2,2-trifluoroethyl)pyrimidin-4-amine,
6-Chloro-5-{2,6-difluoro-4-[3-(methylamino)propoxy]phenyl}-2-pyridin-2-yl-N-[2,2,2-trifluoro-1-methylethyl]pyrimidin-4-amine,
6-Chloro-5-{4-[3-(dimethylamino)propoxy]-2,6-difluorophenyl}-2-quinolin-2-yl-N-(2,2,2-trifluoroethyl)pyrimidin-4-amine,
6-Chloro-5-{4-[3-(dimethylamino)propoxy]-2,6-difluorophenyl}-2-(1H-imidazol-1-yl)-N-(2,2,2-trifluoroethyl)pyrimidin-4-amine,
6-Chloro-5-{2,6-difluoro-4-[3-(dimethylamino)propoxy]phenyl}-2-(1H-pyrazol-1-yl)-N-[2,2,2-trifluoro-1-methylethyl]pyrimidin-4-amine,
N-{3-[4-(4-Chloro-6-cycloheptyl-2-pyrazin-2-ylpyrimidin-5-yl)-3,5-difluorophenoxy]propyl}-N-methylamine,
6-Chloro-2-(1-methyl-1H-imidazol-2-yl)-N-(2,2,2-trifluoroethyl)-5-(2,4,6-trifluorophenyl)pyrimidin-4-amine,
6-Chloro-2-(1H-pyrrol-2-yl)-N-(2,2,2-trifluoroethyl)-5-(2,4,6-trifluorophenyl)pyrimidin-4-amine,
6-Chloro-2-(4-methylpyridin-2-yl)-N-(2,2,2-trifluoroethyl)-5-(2,4,6-trifluorophenyl)pyrimidin-4-amine,
6-Chloro-2-(5-nitropyridin-2-yl)-N-(2,2,2-trifluoroethyl)-5-(2,4,6-trifluorophenyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine
or pharmaceutically acceptable salts thereof.

54. A method according to claim 46 wherein the compounds are selected from:
6-Chloro-2-pyrazin-2-yl-N-[(1S)-2,2,2-trifluoro-1-methylethyl]-5-(2,4,6-trifluorophenyl)pyrimidin-4-amine,
6-Chloro-2-pyridin-2-yl-N-[(1S)-2,2,2-trifluoro-1-methylethyl]-5-(2,4,6-trifluorophenyl)pyrimidin-4-amine,
6-Chloro-2-(1H-pyrazol-1-yl)-N-[(1S)-2,2,2-trifluoro-1-methylethyl)-5-(2,4,6-trifluorophenyl)pyrimidin-4-amine,
(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and 6-Chloro-5-{2,6-difluoro-4-[3-(dimethylamino)propoxy]phenyl}-2-(1H-pyrazol-1-yl)-N-[(1S)-2,2,2-trifluoro-1-methylethyl)pyrimidin-4-amine; or pharmaceutically acceptable salts thereof.

55. A method according to claim 47 wherein the compounds are selected from:

6-Chloro-2-pyrazin-2-yl-N-[(1R)-2,2,2-trifluoro-1-methylethyl]-5-(2,4,6-trifluorophenyl)pyrimidin-4-amine, 6-Chloro-2-pyridin-2-yl-N-[(1R)-2,2,2-trifluoro-1-methylethyl]-5-(2,4,6-trifluorophenyl)pyrimidin-4-amine, 6-Chloro-2-(1H-pyrazol-1-yl)-N-[(1R)-2,2,2-trifluoro-1-methylethyl)-5-(2,4,6-trifluorophenyl)pyrimidin-4-amine, (4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and 6-Chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine or pharmaceutically acceptable salts thereof.

56. A method of treating colon carcinoma in a mammal by administering an effective amount of a compound of formula (II):

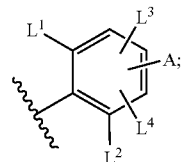

wherein:

Z is selected from:

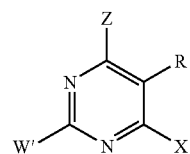

and $C_6$-$C_8$ cycloalkyl;

R is a moiety

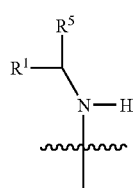

X is Cl or Br;

$L^1$, $L^2$, $L^3$ and $L^4$ are each independently H, F, Cl or Br;

A is H, F, Cl, Br, or $Y(CH_2)_n Q$;

Y is O, S, or —$NR^2$;

n is an integer of 2, 3, or 4;

Q is OH or —$NR^3 R^4$;

$R^1$ is H or $C_1$-$C_3$ alkyl;

$R^3$ and $R^4$ are each independently H or $C_1$-$C_3$ alkyl; or $R^3$ and $R^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with $R^7$;

$R^5$ is $CF_3$ or $C_2 F_5$;

W' is —$NHR^6$, —$N(CN)R^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

$R^6$ is $C_1$-$C_3$ alkyl;

$R^7$ is $C_1$-$C_3$ alkyl;

or a pharmaceutically acceptable salt thereof.

57. A method according to claim 56 wherein formula II is represented by formula IIa

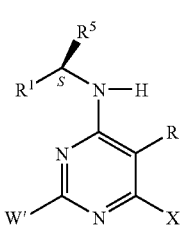

or pharmaceutically acceptable salts thereof.

58. A method according to claim 56 wherein formula II is represented by formula IIb

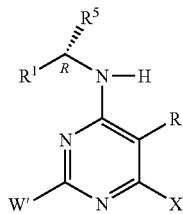
(IIb)

or pharmaceutically acceptable salts thereof.

59. A method according to claim 56 wherein R is

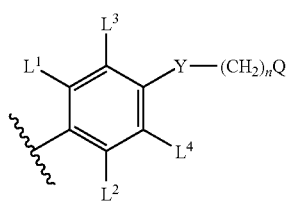

or pharmaceutically acceptable salts thereof.

60. A method according to claim 57 wherein:
R is a moiety

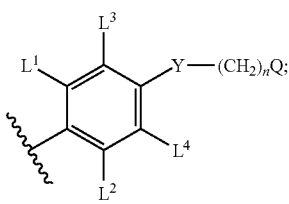

n=3;
Y is —O—;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

61. A method according to claim 58
R is a moiety

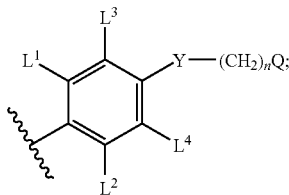

n=3;
Y is O;
Q is —NR$^6$R$^7$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

62. The method according to claim 57 wherein:
R is a moiety

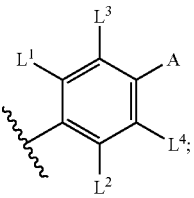

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

63. The method according to claim 58 wherein:

R is a moiety

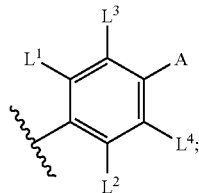

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

64. A method according to claim 56 wherein compounds are selected from
  4-Chloro-6-[(2,2,2-trifluoroethyl)amino]-5-(2,4,6-trifluorophenyl)pyrimidin-2-yl(methyl)cyanamide,
  4-Chloro-6-[(2,2,2-trifluoroethyl)amino]-5-(2,4,6-trifluorophenyl)pyrimidin-2-yl]ethylcyanamide,
  6-Chloro-2-pyrazin-2-yl-N-[2,2,2-trifluoro-1-methylethyl]-5-(2,4,6-trifluorophenyl)pyrimidin-4-amine,
  6-Chloro-2-pyrazin-2-yl-N-(2,2,2-trifluoroethyl)-5-(2,4,6-trifluorophenyl)pyrimidin-4-amine,
  6-Chloro-N-(2,2,2-trifluoroethyl)-5-(2,4,6-trifluorophenyl)-2,2'-bipyrimidin-4-amine,
  6-Chloro-2-pyridin-4-yl-N-(2,2,2-trifluoroethyl)-5-(2,4,6-trifluorophenyl)pyrimidin-4-amine,
  6-Chloro-2-pyridin-3-yl-N-(2,2,2-trifluoroethyl)-5-(2,4,6-trifluorophenyl)pyrimidin-4-amine,
  6-Chloro-2-pyridin-2-yl-N-(2,2,2-trifluoroethyl)-5-(2,4,6-trifluorophenyl)pyrimidin-4-amine,
  6-Chloro-2-pyridin-2-yl-N-[2,2,2-trifluoro-1-methylethyl]-5-(2,4,6-trifluorophenyl)pyrimidin-4-amine,
  6-Chloro-2-quinolin-2-yl-N-(2,2,2-trifluoroethyl)-5-(2,4,6-trifluorophenyl)pyrimidin-4-amine,
  6-Chloro-2-isoquinolin-1-yl-N-(2,2,2-trifluoroethyl)-5-(2,4,6-trifluorophenyl)pyrimidin-4-amine,
  6-Chloro-2-isoquinolin-3-yl-N-(2,2,2-trifluoroethyl)-5-(2,4,6-trifluorophenyl)pyrimidin-4-amine,
  6-Chloro-2-thien-2-yl-N-(2,2,2-trifluoroethyl)-5-(2,4,6-trifluorophenyl)pyrimidin-4-amine,
  6-Chloro-2-(2-furyl)-N-(2,2,2-trifluoroethyl)-5-(2,4,6-trifluorophenyl)pyrimidin-4-amine,
  6-Chloro-2-(1H-imidazol-1-yl)-N-(2,2,2-trifluoroethyl)-5-(2,4,6-trifluorophenyl)pyrimidin-4-amine,
  6-Chloro-2-(1H-pyrazol-1-yl)-N-(2,2,2-trifluoroethyl)-5-(2,4,6-trifluorophenyl)pyrimidin-4-amine,
  6-Chloro-2-(1H-pyrazol-1-yl)-N-[2,2,2-trifluoro-1-methylethyl)-5-(2,4,6-trifluorophenyl)pyrimidin-4-amine,
  6-Chloro-2-(1H-pyrrol-1-yl)-N-(2,2,2-trifluoroethyl)-5-(2,4,6-trifluorophenyl)pyrimidin-4-amine,
  4-Chloro-5-[(4-[3-(dimethylamino)propoxy]-2,6-difluorophenyl]-6-[(2,2,2-trifluoroethyl)amino]pyrimidin-2-yl(methyl)cyanamide,
  6-Chloro-5-{4-[3-(dimethylamino)propoxy]-2,6-difluorophenyl}-N$^2$-methyl-N$^4$-(2,2,2-trifluoroethyl)pyrimidine-2,4-diamine,
  (4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
  4-Chloro-5-{4-[2-(dimethylamino)ethoxy]-2,6-difluorophenyl}-6-[(2,2,2-trifluoroethyl)amino]pyrimidin-2-yl(methyl)cyanamide,
  {4-Chloro-5-{4-[4-(dimethylamino)butoxy]-2,6-difluorophenyl}-6-[(2,2,2-trifluoroethyl)amino]pyrimidin-2-yl}methylcyanamide,
  6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
  6-Chloro-5-{4-[3-(dimethylamino)propoxy]-2,6-difluorophenyl}-2-pyrazin-2-yl-N-(2,2,2-trifluoroethyl)pyrimidin-4-amine,
  6-Chloro-5-{4-[3-(dimethylamino)propoxy]-2,6-difluorophenyl}-N-(2,2,2-trifluoroethyl)-2,2'-bipyrimidin-4-amine,
  6-Chloro-5-{4-[2-(dimethylamino)ethoxy]-2,6-difluorophenyl}-2-pyrazin-2-yl-N-(2,2,2-trifluoroethyl)pyrimidin-4-amine,
  6-Chloro-5-{4-[4-(dimethylamino)butoxy]-2,6-difluorophenyl}-2-pyrazin-2-yl-N-(2,2,2-trifluoroethyl)pyrimidin-4-amine,
  6-Chloro-5-{2,6-difluoro-4-[3-(methylamino)propoxy]phenyl}-2-pyridin-2-yl-N-[2,2,2-trifluoro-1-methylethyl]pyrimidin-4-amine,
  6-Chloro-5-{4-[3-(dimethylamino)propoxy]-2,6-difluorophenyl}-2-quinolin-2-yl-N-(2,2,2-trifluoroethyl)pyrimidin-4-amine,
  6-Chloro-5-{4-[3-(dimethylamino)propoxy]-2,6-difluorophenyl}-2-(1H-imidazol-1-yl)-N-(2,2,2-trifluoroethyl)pyrimidin-4-amine,
  6-Chloro-5-{2,6-difluoro-4-[3-(methylamino)propoxy]phenyl}-2-(1H-pyrazol-1-yl)-N-[2,2,2-trifluoro-1-methylethyl]pyrimidin-4-amine,
  N-{3-[4-(4-Chloro-6-cycloheptyl-2-pyrazin-2-ylpyrimidin-5-yl)-3,5-difluorophenoxy]propyl}-N-methylamine,
  6-Chloro-2-(1-methyl-1H-imidazol-2-yl)-N-(2,2,2-trifluoroethyl)-5-(2,4,6-trifluorophenyl)pyrimidin-4-amine,
  6-Chloro-2-(1H-pyrrol-2-yl)-N-(2,2,2-trifluoroethyl)-5-(2,4,6-trifluorophenyl)pyrimidin-4-amine,
  6-Chloro-2-(4-methylpyridin-2-yl)-N-(2,2,2-trifluoroethyl)-5-(2,4,6-trifluorophenyl)pyrimidin-4-amine,
  6-Chloro-2-(5-nitropyridin-2-yl)-N-(2,2,2-trifluoroethyl)-5-(2,4,6-trifluorophenyl)pyrimidin-4-amine and
  2-(5-Azidopyridin-2-yl)-6-chloro-5-{4-[3-(dimethylamino)propoxy]-2,6-difluorophenyl}-N-(2,2,2-trifluoroethyl)pyrimidin-4-amine
or pharmaceutically acceptable salts thereof.

65. A method according to claim 57 wherein the compounds are selected from:
  6-Chloro-2-pyrazin-2-yl-N-[(1S)-2,2,2-trifluoro-1-methylethyl]-5-(2,4,6-trifluorophenyl)pyrimidin-4-amine,
  6-Chloro-2-pyridin-2-yl-N-[(1S)-2,2,2-trifluoro-1-methylethyl]-5-(2,4,6-trifluorophenyl)pyrimidin-4-amine,
  6-Chloro-2-(1H-pyrazol-1-yl)-N-[(1S)-2,2,2-trifluoro-1-methylethyl)-5-(2,4,6-trifluorophenyl)pyrimidin-4-amine,
  (4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(S)-2,2,2-trifluoro-1-methylethyl]pyrimidin-4-amine and 6-Chloro-5-{2,6-difluoro-4-[3-(dimethylamino)propoxy]phenyl}-2-(1H-pyrazol-1-yl)-N-[(1S)-2,2,2-trifluoro-1-methylethyl)pyrimidin-4-amine or pharmaceutically acceptable salts thereof.

66. A method according to claim 58 wherein the compounds are selected from:

6-Chloro-2-pyrazin-2-yl-N-[(1R)-2,2,2-trifluoro-1-methylethyl]-5-(2,4,6-trifluorophenyl)pyrimidin-4-amine, 6-Chloro-2-pyridin-2-yl-N-[(1R)-2,2,2-trifluoro-1-methylethyl]-5-(2,4,6-trifluorophenyl)pyrimidin-4-amine, 6-Chloro-2-(1H-pyrazol-1-yl)-N-[(1R)-2,2,2-trifluoro-1-methylethyl]-5-(2,4,6-trifluorophenyl)pyrimidin-4-amine, (4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and 6-Chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine or pharmaceutically acceptable salts thereof.

67. A method of treating glioblastoma in a mammal by administering an effective amount of a compound of formula (II) or a pharmaceutically acceptable salt thereof

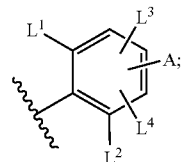

wherein:

Z is selected from:

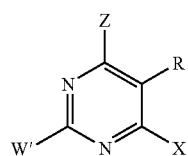

and $C_6$-$C_8$ cycloalkyl;

R is a moiety

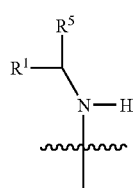

X is Cl or Br;

$L^1$, $L^2$, $L^3$ and $L^4$ are each independently H, F, Cl or Br;

A is H, F, Cl, Br, or Y(CH$_2$)$_n$Q;

Y is O, S, or —NR$^2$;

n is an integer of 2, 3, or 4;

Q is OH or —NR$^3$R$^4$;

R$^1$ is H or $C_1$-$C_3$ alkyl;

R$^3$ and R$^4$ are each independently H or $C_1$-$C_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;

R$^5$ is CF$_3$ or C$_2$F$_5$;

W' is —NHR$^6$, —N(CN)R$^6$, aryl of 6 to 12 carbon atoms optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups; or heteroaryl of 5 to 10 ring atoms having from 1 to 4 heteroatoms selected from S, O and N and optionally substituted with 1-3 groups independently selected from halogen, azido, nitro, cyano, hydroxy, $C_1$-$C_3$ alkyl, $C_1$-$C_3$ alkoxy, amino, $C_1$-$C_3$ alkylamino, $C_1$-$C_3$ dialkylamino, formyl, $C_1$-$C_3$ alkoxycarbonyl, carboxyl, $C_1$-$C_3$ alkanoyl, $C_1$-$C_3$ alkylthio, $C_1$-$C_3$ alkylamido, phenyl, phenoxy, benzyl, benzoxy, furyl, and cyclopropyl groups;

R$^6$ is $C_1$-$C_3$ alkyl;

R$^7$ is $C_1$-$C_3$ alkyl;

or a pharmaceutically acceptable salt thereof.

68. A method according to claim 67 wherein formula (II) is represented by formula (IIa)

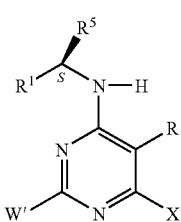

or pharmaceutically acceptable salts thereof.

69. A method according to claim 67 wherein formula (II) is represented by formula (IIb)

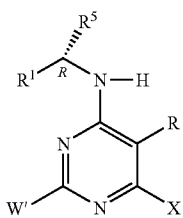

or pharmaceutically acceptable salts thereof.

70. A method according to claim 67 wherein R is a moiety

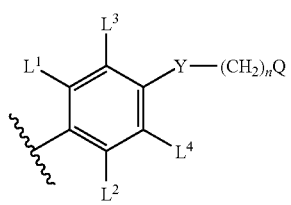

or a pharmaceutically acceptable salt thereof.

71. A method according to claim 68 wherein:
R is a moiety

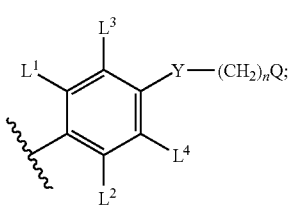

n=3;
Y is O;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

72. A method according to claim 69 wherein:
R is a moiety

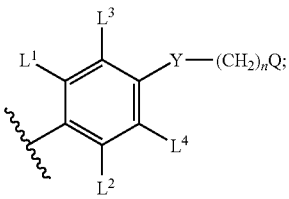

n=3;
Y is O;
Q is —NR$^3$R$^4$;
R$^1$ is H or methyl;
R$^5$ is CF$_3$;
R$^3$ and R$^4$ are each independently H or C$_1$-C$_3$ alkyl; or R$^3$ and R$^4$ when optionally taken together with the nitrogen atom to which each is attached form a saturated 4 to 6 member heterocyclic ring which contains 1-2 nitrogen atoms, 0-1 oxygen atoms and 0-1 sulfur atoms within the ring where said ring is optionally substituted with R$^7$;
R$^6$ is C$_1$-C$_3$ alkyl;
R$^7$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

73. A method according to claim 68 wherein:
R is a moiety

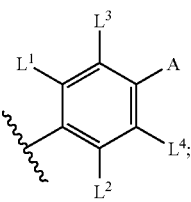

A is F;
R$^1$ is H or methyl;
R$^5$ is CF$_3$;
R$^6$ is C$_1$-C$_3$ alkyl;
L$^1$ is F;
L$^2$ is H or F;
L$^3$ is H;
L$^4$ is H;
X is Cl or Br;
or pharmaceutically acceptable salts thereof.

74. A method according to claim 69 wherein:
R is a moiety

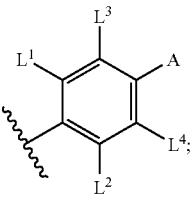

A is F;
R$^1$ is H or methyl;
R$^5$ is CF$_3$;
R$^6$ is C$_1$-C$_3$ alkyl;
L$^1$ is F;

$L^2$ is H or F;
$L^3$ is H;
$L^4$ is H;
X is Cl or Br;
or pharmaceutically acceptable salts thereof.

75. A method according to claim 67 wherein compounds are selected from
4-Chloro-6-[(2,2,2-trifluoroethyl)amino]-5-(2,4,6-trifluorophenyl)pyrimidin-2-yl(methyl)cyanamide,
4-Chloro-6-[(2,2,2-trifluoroethyl)amino]-5-(2,4,6-trifluorophenyl)pyrimidin-2-yl]ethylcyanamide,
6-Chloro-2-pyrazin-2-yl-N-[2,2,2-trifluoro-1-methylethyl]-5-(2,4,6-trifluorophenyl)pyrimidin-4-amine,
6-Chloro-2-pyrazin-2-yl-N-(2,2,2-trifluoroethyl)-5-(2,4,6-trifluorophenyl)pyrimidin-4-amine,
6-Chloro-N-(2,2,2-trifluoroethyl)-5-(2,4,6-trifluorophenyl)-2,2'-bipyrimidin-4-amine,
6-Chloro-2-pyridin-4-yl-N-(2,2,2-trifluoroethyl)-5-(2,4,6-trifluorophenyl)pyrimidin-4-amine,
6-Chloro-2-pyridin-3-yl-N-(2,2,2-trifluoroethyl)-5-(2,4,6-trifluorophenyl)pyrimidin-4-amine,
6-Chloro-2-pyridin-2-yl-N-(2,2,2-trifluoroethyl)-5-(2,4,6-trifluorophenyl)pyrimidin-4-amine,
6-Chloro-2-pyridin-2-yl-N-[2,2,2-trifluoro-1-methylethyl]-5-(2,4,6-trifluorophenyl)pyrimidin-4-amine,
6-Chloro-2-quinolin-2-yl-N-(2,2,2-trifluoroethyl)-5-(2,4,6-trifluorophenyl)pyrimidin-4-amine,
6-Chloro-2-isoquinolin-1-yl-N-(2,2,2-trifluoroethyl)-5-(2,4,6-trifluorophenyl)pyrimidin-4-amine,
6-Chloro-2-isoquinolin-3-yl-N-(2,2,2-trifluoroethyl)-5-(2,4,6-trifluorophenyl)pyrimidin-4-amine,
6-Chloro-2-thien-2-yl-N-(2,2,2-trifluoroethyl)-5-(2,4,6-trifluorophenyl)pyrimidin-4-amine,
6-Chloro-2-(2-furyl)-N-(2,2,2-trifluoroethyl)-5-(2,4,6-trifluorophenyl)pyrimidin-4-amine,
6-Chloro-2-(1H-imidazol-1-yl)-N-(2,2,2-trifluoroethyl)-5-(2,4,6-trifluorophenyl)pyrimidin-4-amine,
6-Chloro-2-(1H-pyrazol-1-yl)-N-(2,2,2-trifluoroethyl)-5-(2,4,6-trifluorophenyl)pyrimidin-4-amine,
6-Chloro-2-(1H-pyrazol-1-yl)-N-[2,2,2-trifluoro-1-methylethyl]-5-(2,4,6-trifluorophenyl)pyrimidin-4-amine,
6-Chloro-2-(1H-pyrrol-1-yl)-N-(2,2,2-trifluoroethyl)-5-(2,4,6-trifluorophenyl)pyrimidin-4-amine,
4-Chloro-5-{4-[3-(dimethylamino)propoxy]-2,6-difluorophenyl}-6-[(2,2,2-trifluoroethyl)amino]pyrimidin-2-yl(methyl)cyanamide,
6-Chloro-5-{4-[3-(dimethylamino)propoxy]-2,6-difluorophenyl}-$N^2$-methyl-$N^4$-(2,2,2-trifluoroethyl)pyrimidine-2,4-diamine,
(4-Chloro-5-{4-[3-(dimethylamino)propoxy]-2,6-difluorophenyl}-6-{[2,2,2-trifluoro-1-methylethyl]amino}pyrimidin-2-yl)methylcyanamide,
4-Chloro-5-{4-[2-(dimethylamino)ethoxy]-2,6-difluorophenyl}-6-[(2,2,2-trifluoroethyl)amino]pyrimidin-2-yl(methyl)cyanamide,
{4-Chloro-5-{4-[4-(dimethylamino)butoxy]-2,6-difluorophenyl}-6-[(2,2,2-trifluoroethyl)amino]pyrimidin-2-yl}methylcyanamide,
6-Chloro-5-{2,6-difluoro-4-[3-(methylamino)propoxy]phenyl}-2-pyrazin-2-yl-N-[2,2,2-trifluoro-1-methylethyl]pyrimidin-4-amine,
6-Chloro-5-{4-[3-(dimethylamino)propoxy]-2,6-difluorophenyl}-2-pyrazin-2-yl-N-(2,2,2-trifluoroethyl)pyrimidin-4-amine,
6-Chloro-5-{4-[3-(dimethylamino)propoxy]-2,6-difluorophenyl}-N-(2,2,2-trifluoroethyl)-2,2'-bipyrimidin-4-amine,
6-Chloro-5-{4-[2-(dimethylamino)ethoxy]-2,6-difluorophenyl}-2-pyrazin-2-yl-N-(2,2,2-trifluoroethyl)pyrimidin-4-amine,
6-Chloro-5-{4-[4-(dimethylamino)butoxy]-2,6-difluorophenyl}-2-pyrazin-2-yl-N-(2,2,2-trifluoroethyl)pyrimidin-4-amine,
6-Chloro-5-{2,6-difluoro-4-[3-(methylamino)propoxy]phenyl}-2-pyridin-2-yl-N-[2,2,2-trifluoro-1-methylethyl]pyrimidin-4-amine,
6-Chloro-5-{4-[3-(dimethylamino)propoxy]-2,6-difluorophenyl}-2-quinolin-2-yl-N-(2,2,2-trifluoroethyl)pyrimidin-4-amine,
6-Chloro-5-{4-[3-(dimethylamino)propoxy]-2,6-difluorophenyl}-2-(1H-imidazol-1-yl)-N-(2,2,2-trifluoroethyl)pyrimidin-4-amine,
6-Chloro-5-{2,6-difluoro-4-[3-(dimethylamino)propoxy]phenyl}-2-(1H-pyrazol-1-yl)-N-[2,2,2-trifluoro-1-methylethyl]pyrimidin-4-amine,
N-{3-[4-(4-Chloro-6-cycloheptyl-2-pyrazin-2-ylpyrimidin-5-yl)-3,5-difluorophenoxy]propyl}-N-methylamine,
6-Chloro-2-(1-methyl-1H-imidazol-2-yl)-N-(2,2,2-trifluoroethyl)-5-(2,4,6-trifluorophenyl)pyrimidin-4-amine,
6-Chloro-2-(1H-pyrrol-2-yl)-N-(2,2,2-trifluoroethyl)-5-(2,4,6-trifluorophenyl)pyrimidin-4-amine,
6-Chloro-2-(4-methylpyridin-2-yl)-N-(2,2,2-trifluoroethyl)-5-(2,4,6-trifluorophenyl)pyrimidin-4-amine,
6-Chloro-2-(5-nitropyridin-2-yl)-N-(2,2,2-trifluoroethyl)-5-(2,4,6-trifluorophenyl)pyrimidin-4-amine and
2-(5-Azidopyridin-2-yl)-6-chloro-5-{4-[3-(dimethylamino)propoxy]-2,6-difluorophenyl}-N-(2,2,2-trifluoroethyl)pyrimidin-4-amine
or pharmaceutically acceptable salts thereof.

76. A method according to claim 68 wherein the compounds are selected from
6-Chloro-2-pyrazin-2-yl-N-[(1S)-2,2,2-trifluoro-1-methylethyl]-5-(2,4,6-trifluorophenyl)pyrimidin-4-amine,
6-Chloro-2-pyridin-2-yl-N-[(1S)-2,2,2-trifluoro-1-methylethyl]-5-(2,4,6-trifluorophenyl)pyrimidin-4-amine,
6-Chloro-2-(1H-pyrazol-1-yl)-N-[(1S)-2,2,2-trifluoro-1-methylethyl]-5-(2,4,6-trifluorophenyl)pyrimidin-4-amine,
(4-Chloro-5-{4-[3-(dimethylamino)propoxy]-2,6-difluorophenyl}-6-{[(1S)-2,2,2-trifluoro-1-methylethyl]amino}pyrimidin-2-yl)methylcyanamide,
6-Chloro-5-{2,6-difluoro-4-[3-(methylamino)propoxy]phenyl}-2-pyrazin-2-yl-N-[(1S)-2,2,2-trifluoro-1-methylethyl]pyrimidin-4-amine,
6-Chloro-5-{2,6-difluoro-4-[3-(methylamino)propoxy]phenyl}-2-pyridin-2-yl-N-[(1S)-2,2,2-trifluoro-1-methylethyl]pyrimidin-4-amine and
6-Chloro-5-{2,6-difluoro-4-[3-(dimethylamino)propoxy]phenyl}-2-(1H-pyrazol-1-yl)-N-[(1S)-2,2,2-trifluoro-1-methylethyl]pyrimidin-4-amine
or pharmaceutically acceptable salts thereof.

77. A method according to claim 69 wherein the compounds are selected from
6-Chloro-2-pyrazin-2-yl-N-[(1R)-2,2,2-trifluoro-1-methylethyl]-5-(2,4,6-trifluorophenyl)pyrimidin-4-amine,
6-Chloro-2-pyridin-2-yl-N-[(1R)-2,2,2-trifluoro-1-methylethyl]-5-(2,4,6-trifluorophenyl)pyrimidin-4-amine, 6-Chloro-2-(1H-pyrazol-1-yl)-N-[(1R)-2,2,2-trifluoro-1-methylethyl)-5-(2,4,6-trifluorophenyl)pyrimidin-4-amine, (4-Chloro-5-{4-[3-(dimethylamino)propoxy]-2,6-difluorophenyl}-6-{[(1R)-2,2,2-trifluoro-1-methylethyl]amino}pyrimidin-2-yl)methylcyanamide, 6-Chloro-5-{2,6-difluoro-4-[3-(methylamino)propoxy]phenyl}-2-pyrazin-2-yl-N-[(1R)-2,2,2-trifluoro-1-methylethyl]pyrimidin-4-amine, 6-Chloro-5-{2,6-difluoro-4-[3-(methylamino)propoxy]phenyl}-2-pyridin-2-yl-N-[(1R)-2,2,2-trifluoro-1-methylethyl]pyrimidin-4-amine and 6-Chloro-5-{2,6-difluoro-4-[3-(dimethylamino)propoxy]phenyl}-2-(1H-pyrazol-1-yl)-N-[(1R)-2,2,2-trifluoro-1-methylethyl)pyrimidin-4-amine.

* * * * *